United States Patent
Barrett et al.

(10) Patent No.: US 11,345,690 B2
(45) Date of Patent: May 31, 2022

(54) METHODS OF SYNTHESIZING A DIFLUOROLACTAM ANALOG

(71) Applicant: Cayman Chemical Company, Inc., Ann Arbor, MI (US)

(72) Inventors: Stephen Douglas Barrett, Hartland, MI (US); Joseph Michael Colombo, Ann Arbor, MI (US); Bradlee David Germain, Ann Arbor, MI (US); Andriy Kornilov, Ypsilanti, MI (US); James Bernard Kramer, Sylvania, OH (US); Adam Uzieblo, Farmington Hills, MI (US)

(73) Assignee: Cayman Chemical Company, Inc., Ann Arbor, MI (US)

( * ) Notice: Subject to any disclaimer, the term of this patent is extended or adjusted under 35 U.S.C. 154(b) by 32 days.

(21) Appl. No.: 16/299,916

(22) Filed: Mar. 12, 2019

(65) Prior Publication Data
US 2019/0202816 A1 Jul. 4, 2019
US 2022/0127252 A9 Apr. 28, 2022

Related U.S. Application Data

(62) Division of application No. 15/883,724, filed on Jan. 30, 2018, now abandoned, which is a division of application No. 14/775,591, filed as application No. PCT/US2014/028933 on Mar. 14, 2014, now Pat. No. 9,914,725.

(60) Provisional application No. 61/799,334, filed on Mar. 15, 2013.

(51) Int. Cl.
| | |
|---|---|
| C07D 409/06 | (2006.01) |
| C07D 333/38 | (2006.01) |
| C07D 207/273 | (2006.01) |
| C07D 498/04 | (2006.01) |
| C07F 9/40 | (2006.01) |

(52) U.S. Cl.
CPC ....... *C07D 409/06* (2013.01); *C07D 207/273* (2013.01); *C07D 333/38* (2013.01); *C07D 498/04* (2013.01); *C07F 9/4006* (2013.01)

(58) Field of Classification Search
CPC .................................................. C07D 409/06
See application file for complete search history.

(56) References Cited

U.S. PATENT DOCUMENTS

| | | |
|---|---|---|
| 3,975,399 A | 8/1976 | DeFranco et al. |
| 4,073,934 A | 2/1978 | Skuballa et al. |
| 4,177,346 A | 2/1979 | Nelson |
| 4,456,613 A | 6/1984 | Wang |
| 6,849,657 B2 | 2/2005 | Elworthy et al. |
| 7,276,531 B2 | 10/2007 | Araldi et al. |
| 7,419,999 B2 | 9/2008 | Araldi et al. |

| | | |
|---|---|---|
| 2005/0239872 A1 | 10/2005 | Billot et al. |
| 2006/0167081 A1 | 7/2006 | Billot et al. |
| 2015/0175538 A1* | 6/2015 | Barrett .............. A61P 19/10 514/422 |

FOREIGN PATENT DOCUMENTS

| | | |
|---|---|---|
| CA | 1085859 | 9/1980 |
| EP | 0046082 B1 | 6/1985 |
| GB | 1553595 A1 | 10/1979 |
| GB | 1583163 A1 | 1/1981 |
| WO | WO 2002/042268 A2 | 5/2002 |
| WO | WO 2003/007941 A1 | 1/2003 |
| WO | WO 2003/008377 A1 | 1/2003 |
| WO | WO 2003/047513 A2 | 6/2003 |
| WO | WO 2003/077910 A1 | 9/2003 |
| WO | WO 2003/103604 A2 | 12/2003 |
| WO | WO 2004/037786 A2 | 5/2004 |
| WO | WO 2009/023193 A1 | 2/2009 |
| WO | WO 2009/055289 A2 | 4/2009 |
| WO | WO 2011/003058 A1 | 1/2011 |
| WO | WO 2012/063207 A1 | 5/2012 |

(Continued)

OTHER PUBLICATIONS

Billot, X. et al. "Discovery of a Potent and Selective Agonist of the Prostaglandin $EP_4$ Receptor," *Biorganic & Medicinal Chemistry Letters*, 2003, 13, 1129-1132.

Cameron, K.O. et al. "Discovery of Highly Selective EP4 Receptor Agonists That Stimulate New Bone Formation and Restore Bone Mass in Ovariectomized Rats," *Biorganic & Medicinal Chemistry letters*, 2006, 16, 1799-1802.

Database PubChem Compound [Online] NCBI; Nov. 30, 2012, XP002725496, Database accession No. CID 66622708, compound CID 66622708.

Elworthy, T.R. et al. "Lactams as $EP_4$ Prostanoid Receptor Agonists. 3. Discovery of *N*-Ethylbenzoic Acid 2-Pyrrodlidinones as Subtype Selective Agents," *J. Med. Chem.* 2004, 20, 6124-6127.

Elworthy, T.R. et al. "Lactams as $EP_4$ Prostanoid Receptor Subtype Selective Agonists. Part 1:2-Pyrrolidinones-Stereochemical and Lower Side-Chain Optimization," *Biorganic & Medicinal Chemistry Letters*, 2004, 14, 1655-1659.

(Continued)

*Primary Examiner* — Shawquia Jackson
(74) *Attorney, Agent, or Firm* — Barnes & Thornburg LLP; Ryan L. Marshall

(57) ABSTRACT

The present invention relates to processes and intermediates for preparing compounds of formula (IA), wherein $R^1$, $R^4$, $R^5$, $R^6$, and $L^1$ are as defined herein. Compounds of formula (IA) have been found useful as $EP_4$ receptor agonists useful in the treatment of glaucoma, osteoporosis, neuropathic pain, and related disorders.

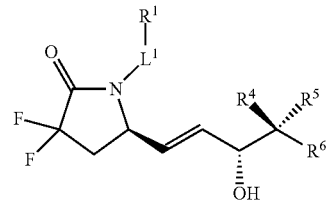

(IA)

3 Claims, No Drawings

(56) References Cited

FOREIGN PATENT DOCUMENTS

| WO | WO 2014/015246 A1 | 1/2014 |
| WO | WO 2014/015247 A1 | 1/2014 |

OTHER PUBLICATIONS

Fustero, S. et al. "A New Tandem Cross Metathesis-Intramolecular Aza-Michael Reaction for the Synthesis of α,α-Diflourinated Lactams," *Synthesis*, 2012, 44, 1863-1873.

International Search Report and Written Opinion for corresponding International Application No. PCT/US2014/028933, dated Mar. 30, 2015 (17 pages).

Kambe, T. et al., "Discovery of novel prostaglandin analogs as potent and selective EP2/EP4 dual agonists," *Bioorganic & Medicinal Chemistry* 20 (2012) 2235-2251.

Kambe, T. et al. "Synthesis and Evaluation of γ-lactam Analogs of $PGE_2$ as EP4 and EP2/Ep4 Agonists," *Bioorganic & Medicinal Chemistry*, 2012, 20, 3502-3522.

Kirk, K.L. et al., "Fluorination in Medicinal Chemistry: Methods, Strategies, and Recent Developments," *Organic Process Research & Development*, 2008, 12, 305-321.

Konas, D.W. et al., "Synthesis of $_L$-4,4-Difluoroglutamic Acid via Electrophilic Difluorination of a Lactam," *Organic Letters*, 1999, 1(13), 2105-2107.

Li, B-H et al. "Rational and Practical Synthesis of α,α-difluoro-γ-lactams," *J. Fluorine Chemistry*, 2012, 133, 163-166.

Ma, J-A et al., "Asymmetric Fluorination, Trifluoromethylation, and Perfluoroalkylation Reactions," *Chem. Rev.* 2004, 104, 6119-6146.

Martinez-Montero, S., et al., "Synthesis, evaluation of anti-HIV-1 and anti-HCV activity of novel 2',3'-dideoxy-2',2'-difluoro-4'-azanucleosides," *Bioorganic & Medicinal Chemistry* 20 (2012) 6885-6893.

Nair S.K. et al "Novel Synthesis of CP-734432, and EP4 Agonist, Using Sharpless Asymmetric Dihydroxylation," *Tetrahedron Letters*, 2010, 51, 1451-1454.

Sankar, G. et al., "Electrophilic NF Fluorinating Agents," *Chem. Rev.* 1996, 1737-1755.

Skuballa, W. et al., "Synthesis of a New Chemically and Metabolically Stable Prostacyclin Analogue with High and Long-Lasting Oral Activity," *Journal of Medicinal Chemistry*, 1986, 29(3), 313-315.

Smith, R.L. et al. "Prostaglandin Isosteres. 1. (8-Aza-, 8, 10-Diaza-, and 8-Aza-11-thia)-9-oxoprostanoic Acids and Their Derivatives," *J. Med. Chem.* 1977, 20, 1292-1299.

Wang, C-L.J. et al. "Azaprostanoids I. Synthesis of (RAC)-8-Aza-11-Deoxy-15-Deoxy-16-Hydroxy-16-Methylprostaglandins," *Tetrahedron Letters*, 1982, 10, 1067-1070.

Xiao, Y. et al "Synthesis and Evaluation of a γ-lactam as a Highly Selective $EP_2$ and $EP_4$ Receptor Agonist," *Biorganic & Medicinal Chemistry Letters*, 2008, 18, 821-824.

Ye, Z et al., "Asymmetric Synthesis of Fluorine-containing Compounds Using Organocatalysts," *Chimia*, 2011, 65(12), 902-908.

\* cited by examiner

METHODS OF SYNTHESIZING A DIFLUOROLACTAM ANALOG

CROSS-REFERENCE TO RELATED APPLICATIONS

This application is a divisional of U.S. application Ser. No. 15/883,724, filed Jan. 30, 2018, the entire contents of which is hereby incorporated herein by reference. U.S. application Ser. No. 15/883,724, is a divisional of U.S. application Ser. No. 14/775,591, filed Sep. 11, 2015, now U.S. Pat. No. 9,914,725, the entire contents of which is hereby incorporated herein by reference. U.S. Application No. 14/775,591, is a National Stage application of International Application No. PCT/US2014/028933 filed Mar. 14, 2014, which claims the benefit of U.S. Provisional Application No. 61/799,334, filed Mar. 15, 2013, entire contents of all of which are incorporated herein in their entirety.

FIELD OF THE INVENTION

The subject matter disclosed and claimed herein relates to processes and intermediates for the preparation of difluorolactams that are useful for treating $EP_4$ receptor mediated diseases and conditions.

BACKGROUND OF THE INVENTION

All references, including patents and patent applications, are hereby incorporated by reference in their entireties.

$EP_4$ receptor agonists are reported to be useful in lowering intraocular pressure and to have application in treating glaucoma. Prasanna, G. et al., *Exp. Eye Res.*, 2009, 89 (5), 608-17; Luu, K. et al., *J. Pharmacol. Exp. Ther.* 2009, 331(2), 627-635; Saeki, T. et al, *Invest. Ophthalmol. Vis. Sci.*, 2009, 50 (5) 2201-2208.

$EP_4$ receptor agonists are also reported to induce bone remodeling and to have use in the treatment of osteoporosis. Iwaniec, U. et al., *Osteoporosis International*, 2007, 18 (3), 351-362; Aguirre, J. et al., *J. Bone and Min. Res.*, 2007, 22(6), 877-888; Yoshida, K. et al., *Proc. Natl. Acad. Sci. USA*, 2002, 99 (7), 4580-4585. Hayashi, K. et al., *J. Bone Joint Surg. Br.*, 2005, 87-B (8), 1150-6.

Applicants have discovered that various 1,5-disubstituted 3,3-difluoropyrrolidin-2-ones (α,α-difluorolactams, or difluorolactams) have potent $EP_4$ receptor agonist activity. A published method of fluorine incorporation into the lactam scaffold possesses inherent inefficiencies for manufacturing large-scale quantities of a key difluorolactam intermediate and subsequent intermediates and target compounds; namely, a protection step requiring either impractically-large volumes of solvent and reagent for large scale production or involving smaller volumes but with repetitive manipulation, and a cumbersome two-step electrophilic fluorination process. Allen, N. E. et al., *Tetrahedron*, 1989, 45, 1905-1928; Konas, D. W. and Coward, J. K., *Organic Letters*, 1999, 1(13), 2105-2107; Martinez-Montero, S. et al., *Bioorganic and Medicinal Chemistry*, 2012, 20(23), 6885-6893; and Qian, X. et al., WO 2009023193. Further intermediates and methods described herein for synthesis of difluorolactam compounds provide efficiencies comprising the incorporation chiral carbon atom centers with high stereochemical purity and facilitation of efficient attachment of functionalized organic chains.

SUMMARY OF THE INVENTION

In one aspect of the invention is provided a process of preparing a compound of formula (IA)

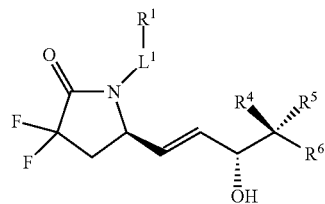

(IA)

or a pharmaceutically acceptable salt thereof wherein:
$L^1$ is
a) $C_3$-$C_7$alkylene, $C_3$-$C_7$alkenylene, or $C_3$-$C_7$alkynylene; or
b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;
$G^2$ is

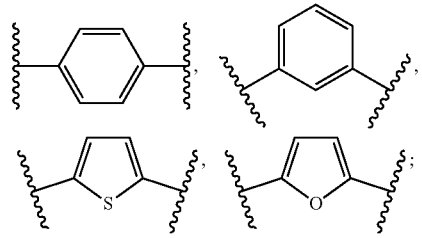

$R^1$ is a carboxylic acid or a protected carboxylic acid;
$R^{12}$, at each occurrence, is independently H or $C_1$-$C_4$alkyl;
$R^4$ and $R^5$ are each independently H or $C_1$-$C_4$ alkyl; or $R^4$ and $R^5$ together with the carbon to which they are attached form a $C_3$-$C_5$ cycloalkyl;
$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$ alkylene-$C_1$-$C_3$alkoxy;
$L^3$ is $C_1$-$C_6$alkylene, $C_2$-$C_6$alkenylene, $C_2$-$C_6$alkynylene; and
$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy;
the method comprising reacting a compound of formula (10),

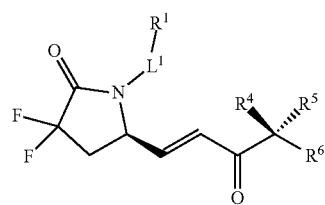

(10)

with a carbonyl-reducing agent; and when $R^1$ is a protected carboxylic acid, optionally deprotecting the protected carboxylic acid.

In another aspect of the invention is provided a process of preparing a compound of formula (10) comprising reacting a compound of formula (8) with a compound of formula (9) in the presence of a trialkylamine base and lithium chloride;

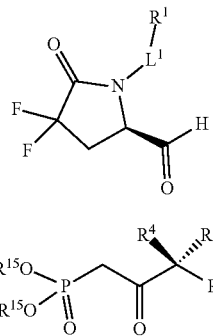
(8)

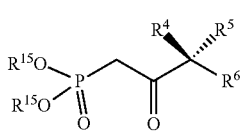
(9)

wherein:

$L^1$ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

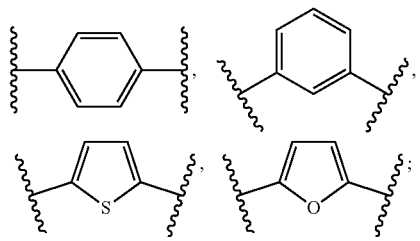

$R^1$ is a protected carboxylic acid;

$R^{12}$, at each occurrence, is independently H or $C_1$-$C_4$alkyl;

$R^4$ and $R^5$ are each independently H or $C_1$-$C_4$ alkyl; or $R^4$ and $R^5$ together with the carbon to which they are attached form a $C_3$-$C_5$ cycloalkyl;

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and $C_1$-$C_3$ alkylene-$C_1$-$C_3$alkoxy;

$L^3$ is $C_1$-$C_6$alkylene, $C_2$-$C_6$alkenylene, $C_2$-$C_6$alkynylene;

$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and $R^{15}$ is $C_1$-$C_6$alkyl.

In another aspect of the invention is provided a method of preparing a compound of formula (8), comprising reacting a compound of formula (7) with an oxidizing agent,

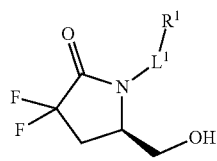
(7)

wherein:

$L^1$ is a) $C_3$-$C_7$alkylene, $C_3$-$C_7$alkenylene, or $C_3$-$C_7$alkynylene; or b) —$(CH_2)_{n1}$-$G^2$ $(CH_2)_p$—, —$(CH_2)_{n2}$—C≡C-$G^2$, or $(CH_2)_{n2}$—C($R^{12}$)—C($R^{12}$) $G^2$-, wherein n1 is 2, 3, 4, or 5, n2 is 1, 2, or 3, p is 0, 1, 2, or 3, and n1+p=2, 3, 4, 5, or 6;

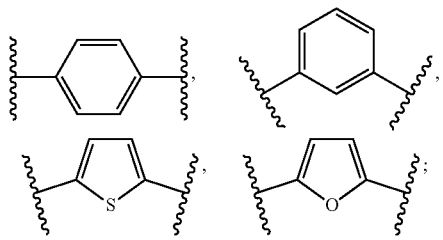

$R^1$ is a protected carboxylic acid; and $R^{12}$, at each occurrence, is independently H or $C_1$-$C_4$alkyl.

In another aspect is provided a process of preparing a compound of formula (6) comprising reacting a compound of formula (5) with a base and a compound of formula $X^1$-$L^1$-$R^1$,

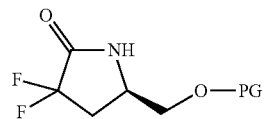
(5)

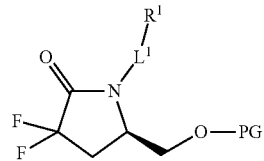
(6)

wherein:

$X^1$ is a leaving group selected from the group consisting of bromo, chloro, iodo, an alkylsulfonate, a fluoroalkylsulfonate, and an arylsulfonate;

PG is a protecting group;

$L^1$ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)C($R^2$)-$G^2$-, wherein n1 is 2, 3, 4, or 5, n2 is 1, 2, or 3, p is 0, 1, 2, or 3, and n1+p=2, 3, 4, 5, or 6;

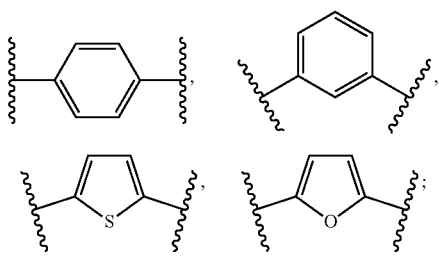

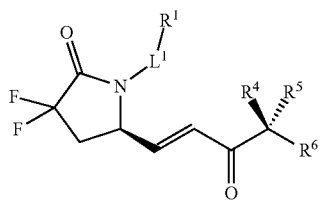

R[1] is a protected carboxylic acid; and

R[12], at each occurrence, is independently H or $C_1$-$C_4$alkyl.

In another aspect is provided a process of preparing a compound of formula (4) by reacting the compound of formula (2) with an acid, wherein R[13] is independently $C_1$-$C_3$alkyl or phenyl, or the R[13] groups, together with the carbon to which they are attached, form a $C_3$-$C_6$cycloalkyl.

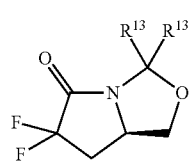

(2)

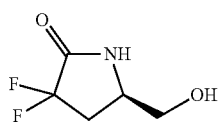

(4)

In another aspect is provided a process of preparing a compound of formula (2) from a compound of formula (1) comprising reacting a compound of formula (1) with a base and a fluorinating agent, wherein each R[13] is independently $C_1$-$C_3$alkyl or phenyl, or the R[13] groups, together with the carbon to which they are attached, form a $C_3$-$C_6$cycloalkyl.

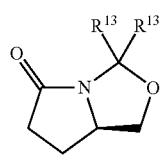

(1)

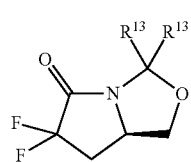

(2)

In yet another aspect is provided a compound of formula (10)

(10)

or salts thereof wherein:

L[1] is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C(R[12])=C(R[12])-$G^2$-, wherein n1 is 2, 3, 4, or 5, n2 is 1, 2, or 3, p is 0, 1, 2, or 3, and n1+p=2, 3, 4, 5, or 6;

$G^2$ is

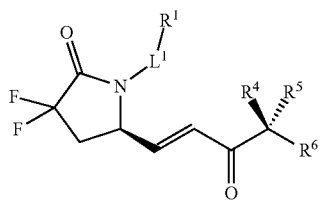

R[1] is a carboxylic acid or a protected carboxylic acid;

R[12], at each occurrence, is independently H or $C_1$-$C_4$alkyl;

R[4] and R[5] are each independently H or $C_1$-$C_4$ alkyl; or R[4] and R[5] together with the carbon to which they are attached form a $C_3$-$C_5$ cycloalkyl;

R[6] is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or L[3]-R[7]; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$ alkylene-$C_1$-$C_3$alkoxy;

L[3] is $C_1$-$C_6$alkylene, $C_2$-$C_6$alkenylene, $C_2$-$C_6$alkynylene; and

R[7] is $C_3$-$C_8$cycloalkyl, aryl, heteroaryl, or heterocyclyl; wherein R[7] is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In another aspect is provided a compound of formula (6.1)

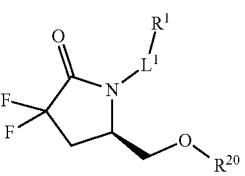

(6.1)

wherein:

L¹ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)═C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

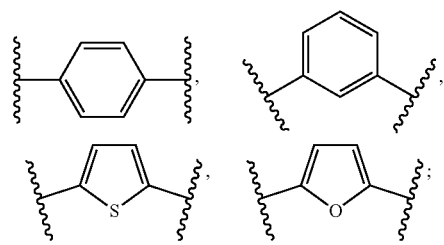

$R^1$ is a protected carboxylic acid;

$R^{12}$, at each occurrence, is independently H or $C_1$-$C_4$alkyl; and $R^{20}$ is H or a hydroxyl protecting group.

In another aspect is provided a compound of formula (2)

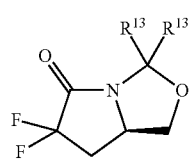

(2)

wherein each $R^{13}$ is independently $C_1$-$C_3$alkyl or phenyl, or the $R^{13}$ groups, together with the carbon to which they are attached, form a $C_3$-$C_6$cycloalkyl.

In another aspect is provided a compound of formula (9)

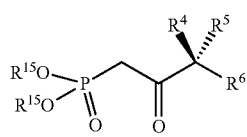

(9)

wherein:

$R^4$ and $R^5$ are each independently H or $C_1$-$C_4$ alkyl; or $R^4$ and $R^5$ together with the carbon to which they are attached form a $C_3$-$C_5$ cycloalkyl;

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$ alkylene-$C_1$-$C_3$alkoxy;

$L^3$ is $C_1$-$C_6$alkylene, $C_2$-$C_6$alkenylene, $C_2$-$C_6$alkynylene;

$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and $R^{15}$ is $C_1$-$C_6$alkyl.

In another aspect of the invention is provided a compound $X^1$-$L^1$-$R^1$, wherein:

$X^1$ is selected from the group consisting of bromo, chloro, iodo, an alkylsulfonate, a fluoroalkylsulfonate, and an arylsulfonate;

L¹ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)═C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is,

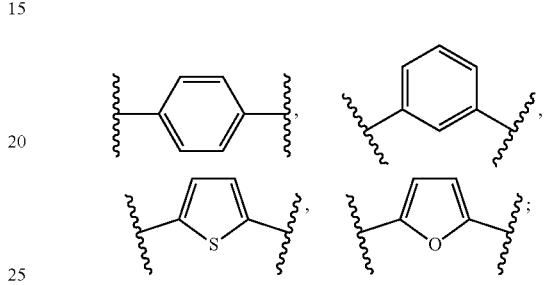

$R^1$ is a protected carboxylic acid; and $R^{12}$ is H or $C_1$-$C_4$ alkyl.

The processes of the present invention comprise steps that generate improved yields and fewer by-products than traditional methods. Many of the processes of the present invention do not require additional chromatography for purification of intermediates and generate intermediates with high stereochemical and chemical purity. The processes of the present invention are scalable for generation of commercial quantities of difluorolactam compounds.

Processes and intermediates of the invention are as shown generally in Scheme 1.

Scheme 1

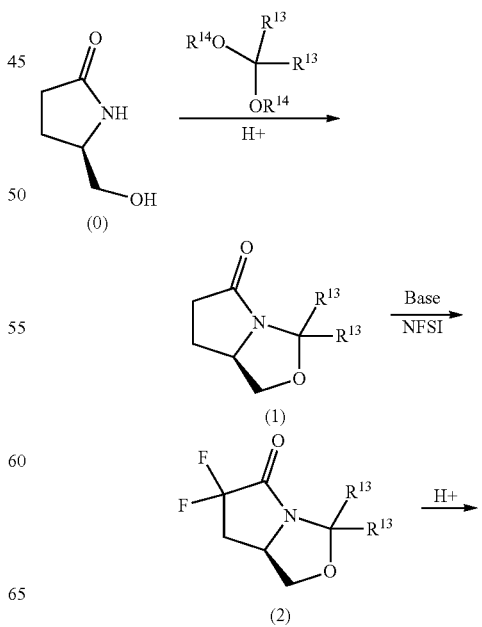

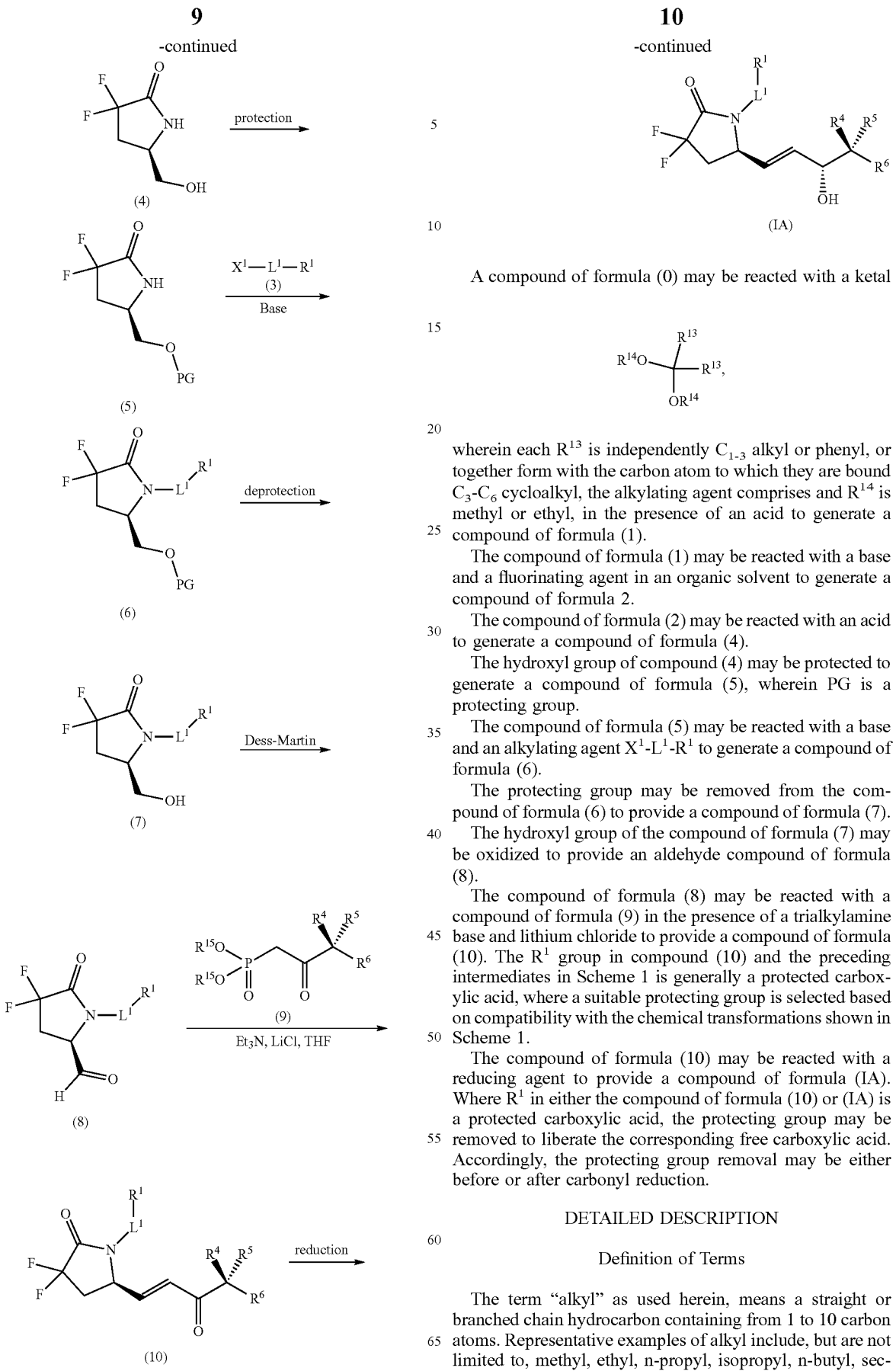

A compound of formula (0) may be reacted with a ketal wherein each $R^{13}$ is independently $C_{1-3}$ alkyl or phenyl, or together form with the carbon atom to which they are bound $C_3$-$C_6$ cycloalkyl, the alkylating agent comprises and $R^{14}$ is methyl or ethyl, in the presence of an acid to generate a compound of formula (1).

The compound of formula (1) may be reacted with a base and a fluorinating agent in an organic solvent to generate a compound of formula 2.

The compound of formula (2) may be reacted with an acid to generate a compound of formula (4).

The hydroxyl group of compound (4) may be protected to generate a compound of formula (5), wherein PG is a protecting group.

The compound of formula (5) may be reacted with a base and an alkylating agent $X^1$-$L^1$-$R^1$ to generate a compound of formula (6).

The protecting group may be removed from the compound of formula (6) to provide a compound of formula (7).

The hydroxyl group of the compound of formula (7) may be oxidized to provide an aldehyde compound of formula (8).

The compound of formula (8) may be reacted with a compound of formula (9) in the presence of a trialkylamine base and lithium chloride to provide a compound of formula (10). The $R^1$ group in compound (10) and the preceding intermediates in Scheme 1 is generally a protected carboxylic acid, where a suitable protecting group is selected based on compatibility with the chemical transformations shown in Scheme 1.

The compound of formula (10) may be reacted with a reducing agent to provide a compound of formula (IA). Where $R^1$ in either the compound of formula (10) or (IA) is a protected carboxylic acid, the protecting group may be removed to liberate the corresponding free carboxylic acid. Accordingly, the protecting group removal may be either before or after carbonyl reduction.

DETAILED DESCRIPTION

Definition of Terms

The term "alkyl" as used herein, means a straight or branched chain hydrocarbon containing from 1 to 10 carbon atoms. Representative examples of alkyl include, but are not limited to, methyl, ethyl, n-propyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkynyl," as used herein, means a straight or branched chain hydrocarbon containing from 2 to 10 carbons and containing at least one carbon-carbon triple bond. Representative examples include propynyl, butynyl, pentynyl, and the like.

The term "alkylene," as used herein, means a divalent group derived from a straight or branched chain hydrocarbon of from 1 to 10 carbon atoms. Representative examples of alkylene include, but are not limited to, —$CH_2$—, —$CH_2CH_2$—, —$CH_2CH_2CH_2$—, —$CH_2CH(CH_3)CH_2$—, and —$CH_2CH(CH_3)CH(CH_3)CH_2$—.

The term "alkenylene," as used herein, means a divalent group derived from a straight or branched chain hydrocarbon of from 2 to 10 carbon atoms and containing at least one carbon-carbon double bond. Representative examples of alkenylene include, but are not limited to —CH=CH—, —$CH_2$CH=CH—, and —$CH_2$CH=CH($CH_3$)—.

The term "alkynylene," as used herein, means a divalent group derived from a straight or branched chain hydrocarbon of from 2 to 10 carbon atoms and containing at least one carbon-carbon triple bond. Representative examples of alkynylene include, but are not limited to —$CH_2$—C≡C—, —$CH_2CH_2$—C≡C—, and —C≡C—$CH_2$CH($CH_3$)$CH_2$—.

The term "alkoxy" as used herein, means an alkyl group, as defined herein, appended to the parent molecular moiety through an oxygen atom. Representative examples of alkoxy include, but are not limited to, methoxy, ethoxy, propoxy, isopropoxy, butoxy, isobutoxy, tert-butoxy, pentyloxy, and hexyloxy.

The term "alkylcarbonyl" as used herein, means an alkyl group, as defined herein, appended to the parent molecular moiety through a C(O) group.

The term "carboxylic acid" as used herein refers to the moiety —COOH attached to the parent molecular entity.

The term "protected carboxylic acid" as used herein refers to a carboxylic acid derivative wherein the carboxylic acid is masked in the form of a less reactive functional group. Protected carboxylic acids are well known in the art and include such common derivatives as esters, orthoesters, oxazoles, 1,2-isoxazolines, thiol esters, amides, and hydrazides. Numerous esters are known as protected carboxylic acids including, but not limited to, common derivatives such as alkyl esters, benzyl esters, aryl esters, 9-fluorenylmethyl esters, methoxymethyl esters, tetrahydropyranyl esters, 2-(trimethylsilyl)ethoxymethyl esters, haloalkyl esters, silyl esters, etc. This list is not intended to be exhaustive but merely exemplary. A more extensive list of esters and other carboxylic acids protecting groups are described by T. Greene and P. Wuts in *Protective Groups in Organic Synthesis*, John Wiley & Sons, Inc., which is incorporated herein by reference in its entirety.

The terms "haloalkyl," "haloalkenyl," and "haloalkynyl" as used herein, mean, respectively an alkyl, alkenyl, or alkynyl group, as defined herein, in which one, two, three, four, five, six, or seven hydrogen atoms are replaced by halogen. For example, representative examples of haloalkyl include, but are not limited to, 2-fluoroethyl, 2,2-difluoroethyl, trifluoromethyl, 2,2,2-trifluoroethyl, 2,2,2-trifluoro-1,1-dimethylethyl, and the like.

The term "haloalkoxy," as used herein, means an alkoxy group, as defined herein, in which one, two, three, four, five, or six hydrogen atoms are replaced by halogen. Representative examples of haloalkoxy include, but are not limited to, trifluoromethoxy, difluoromethoxy, 2,2,2-trifluoroethoxy, 2,2-difluoroethoxy, 2-fluoroethoxy, and pentafluoroethoxy.

The term "aryl," as used herein, means phenyl or a bicyclic aryl. The bicyclic aryl is naphthyl, dihydronaphthalenyl, tetrahydronaphthalenyl, indanyl, or indenyl. The phenyl and bicyclic aryls are attached to the parent molecular moiety through any carbon atom contained within the phenyl or bicyclic aryl.

The term "heteroaryl," as used herein, means a monocyclic heteroaryl or a fused bicyclic heteroaryl. The monocyclic heteroaryl is a 5 or 6 membered ring containing at least one heteroatom independently selected from the group consisting of O, N, and S. The 5-membered ring contains two double bonds, and one, two, three, or four heteroatoms as ring atoms. The 6-membered ring contains three double bonds, and one, two, three or four heteroatoms as ring atoms. Representative examples of monocyclic heteroaryl include, but are not limited to, furanyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl is an 8- to 12-membered ring system having a monocyclic heteroaryl fused to an additional ring; wherein the additional ring may be aromatic or partially saturated, and may contain additional heteroatoms. Representative examples of bicyclic heteroaryl include, but are not limited to, benzofuranyl, benzoxadiazolyl, 1,3-benzothiazolyl, benzimidazolyl, benzodioxolyl, benzothienyl, chromenyl, furopyridinyl, indolyl, indazolyl, isoquinolinyl, naphthyridinyl, oxazolopyridine, quinolinyl, thienopyridinyl, 5,6,7,8-tetrahydroquinolinyl, 6,7-dihydro-5H-cyclopenta[b]pyridinyl, and 2,3-dihydrofuro[3,2-b]pyridinyl. The monocyclic and the bicyclic heteroaryl groups are connected to the parent molecular moiety through any substitutable carbon atom or any substitutable nitrogen atom contained within the groups.

The term "cycloalkyl" as used herein, means a carbocyclic ring system containing 3, 4, 5, 6, 7, or 8 carbon atoms and zero heteroatoms as ring atoms, and zero double bonds. Examples of cycloalkyls include, but are not limited to, cyclopropyl, cyclobutyl, cyclopentyl, cyclohexyl, cycloheptyl, and cyclooctyl. The cycloalkyl groups of the present invention may contain an alkylene bridge of 1, 2, 3, or 4 carbon atoms, linking two non adjacent carbon atoms of the group. Examples of such bridged systems include, but are not limited to, bicyclo[2.2.1]heptanyl and bicyclo[2.2.2]octanyl. The cycloalkyl groups described herein can be appended to the parent molecular moiety through any substitutable carbon atom.

The term "heterocycle" or "heterocyclic" as used herein, refers to a monocyclic heterocycle, a bicyclic heterocycle, or a spirocyclic heterocycle. The monocyclic heterocycle is a 3, 4, 5, 6, 7, or 8-membered ring containing at least one heteroatom selected from O, N, or S. The 3 or 4 membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, aziridinyl, diazepanyl, 1,3-dioxanyl, 1,4-dioxanyl, 1,3-dioxolanyl, 4,5-dihydroisoxazol-5-yl, 3,4- dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The bicyclic heterocycle is a 5-12-membered ring system having a monocyclic heterocycle fused to a phenyl, a saturated or partially saturated carbocyclic ring, or another monocyclic heterocyclic ring. Representative examples of bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, and 1,2,3,4-tetrahydroquinolinyl. Spirocyclic heterocycle means a 4-, 5-, 6-, 7-, or 8-membered monocyclic heterocycle ring wherein two of the substituents on the same carbon atom form a 3-, 4-, 5-, or 6-membered monocyclic ring selected from the group consisting of cycloalkyl and heterocycle, each of which is optionally substituted with 1, 2, 3, 4, or 5 alkyl groups. Examples of a spiroheterocycle include, but are not limited to, 5-oxaspiro[3,4]octane and 8-azaspiro[4.5]decane. The monocyclic and bicyclic heterocycle groups of the present invention may contain an alkylene bridge of 1, 2, 3, or 4 carbon atoms, linking two non-adjacent atoms of the group. Examples of such a bridged heterocycle include, but are not limited to, 2-azabicyclo[2.2.1]heptanyl, 2-azabicyclo[2.2.2]octanyl, 1,2,3,4-tetrahydro-1,4-methanoisoquinolinyl, and oxabicyclo[2.2.1]heptanyl. The monocyclic, bicyclic, and spirocyclic heterocycle groups are connected to the parent molecular moiety through any substitutable carbon atom or any substitutable nitrogen atom contained within the group.

Terms such as "alkyl," "cycloalkyl," "alkylene," etc. may be preceded by a designation indicating the number of atoms present in the group in a particular instance (e.g., "$C_3$-$C_{10}$alkyl," "$C_3$-$C_{10}$cycloalkyl," "$C_2$-$C_6$alkynylene," "$C_2$-$C_6$alkenylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_3$-$C_{10}$," the members of the group that follows may have any number of carbon atoms falling within the recited range. A "$C_3$-$C_{10}$alkyl," for example, is an alkyl group having from 3 to 10 carbon atoms, however arranged.

Methods of Preparation

In a first aspect of the invention is provided a process of preparing a compound of formula (IA), or a pharmaceutically acceptable salt thereof, by reacting a compound of formula (10) with a carbonyl-reducing agent; and when $R^1$ is a protected carboxylic acid, optionally deprotecting the protected carboxylic acid.

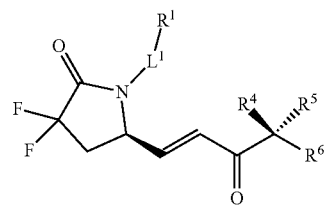

(10)

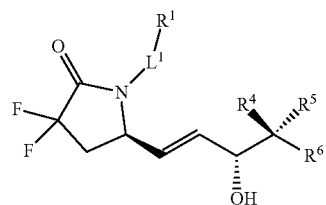

(IA)

In one embodiment according to the first aspect is a process of preparing a group of compounds of formula (IA) wherein:

$L^1$ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

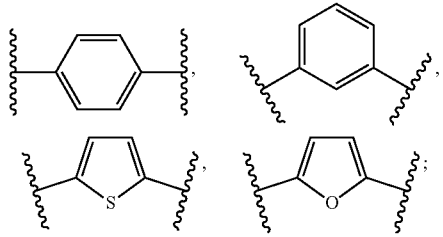

$R^1$ is a carboxylic acid or a protected carboxylic acid;

$R^{12}$, at each occurrence, is independently H or $C_1$-$C_4$alkyl;

$R^4$ and $R^5$ are each independently H or $C_1$-$C_4$ alkyl; or $R^4$ and $R^5$ together with the carbon to which they are attached form a $C_3$-$C_5$ cycloalkyl;

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$ alkylene-$C_1$-$C_3$alkoxy;

$L^3$ is $C_1$-$C_6$alkylene, $C_2$-$C_6$alkenylene, $C_2$-$C_6$alkynylene; and $R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$ alkoxy.

In another embodiment of the first aspect is a process of preparing a group of compounds of formula (IA) wherein $R^1$ and $L^3$ are as defined above and:

$L^1$ is n-hexylene, —(CH$_2$)$_3$-G$^2$-, —CH$_2$—C≡C-G$^2$-, or —CH$_2$—C(H)=C(H)-G$^2$-;

$G^2$ is

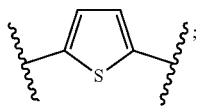

$R^4$ and $R^5$ are each independently H or $C_1$-$C_4$ alkyl;

$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and $R^7$ is phenyl, which is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In another embodiment of the first aspect is a process of preparing a subgroup of compounds of formula (IA) wherein $R^1$ is as defined above and:

$L^1$ is —(CH$_2$)$_3$-G$^2$-;

$G^2$ is

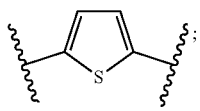

$R^4$ and $R^5$ are each independently H or methyl;

$R^6$ is —CH$_2$—C≡C—$C_1$-$C_4$alkyl or $L^3$-$R^7$;

$L^3$ is $C_3$-$C_6$alkylene; and $R^7$ is phenyl.

According to the preceding subgroup are processes for preparing further subgroups of compounds of formula (IA) wherein either $R^4$ is methyl and $R^5$ is H or H and $R^5$ is methyl.

In some implementations, the carbonyl reducing agent is an asymmetric reducing agent such as the (R)-Corey-Bakshi-Shibata catalyst ((R)-CBS)

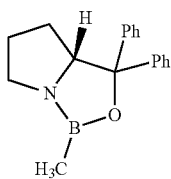

and catechol borane.

Deprotection of a protected carboxylic acid may be by any appropriate method described in Greene and Wuts, or other methods well known to those skilled in the art for the particular protecting group. For example, hydrolysis is a common method of converting a protected carboxylic acid (e.g., an ester) to a carboxylic acid. Thus, in some implementations, the optional deprotection is by hydrolysis of an ester. The particular deprotection method is selected according to the requirements of the particular protecting group and other functionality present in the molecule.

According to the foregoing embodiments are also provided processes for preparing the compound of formula (10), wherein $L^1$, $R^4$, $R^5$, $R^6$ and $R^{15}$ are as defined herein and $R^1$ is a protected carboxylic acid, by reacting a compound of formula (8) with a compound of formula (9) in the presence of a trialkylamine base and lithium chloride.

In some implementations, the trialkylamine base is triethylamine (TEA) or diisopropylethylamine (DIEA; also known as "Hünig's base"). For example, the trialkylamine base is triethylamine. In some implementations, the organic solvent is an ether solvent. For example, the organic solvent is THF.

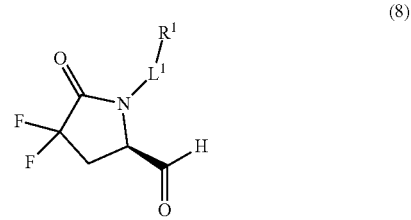

(8)

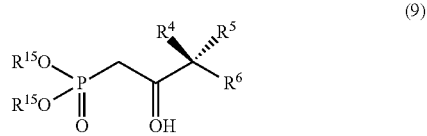

(9)

Further according to the foregoing embodiments are provided processes of preparing the compound of formula (8), wherein $L^1$ is as defined herein and $R^1$ is a protected carboxylic acid, by reacting a compound of formula (7) with an oxidizing agent in an organic solvent. In some implementations, the oxidizing agent comprises Dess-Martin periodinane and the organic solvent comprises a halogenated solvent such as dichloromethane (DCM), chloroform, or 1,2-dichloroethane (DCE). For example, the oxidizing agent comprises Dess-Martin periodinane and the organic solvent comprises DCM.

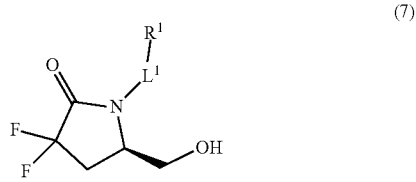

(7)

Also provided according to the foregoing embodiments are processes of preparing the compound of formula (7), wherein $L^1$ is as defined herein and $R^1$ is a protected carboxylic acid, by removing a protecting group PG from a compound of formula (6). In certain implementations, PG is —Si($R^{21}$)$_3$, 1-ethoxyethyl, or tetrahydro-2H-pyran-2-yl; and $R^{21}$, at each occurrence, is independently selected from $C_1$-$C_4$alkyl and phenyl.

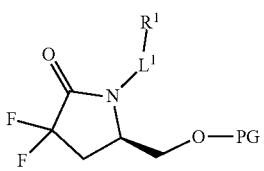

(6)

In some implementations the removal of the protecting group PG comprises reacting the compound of formula (6) with an acid in the presence of an organic solvent. For example, the acid comprises TsOH and the organic solvent comprises methanol. For another example, the acid comprises camphor sulfonic acid (CSA) and the organic solvent comprises methanol. In certain implementations, wherein the PG of the compound of formula (6) is a silyl protecting group, the deprotection step comprises reacting the compound of formula (6) with a reagent comprising fluoride ion, such as tert-butylammonium fluoride (TBAF), pyridinium fluoride, sodium fluoride, potassium fluoride, or cesium fluoride, and an organic solvent. For example, the reagent comprising fluoride ion comprises TBAF and the organic solvent comprises THF.

Also provided are processes of preparing the compound of formula (6), wherein $L^1$ and PG are as defined herein and $R^1$ is a protected carboxylic acid, by reacting a compound of formula (5) with a base and a compound of formula $X^1$-$L^1$-$R^1$ in an organic solvent to produce the compound of formula (6), wherein $X^1$ is a leaving group selected from the group consisting of bromo, chloro, iodo, an alkylsulfonate, a fluoroalkylsulfonate, and an arylsulfonate. Suitable bases include, but are not limited to, lithium hydride, sodium hydride, and potassium hydride.

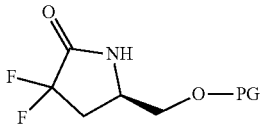

(5)

As explained above, in some implementations, the leaving group $X^1$ of $X^1$-$L^1$-$R^1$ comprises a halide. For example, $X^1$ is Br or I. In some implementations, the leaving group comprises a sulfonate. For example, $X^1$ is para-toluenesulfonate (tosylate), benzenesulfonate, para-nitrobenzenesulfonate (nosylate), para-bromobenzenesulfonate (brosylate), trifluoromethanesulfonate (triflate), or methanesulfonate (mesylate).

In some implementations, the $L^1$ of $X^1$-$L^1$-$R^1$ comprises a $C_3$-$C_7$ alkylene group. For example, $L^1$ is hexylene. In some implementations, the $L^1$ of $X^1$-$L^1$-$R^1$ comprises a $C_3$-$C_7$ alkenylene group. For example, X-$L^1$-$R^1$ is

In some implementations, the $L^1$ of X-$L^1$-$R^1$ comprises a $C_3$-$C_7$ alkynylene group. For example, $X^1$-$L^1$-$R^1$ is

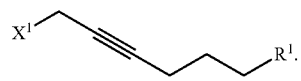

In some implementations, the $L^1$ of $X^1$-$L^1$-$R^1$ comprises —$(CH_2)_n$-$G^2$-, wherein $G^2$ is

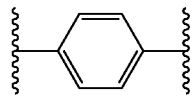

and n is 2, or wherein $G^2$ is

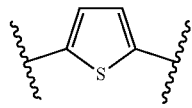

and n is 3. For example, $X^1$-$L^1$-$R^1$ is

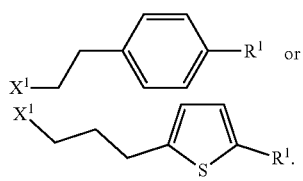

In some implementations, $X^1$-$L^1$-$R^1$ comprises a compound of formula (24)

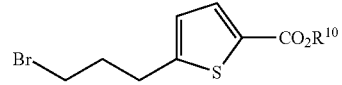

(24)

wherein $R^{10}$ is methyl, the base comprises an alkali hydride such as lithium hydride, sodium hydride, or potassium hydride, and the organic solvent comprises DMF or dimethylacetamide (DMA). In some further implementations, the reaction mixture to prepare the compound of formula (6) may include an alkali iodide such as sodium iodide, potassium iodide, or cesium iodide.

Also provided are processes of preparing the compound of formula (5) by adding a protecting group PG to a compound of formula (4). PG may be —Si($R^{21}$)$_3$, 1-ethoxyethyl, or tetrahydro-2H-pyran-2-yl; and $R^{21}$, at each occurrence, is independently selected from $C_1$-$C_4$alkyl and phenyl.

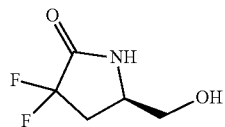

(4)

In some implementations, the hydroxyl group protection comprises reacting the compound of formula (4) with a silylating agent such as chlorotrimethylsilane (TMSCl), tert-butyldimethylsilyl chloride (TBDMSCl), tert-butylchlorodiphenylsilane (TBDPSCl), or triisopropylsilyl chloride (TIPSCl) in the presence of a base and an organic solvent. For example, the silylating agent of step comprises TBDMSCl, the base comprises imidazole, and the organic solvent comprises N,N-dimethylformamide (DMF).

In some implementations, the hydroxyl group protection comprises reacting the compound of formula (4) with a vinyl ether such as ethyl vinyl ether (EVE) or 3,4-dihydro-2H-pyran (DHP) in the presence of an acid and an organic solvent. For example, the vinyl ether comprises EVE, the acid comprises TsOH, and the organic solvent comprises THF. For another example, the vinyl ether comprises DHP, the acid comprises TsOH, and the organic solvent comprises THF.

In a second aspect of the invention is provided a process of preparing a compound of formula (10) comprising reacting a compound of formula (8) with a compound of formula (9) in the presence of a trialkylamine base and lithium chloride;

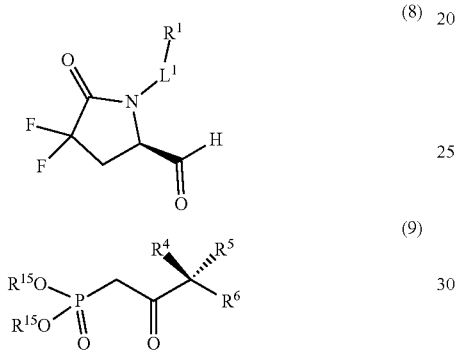

(8)

(9)

In one embodiment according to the second aspect is a process of preparing a group of compounds of formula (10) wherein:
$L^1$ is
a) $C_3$-$C_7$alkylene, $C_3$-$C_7$alkenylene, or $C_3$-$C_7$alkynylene; or
b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;
$G^2$ is

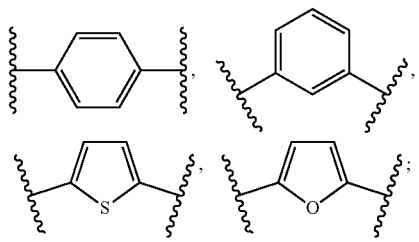

$R^1$ is a protected carboxylic acid;
$R^{12}$, at each occurrence, is independently H or $C_1$-$C_4$alkyl;
$R^4$ and $R^5$ are each independently H or $C_1$-$C_4$ alkyl; or $R^4$ and $R^5$ together with the carbon to which they are attached form a $C_3$-$C_5$ cycloalkyl;
$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$ alkylene-$C_1$-$C_3$alkoxy;
$L^3$ is $C_1$-$C_6$alkylene, $C_2$-$C_6$alkenylene, $C_2$-$C_6$alkynylene;
$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and
$R^{15}$ is $C_1$-$C_6$alkyl.

In another embodiment is a process of preparing a subgroup of compounds of formula (10) wherein $R^1$ and $L^3$ are as defined above and:
$L^1$ is n-hexylene, —$(CH_2)_3$-$G^2$-, —$CH_2$—C≡C-$G^2$-, or —$CH_2$—C(H)=C(H)-$G^2$-;
G is

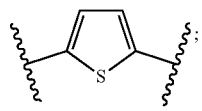 [SMILES: *c1ccc(*)s1]

$R^4$ and $R^5$ are each independently H or $C_1$-$C_4$ alkyl;
$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and
$R^7$ is phenyl, which is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In another embodiment is a process of preparing a subgroup of compounds of formula (10) wherein $R^1$ and $G^2$ are as defined above and:
$L^1$ is —$(CH_2)_3$-$G^2$-;
$R^4$ and $R^5$ are each independently H or methyl;
$R^6$ is —$CH_2$—C≡C—$C_1$-$C_4$alkyl or $L^3$-$R^7$;
$L^3$ is $C_3$-$C_6$alkylene; and
$R^7$ is phenyl.

Also provided according to the foregoing embodiments are processes of preparing the compounds of formula (8), (7), (6), and (5) as described herein above.

In a third aspect of the invention is provided a method of preparing a compound of formula (8), comprising reacting a compound of formula (7) with an oxidizing agent in an organic solvent. In one embodiment according to the third aspect is a process of preparing a group of compounds of formula (8) wherein:
$L^1$ is
a) $C_3$-$C_7$alkylene, $C_3$-$C_7$alkenylene, or $C_3$-$C_7$alkynylene; or
b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;
$G^2$ is

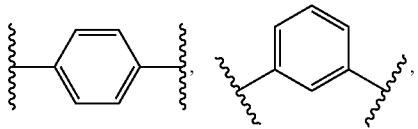

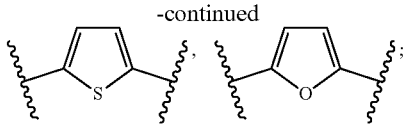

R$^1$ is a protected carboxylic acid; and
R$^{12}$, at each occurrence, is independently H or C$_1$-C$_4$alkyl.

In another embodiment according to the third aspect is a process of preparing a subgroup of compounds of formula (8) wherein:
R$^1$ is a protected carboxylic acid;
L$^1$ is n-hexylene, —(CH$_2$)$_3$-G$^2$-, —CH$_2$—C≡C-G$^2$-, or —CH$_2$—C(H)═C(H)-G$^2$-; and
G$^2$ is

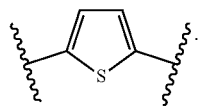 [SMILES: *c1ccc(*)s1]

In another embodiment according to the third aspect is a process of preparing a subgroup of compounds of formula (8) wherein G$^2$ is as defined above and:
R$^1$ is a protected carboxylic acid; and
L$^1$ is —(CH$_2$)$_3$-G$^2$-.

In one implementation, the oxidizing agent is Dess-Martin periodinane.

Also provided according to the foregoing embodiments are processes of preparing the compounds of formula (7), (6), and (5) as described herein above.

In a fourth aspect is provided a process of preparing a compound of formula (6) comprising reacting a compound of formula (5) with a base and a compound of formula X$^1$-L$^1$-R$^1$.

In one embodiment according to the fourth aspect is a process of preparing a group of compounds of formula (6) wherein:
X$^1$ is a leaving group selected from the group consisting of bromo, chloro, iodo, an alkylsulfonate, a fluoroalkylsulfonate, and an arylsulfonate;
PG is a protecting group;
L$^1$ is
a) C$_3$-C$_7$alkylene, C$_3$-C$_7$alkenylene, or C$_3$-C$_7$alkynylene; or
b) —(CH$_2$)$_{n1}$-G$^2$-(CH$_2$)$_p$—, —(CH$_2$)$_{n2}$—C≡C-G$^2$-, or —(CH$_2$)$_{n2}$—C(R$^2$)═C(R$^{12}$)-G$^2$-, wherein n1 is 2, 3, 4, or 5, n2 is 1, 2, or 3, p is 0, 1, 2, or 3, and n1+p=2, 3, 4, 5, or 6;
G$^2$ is

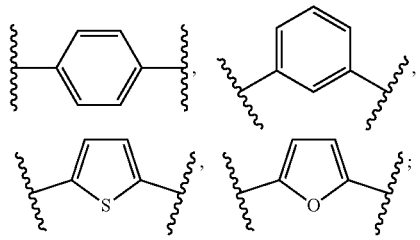

R$^1$ is a protected carboxylic acid and
R$^{12}$, at each occurrence, is independently H or C$_1$-C$_4$alkyl.

In another embodiment according to the fourth aspect is a process of preparing a subgroup of compounds of formula (6) wherein:
L$^1$ is n-hexylene, —(CH$_2$)$_3$-G$^2$-, —CH$_2$—C≡C-G$^2$-, or —CH$_2$—C(H)═C(H)-G$^2$-;
G$^2$ is

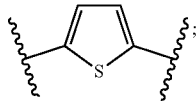

R$^1$ is a protected carboxylic acid
PG is —Si(R$^{21}$)$_3$, 1-ethoxyethyl, or tetrahydro-2H-pyran-2-yl; and
R$^{21}$, at each occurrence, is independently selected from C$_1$-C$_4$alkyl and phenyl.

In another embodiment according to the fourth aspect is a process of preparing a subgroup of compounds of formula (6) wherein R$^1$, G$^2$ and R$^{21}$ are as defined above and:
L$^1$ is —(CH$_2$)$_3$-G$^2$-; and
PG is —Si(R$^{21}$)$_3$.

Reagents and materials for preparing the foregoing groups and subgroups of compounds of formula (6) from compounds of formula (5) and compounds of formula X$^1$-L$^1$-R$^1$ are as described generally herein.

In a fifth aspect is provided a process of preparing a compound of formula (4) by reacting the compound of formula (2) with an acid, wherein R$^{13}$ is independently C$_1$-C$_3$alkyl or phenyl, or the R$^{13}$ groups, together with the carbon to which they are attached, form a C$_3$-C$_6$cycloalkyl.

In some implementations, the compound of formula (2) is reacted with an organic acid, such as for example acetic acid and the reaction is conducted in a solvent such as acetonitrile. Alternatively, (2) may be reacted with acetic acid in a mixture of acetonitrile and water.

In some implementations, the compound of formula (2) may be reacted with an acidic cation exchange resin to produce the compound of formula (4). For example, the acidic cation exchange resin may be Amberlite® IR-120 H and the reaction may be conducted in a solvent such as, for example, 1,4-dioxane. In another example, the acid of may be Amberlite® IR-120 H and the solvent may be a mixture of 1,4-dioxane and water.

In a sixth aspect is provided a process of preparing a compound of formula (2) from a compound of formula (1) comprising reacting a compound of formula (1) with a base and a fluorinating agent, wherein each R$^{13}$ is independently C$_1$-C$_3$alkyl or phenyl, or the R$^{13}$ groups, together with the carbon to which they are attached, form a C$_3$-C$_6$cycloalkyl.

In some implementations, reacting a compound of formula (1) with a base and a fluorinating agent comprises reacting the compound of formula (1) with a first base and a fluorinating agent and a second base and a fluorinating agent. In some implementations, the base is an organolithium base. The organolithium base may, in turn, be a lithium amide base. For example, the organolithium base may be a bis(trialkylsilyl)amide such as bis(trimethylsilyl)amide (LiHMDS) or a lithium dialkylamide such as lithium diisopropylamide (LDA).

For example, in some implementations the compound of formula (1) may be reacted by the sequential addition of: i) about one molar equivalent of a lithium amide base; ii) about one molar equivalent of N-fluorobenzene sulfonamide (NFSI); iii) about one molar equivalent of a lithium amide base; and iv) about one molar equivalent of NFSI. For example, the lithium amide base of step i) of the four-step sequence may be 0.9-1.1 molar equivalents of LiHMDS or LDA and the lithium amide base of step iii) may be 0.9-1.1 molar equivalents of LiHMDS or LDA. The reaction sequence may be conducted in one reaction vessel.

In another exemplary implementation, the compound of formula (1) may be reacted with: i) about one molar equivalent of an alkyllithium base, ii) about one molar equivalent of NFSI, iii) about one molar equivalent of a lithium amide base, and iv) about one molar equivalent of NFSI. For example, the alkyllithium base of step i) of the four-step sequence comprises 0.9-1.1 molar equivalents of sec-butyllithium and the lithium amide base of step iii) of the four-step sequence comprises 0.9-1.1 molar equivalents of LiHMDS or LDA.

Thus, in one exemplary implementation, the compound of formula (1) is reacted to produce the compound of formula (2) by the sequence of: (i) adding a solution of sec-butyl lithium in an organic solvent to a solution of the compound of formula (1) in an organic solvent to produce a first reaction mixture; (ii) adding N-fluorobenzene sulfonimide to the first reaction mixture to produce a second reaction mixture; (iii) adding a solution of a base selected from the group consisting of lithium bis(trimethylsilyl)amide, sodium bis(trimethylsilyl)amide, potassium bis(trimethylsilyl)amide, and lithium diisopropylamide, in an organic solvent to the second reaction mixture to produce a third reaction mixture; and (iv) adding N-fluorobenzene sulfonimide to the third reaction mixture.

In the foregoing implementations of the reaction of (1) to produce (2), the reactions may be conducted in organic solvents such as tetrahydrofuran (THF), 1,4-dioxane, diethyl ether, 1,2-dimethoxyethane (DME), or methyl tert-butyl ether (MTBE) or any combination thereof. For example, in one preferred implementation, the organic solvent includes THF.

Also provided according to the foregoing aspect of the invention is a process of preparing the compound of formula (1) from a compound of formula (0) by reaction with a compound of formula

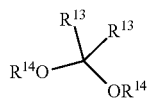

in the presence of an acid, wherein each $R^{13}$ is independently $C_1$-$C_3$alkyl or phenyl, or the $R^{13}$ groups, together with the carbon to which they are attached, form a $C_3$-$C_6$cycloalkyl; and $R^{14}$ is methyl or ethyl. In some implementations, the acid comprises camphorsulfonic acid (CSA), p-toluenesulfonic acid (TsOH), or trifluoroacetic acid (TFA). Thus, in some implementations, the compound of formula

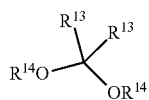

comprises 2,2-dimethoxypropane and the acid comprises camphorsulfonic acid.

Synthesis of Compounds of Formula (9)

Compounds of formula (9), wherein $R^4$ is $C_1$-$C_4$alkyl, $R^5$ is hydrogen, $R^6$ is as defined herein, may be prepared according to the sequence described here below. A carboxylic acid of formula (12) may be converted to the corresponding acid chloride (13) by reaction with, for example, oxalyl chloride and DMF in the presence of dichloromethane.

(12)

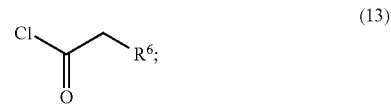

(13)

A compound of formula (14) may be converted to the corresponding lithium salt (15) by reaction with an alkyllithium base in the presence of an organic solvent.

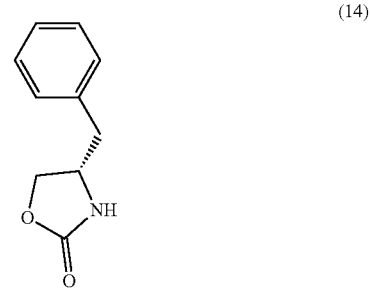

(14)

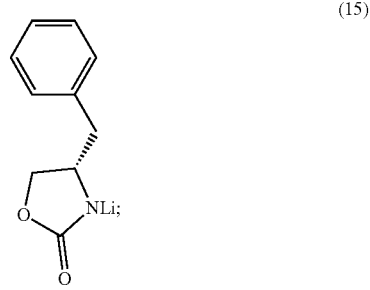

(15)

Reaction of the compound of formula (13) with the compound of formula (15) in an ether solvent at a temperature below −70° C. generates a compound of formula (16).

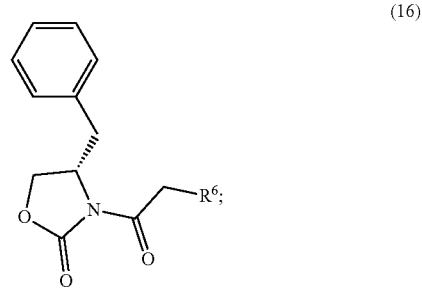

(16)

Reaction of the compound of formula (16) with an alkylating agent $R^4$—$X^1$, wherein $R^4$ is $C_1$-$C_4$ alkyl and $X^1$ is as defined above, in the presence of lithium amide base and an organic solvent generates a compound of formula (17). In some implementations, the lithium amide base comprises a bis(trialkylsilyl)amide such as LiHMDS or a lithium dialkylamide such as LDA. For example, the lithium amide base comprises LiHMDS. In some implementations, the organic solvent comprises an ether solvent. For example, the organic solvent comprises THF.

(17)

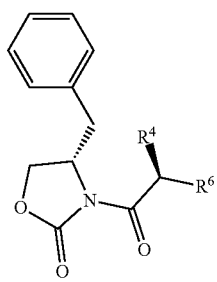

Reaction of the compound of formula (17) with a mixture comprising hydrogen peroxide, lithium hydroxide, and water generates a compound of formula (18).

(18)

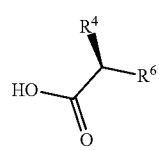

The compound of formula (18) may be converted to a compound of formula (9) by conversion of (18) to the corresponding alkyl ester and reaction with the anion of a reagent like dimethyl methyl phosphonate.

Some methods further include converting (18) to (20) by reaction with a mixture comprising N-hydroxysuccinimide (NHS), a coupling agent, a base, and an organic solvent.

(20)

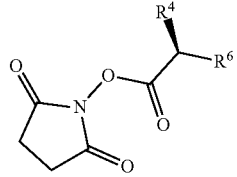

Compound (20) may be transformed to a compound of formula (21) by reaction with (R)-(-)-2-phenyl glycerol.

(21)

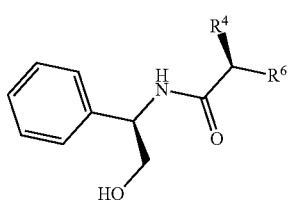

The compound of formula (21) may be purified by silica gel column chromatography to generate a purified compound of formula (21) having an enantiomeric excess (e. e.) of greater than 98% and a diastereomeric excess (d. e.) of greater than 98%. The stereochemical purity of compound (21) may also be improved by recrystallization. The recrystallization may be in addition to or instead of silica gel chromatography.

The purified compound of formula (21) may be converted to the compound of formula (9) by hydrolysis to the carboxylic acid (i.e., (18)) with 3N $H_2SO_4$ in 1,4-dioxane at 80° C., esterification of the carboxylic acid with EtOH/$H_2SO_4$, and reaction with the anion of dimethyl methylphosphonate as described above. The process described above from (18) to (21) and back to (18) may also be conducted using the racemic acid, instead of the enantiomer (18).

Synthesis of Compounds of Formula (24)

Some methods where the -$L^1$-$R^1$ of the compound of formula (IA) comprises

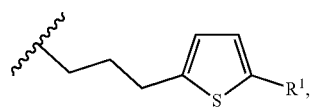

wherein $R^1$ is $COOR^{10}$, further comprise the steps of: reacting a compound of formula (21) with a compound of formula (22) in the presence of a base and an organic solvent to generate a compound of formula (23); and (21)

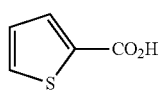

(22)

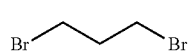

(23)

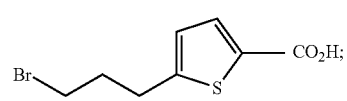

esterification of the compound of formula (23) to a compound of formula (24)

(24)

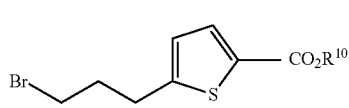

wherein $R^{10}$ is $C_1$-$C_4$ alkyl; and converting the compound of formula (24) to the compound of formula (6). In some implementations, the base used in the conversion of (21) and (22) to (23) may be a lithium amide base. For example, the base may be a bis(trialkylsilyl)amide such as LiHMDS or a lithium dialkylamide such as LDA. In some implementations, the organic solvent may be an ether solvent. For example, the organic solvent of comprises THF.

Compounds of the Invention

In another aspect is provided a compound of formula (10)

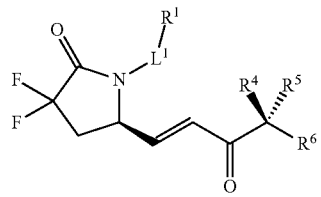

(10)

or salts thereof wherein:

$L^1$ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

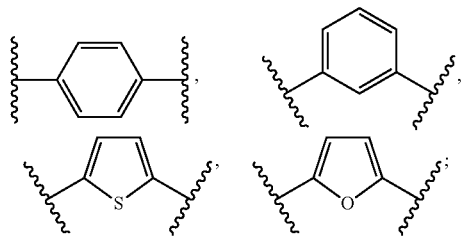

$R^1$ is a carboxylic acid or a protected carboxylic acid;

$R^{12}$, at each occurrence, is independently H or $C_1$-$C_4$alkyl;

$R^4$ and $R^5$ are each independently H or $C_1$-$C_4$ alkyl; or $R^4$ and $R^5$ together with the carbon to which they are attached form a $C_3$-$C_5$ cycloalkyl;

$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy;

$L^3$ is $C_1$-$C_6$alkylene, $C_2$-$C_6$alkenylene, $C_2$-$C_6$alkynylene; and $R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$ alkoxy.

In one embodiment according to this aspect is provided a group of compounds of formula (10) wherein $R^1$ and $L^3$ are as defined herein above and:

$L^1$ is n-hexylene, —$(CH_2)_3$-$G^2$-, —$CH_2$—C≡C-$G^2$-, or —$CH_2$—C(H)=C(H)-$G^2$-;

$G^2$ is

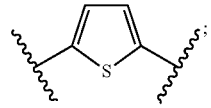 [SMILES: *c1ccc(*)s1]

$R^4$ and $R^5$ are each independently H or $C_1$-$C_4$ alkyl;

$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and $R^7$ is phenyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

In another embodiment according to this aspect is provided a subgroup of compounds of formula (10) wherein $R^1$ and $G^2$ are defined herein above and:

$L^1$ is —$(CH_2)_3$-$G^2$-;

$R^4$ is methyl;

$R^5$ is hydrogen;

$R^6$ is —$CH_2$—C≡C—$C_1$-$C_4$alkyl or $L^3$-$R^7$;

$L^3$ is $C_3$-$C_6$alkylene; and $R^7$ is phenyl.

In another embodiment according to this aspect is provided a subgroup of compounds of formula (10) wherein $R^1$ and $G^2$ are defined herein above and:

$L^1$ is —$(CH_2)_3$-$G^2$-;

$R^4$ is hydrogen;

$R^5$ is methyl;

$R^6$ is —$CH_2$—C≡C—$C_1$-$C_4$alkyl or $L^3$-$R^7$;

$L^3$ is $C_3$-$C_6$alkylene; and $R^7$ is phenyl.

In another aspect is provided a compound of formula (6.1)

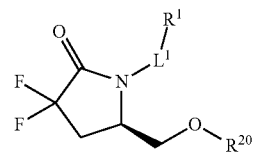

(6.1)

wherein:

$L^1$ is a) $C_3$-$C_7$alkylene, $C_3$-$C_7$alkenylene, or $C_3$-$C_7$alkynylene; or b) —$(CH_2)_{n1}$-$G^2$-$(CH_2)_p$—, —$(CH_2)_{n2}$—C≡C-$G^2$-, or —$(CH_2)_n2$-C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

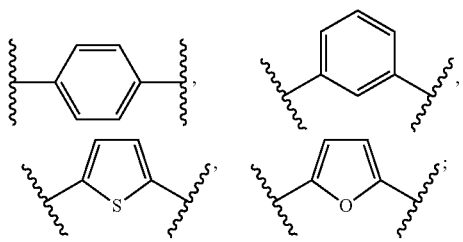

$R^1$ is a protected carboxylic acid;
$R^{12}$, at each occurrence, is independently H or $C_1$-$C_4$alkyl; and
$R^{20}$ is H or a hydroxyl protecting group.

In one embodiment according to this aspect is provided a group of compounds of formula (6.1) wherein:
$R^1$ is a protected carboxylic acid;
$L^1$ is n-hexylene, —(CH$_2$)$_3$-G$^2$-, —CH$_2$—C≡C-G$^2$-, or —CH$_2$—C(H)=C(H)-G$^2$-;
$G^2$ is

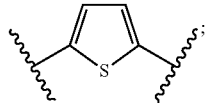 [SMILES: *c1ccc(*)s1]

$R^{20}$ is H, —Si(R$^{21}$)$_3$, 1-ethoxyethyl, or tetrahydro-2H-pyran-2-yl; and
$R^{21}$, at each occurrence, is independently selected from $C_1$-$C_4$alkyl and phenyl.

In another embodiment according to this aspect is provided a further subgroup of compounds of formula (6.1) wherein $R^1$, $G^2$, $R^{20}$, and $R^{21}$ are as defined above and:
$L^1$ is —(CH$_2$)$_3$-G$^2$-.

In another aspect is provided a compound of formula (2)

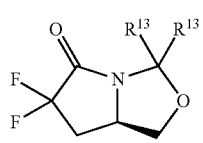

(2)

wherein each $R^{13}$ is independently $C_1$-$C_3$alkyl or phenyl, or the $R^{13}$ groups, together with the carbon to which they are attached, form a $C_3$-$C_6$cycloalkyl.

In one embodiment of this aspect is a compound where $R^{13}$ is methyl.

In another aspect is provided a compound of formula (9)

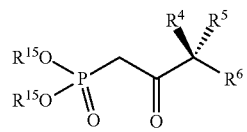

(9)

wherein:
$R^4$ and $R^5$ are each independently H or $C_1$-$C_4$ alkyl; or $R^4$ and $R^5$ together with the carbon to which they are attached form a $C_3$-$C_5$ cycloalkyl;
$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or L$^3$-R$^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —C$_1$-$C_3$alkylene-$C_1$-$C_3$alkoxy;
$L^3$ is $C_1$-$C_6$alkylene, $C_2$-$C_6$alkenylene, $C_2$-$C_6$alkynylene;
$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —C$_1$-$C_3$alkylene-$C_1$-$C_3$alkoxy; and
$R^{15}$ is $C_1$-$C_6$alkyl.

In one embodiment according to this aspect is provided a group of compounds of formula (9) wherein $L^3$ is as defined above and:
$R^4$ and $R^5$ are each independently H or $C_1$-$C_4$ alkyl;
$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or L$^3$-R$^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —C$_1$-$C_3$alkylene-$C_1$-$C_3$alkoxy; and
$R^7$ is phenyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —C$_1$-$C_3$alkylene-$C_1$-$C_3$alkoxy.

In another embodiment according to this aspect is provided a subgroup of compounds of formula (9) wherein:
$R^4$ is methyl;
$R^5$ is hydrogen;
$R^6$ is —CH$_2$—C≡C—$C_1$-$C_4$alkyl or L$^3$-R$^7$;
$L^3$ is $C_3$-$C_6$alkylene;
$R^7$ is phenyl; and
$R^{15}$ is methyl or ethyl.

In another embodiment according to this aspect is provided another subgroup of compounds of formula (9) wherein:
$R^4$ is hydrogen;
$R^5$ is methyl;
$R^6$ is —CH$_2$—C≡C—$C_1$-$C_4$alkyl or L$^3$-R$^7$;
$L^3$ is $C_3$-$C_6$alkylene;
$R^7$ is phenyl; and
$R^{15}$ is methyl or ethyl.

In another aspect of the invention is provided a compound $X^1$-$L^1$-$R^1$, wherein:
$X^1$ is selected from the group consisting of bromo, chloro, iodo, an alkylsulfonate, a fluoroalkylsulfonate, and an arylsulfonate;
$L^1$ is
a) $C_3$-$C_7$alkylene, $C_3$-$C_7$alkenylene, or $C_3$-$C_7$alkynylene; or
b) —(CH$_2$)$_{n1}$-G$^2$-(CH$_2$)$_p$—, —(CH$_2$)$_{n2}$—C≡C-G$^2$-, or —(CH$_2$)$_{n2}$—C(R$^{12}$)=C(R$^{12}$)-G$^2$-, wherein n1 is 2, 3, 4, or 5, n2 is 1, 2, or 3, p is 0, 1, 2, or 3, and n1+p=2, 3, 4, 5, or 6;

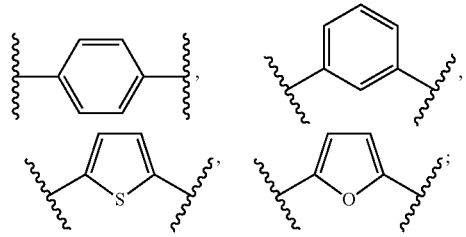

$R^1$ is a protected carboxylic acid; and
$R^{12}$ is H or $C_1$-$C_4$ alkyl.

In one embodiment according to this aspect is provided a group of compounds of formula $X^1$-$L^1$-$R^1$ wherein $X^1$ is as defined above and:
$R^1$ is a protected carboxylic acid;
$L^1$ is n-hexylene, —(CH$_2$)$_3$-G$^2$-, —CH$_2$—C≡C-G$^2$-, or —CH$_2$—C(H)=C(H)-G$^2$-; and $G^2$ is

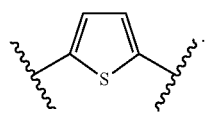 [SMILES: *c1ccc(*)s1]

In another embodiment according to this aspect is provided a subgroup of compounds of formula $X^1$-$L^1$-$R^1$ wherein $R^1$, $X^1$, and $G^2$ are as defined above and:
$L^1$ is —$(CH_2)_3$-$G^2$-.

Chemistry and Examples

Unless otherwise defined herein, scientific and technical terms used in connection with the exemplary embodiments shall have the meanings that are commonly understood by those of ordinary skill in the art.

Further, unless otherwise required by context, singular terms shall include pluralities and plural terms shall include the singular. Generally, nomenclature used in connection with, and techniques of chemistry and molecular biology described herein are those well-known and commonly used in the art.

It will be appreciated that the synthetic schemes and specific examples are illustrative and are not to be read as limiting the scope of the invention. Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. The skilled artisan will also appreciate that not all of the substituents in the compounds of formula (IA) or the intermediates required to synthesize the compounds of formula (IA) will tolerate certain reaction conditions employed to synthesize the compounds. Routine experimentation, including appropriate manipulation of the reaction conditions, reagents and sequence of the synthetic route, protection and deprotection may be required in the case of particular compounds. Suitable protecting groups and the methods for protecting and deprotecting different substituents using such suitable protecting groups are well known to those skilled in the art; examples of which may be found in T. Greene and P. Wuts, Protecting Groups in Chemical Synthesis (3 d ed.), John Wiley & Sons, NY (1999), which is incorporated herein by reference in its entirety.

Furthermore, the skilled artisan will appreciate that in some cases, the order in which moieties are introduced may vary. The particular order of steps required to produce the compounds of formula (IA) is dependent upon the particular compounds being synthesized, the starting compound, and the relative stability of the substituted moieties. Thus, synthesis of the present compounds may be accomplished by methods analogous to those described in the synthetic schemes described herein and in the specific examples, with routine experimentation (e.g., manipulation of the reaction conditions, reagents, and sequence of the synthetic steps).

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it may be obtained by carrying out one of the above procedures using a pure geometric isomer as a starting material, or by resolution of a mixture of the geometric isomers of the compound or intermediates using a standard procedure such as chromatographic separation.

Systematic names of compound structures have been generated by the Convert-Structure-to-Name function of Chem & Bio Draw 12.0 Ultra by CambridgeSoft®, which uses the Cahn-Ingold-Prelog rules for stereochemistry. When discussing individual atomic positions of compound structures, an alternative continuous numbering scheme for the lactams as described below may be used.

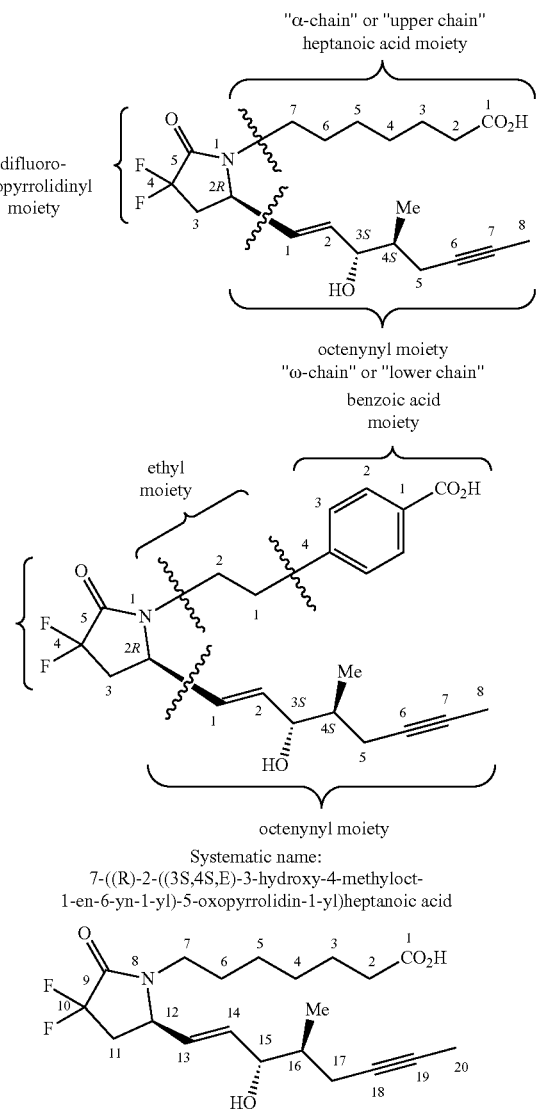

-continued 4-(2-((R)-2-((3S,4S,E)-3-hydroxy-4-methyloct-1-en-6-yn-1-yl)-5-oxopyrrolidin-1-yl)ethyl)benzoic acid

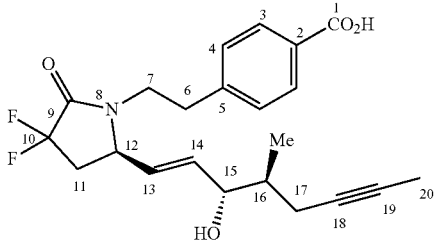

Alternative atom-position numbering schemes for γ-lactams (also known as oxopyrrolidines or pyrrolidinones)

Liquid chromatography—mass spectra (LC/MS) were obtained using an Agilent LC/MSD G1946D or an Agilent 1100 Series LC/MSD Trap G1311A or G2435A. Quantifications were obtained on a Cary 50 Bio UV-visible spectrophotometer.

$^1$H, $^{13}$C, and $^{19}$F Nuclear magnetic resonance (NMR) spectra were obtained using a Varian INOVA nuclear magnetic resonance spectrometer at 400, 100, and 376 MHz, respectively.

High performance liquid chromatography (HPLC) analytical separations were performed on an Agilent 1100 or Agilent 1200 HPLC analytical system and followed by an Agilent Technologies G1315B Diode Array Detector set at or near the $UV_{max}$@ 260 nm.

High performance liquid chromatography (HPLC) preparatory separations were performed on a Gilson preparative HPLC system or an Agilent 1100 preparative HPLC system and followed by an Agilent Technologies G1315B Diode Array Detector set at or near the $UV_{max}$@ 260 nm.

Analytical chiral HPLC separations were performed on an Agilent 1100 analytical system and followed by an Agilent Technologies G1315B Diode Array Detector set at or near the $UV_{max}$ @ 260 nm.

Thin layer chromatography (TLC) analyses were performed on Uniplate™ 250μ silica gel plates (Analtech, Inc. Catalog No. 02521) and were typically developed for visualization using 50 volume % concentrated sulfuric acid in water spray unless otherwise indicated.

When used in the present application, the following abbreviations have the meaning set out below:

Ac is acetyl;
ACN is acetonitrile;
$BBr_3$ is boron tribromide;
Bn is benzyl;
$BnNH_2$ is benzylamine;
BSA is bovine serum albumin;
$CH_2Cl_2$ is dichloromethane;
$CHCl_3$ is chloroform;
$CDCl_3$ is deuterochloroform;
CSA is camphorsulfonic acid;
DCC is N,N'-dicyclohexylcarbodiimide;
DME is 1,2-dimethoxyethane;
DMF is N,N-dimethylfornmamide;
DMP is 2,2-dimethoxypropane (also called, acetone dimethyl acetal);
DMSO is dimethyl sulfoxide;
DBU is 1,8-diazabicyclo[5.4.0]undec-7-ene;
DIA is diisopropylamine;
DMAP is 4-dimethylaminopyridine;
EDC/EDAC is N-(3-dimethylaminopropyl)-N'-ethylcarbodiimide hydrochloride;
EDTA is ethylenediaminetetraacetic acid;
EE is ethoxyeth-1-yl;
ee is enantiomeric excess;
EIA is enzyme immunoassay;
Et is ethyl;
EtOAc is ethyl acetate;
EtOH is ethanol;
$Et_3N$ is triethylamine;
HCl is hydrogen chloride;
HOBt is 1-hydroxybenzotriazole;
Me is methyl;
MeOH is methanol;
MTBE is methyl tert-butyl ether;
NaOMe is sodium methoxide;
nBuLi or n-BuLi is n-butyllithium;
NFSi or NFSI is N-fluorobenzenesulfonimide;
NHS is N-hydroxysuccinimide;
NMP is 1-methyl-2-pyrrolidinone:
PG is a protecting group;
Ph is phenyl;
$Pd(PPh_3)_4$ is tetrakis(triphenylphosphine)palladium;
PhMe is toluene;
rt is room temperature;
TBAF is tetrabutylammonium fluoride;
TBS or TBDMS is tert-butyldimethylsilyl;
tBu or t-Bu is tert-butyl;
TEA is triethylamine;
TFA is trifluoroacetic acid;
THF is tetrahydrofuran;
TMS is trimethylsilyl; and
Tris-HCl is 2-amino-2-(hydroxymethyl)-1,3-propanediol hydrochloride.

The general method for the synthesis of compounds described by Figure IA involves the respective connection of the three components shown in the general Scheme 2 below.

Scheme 2 toward compounds of FIG. IA

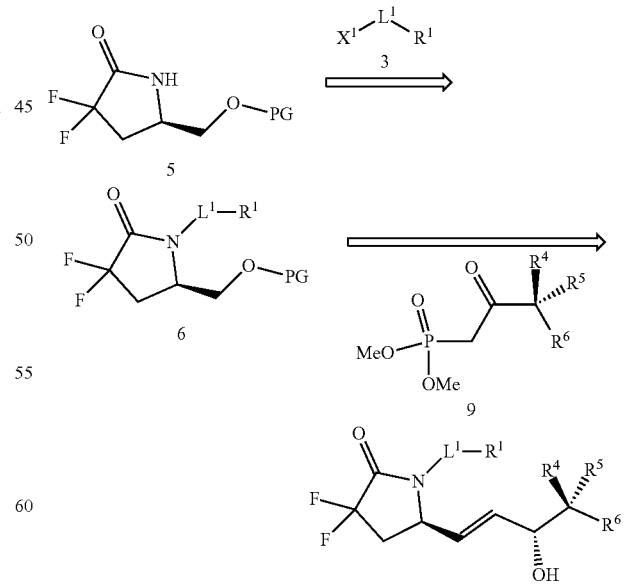

FIG. IA

Some $X^1$-$L^1$-$R^1$s for the introduction of the upper chains exemplified in The Summary of the Invention are commercially available like methyl 7-bromoheptanoate, (3a), but some may require synthesis from commercially available material. The present invention provides the following synthetic steps for the preparation of 3b, but is not limited to the reaction conditions.

Scheme 3

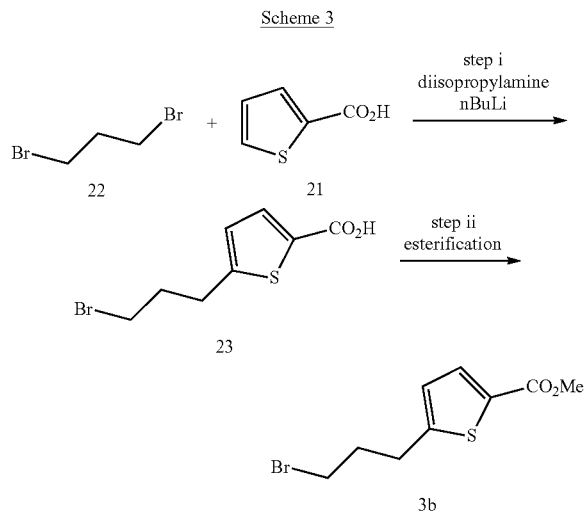

Synthetic pathways toward β-keto-phosphonate esters,

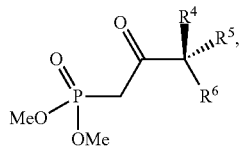

Some β-keto-phosphonate esters used in the synthesis of compounds of Formula IA may be commercially available, but some may require synthesis from commercially available material. Scheme 4 below describes how β-keto-phosphonate esters (9) may be synthesized. The present invention also provides steps that may be included into the steps below that may enhance the quality of the intermediates.

Organic β-keto phosphonate esters such as

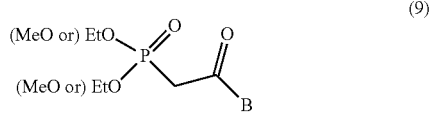

(9)

may be used as reaction coupling partners with aldehydes such as 3a and 3b (shown in Scheme 2) in a Homer-Emmons-Wadsworth-type process to install the lactam lower-chain. Such β-keto phosphonate esters may be prepared by coupling an appropriate carboxylic ester

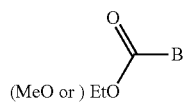

(19)

with lithiated/deprotonated dialkyl methylphosphonate according to the general reaction illustrated in Scheme 6 and variations thereof. Tables A—P/Q of Lower Chains (below) describe various lower-chain components B of the exemplary embodiments.

Carboxylic esters 19 may be commercially available or prepared from commercially-available starting materials as shown in Schemes 7a-g. A carboxylic ester, 19(a-o, indicating various $R^6$ groups as described in the Tables of Lower Chains) a (a indicating both $R^4$ and $R^5$ are hydrogen) or 19(a-o)b/c (b/c indicating that a single $R^4$ or single $R^5$, respectively, is present)(i-viii, indicating which $C_1$-$C_4$ alkyl substituent forms $R^4$ or $R^5$), may be prepared in two steps from commercially available diethyl malonate or an appropriate commercially available diethyl 2-($C_1$-$C_4$ alkyl) malonate starting material. Reaction of the malonate starting material with an appropriate lithium amide base, such as LDA or LiHMDS, or an appropriate hydride base, such as sodium hydride, or alkoxide base, such as sodium ethoxide, followed with an appropriate alkylating agent $R^6$—$X^1$, as illustrated in Scheme 7a, Step A, affords the corresponding 2-$R^6$-substituted diethyl malonate 14'. Subsequent decarboxylation (Step B) provides the corresponding carboxylic ester intermediate 19, wherein both $R^4$ and $R^5$ are hydrogen, or wherein one of $R^4$ and $R^5$ is a $C_1$-$C_4$ alkyl group (alkyl groups (i) through (viii) represent methyl, ethyl, n-propyl, 2-propyl, n-butyl, iso-butyl, sec-butyl, and tert-butyl, respectively) and the other is a hydrogen. Examples of commercially available diethyl ($C_1$-$C_4$ alkyl) malonates include diethyl methyl malonate, diethyl ethyl malonate, diethyl isopropyl malonate, diethyl n-propyl malonate, diethyl n-butyl malonate (all from Sigma-Aldrich, Acros Organics, or Alfa Aesar), diethyl isobutyl malonate, and diethyl sec-butyl malonate (both from Alfa Aesar). Methods for preparing the starting diethyl ($C_1$-$C_4$ alkyl) malonates are known in the art; for example, diethyl malonate may be combined with a base such as potassium carbonate and an appropriate alkylating agent such as methyl iodide, ethyl iodide, n-propyl bromide, or n-butyl bromide under microwave irradiation in the method described by Keglevich et al. in *Letters in Organic Chemistry*, 2008, 5(3), 224-228 and in *Green Chemistry*, 2006, 8(12), 1073-1075. Other methods that may be used to prepare the diethyl ($C_1$-$C_4$ alkyl) malonates include the reaction of diethyl malonate with an appropriate alkylating agent such as ethyl iodide, isopropyl bromide, isobutyl bromide, or sec-butyl bromide in the presence of a base such as sodium ethoxide in an organic solvent such as ethanol as described in Patel and Ryono in *Bioorganic and Medicinal Chemistry* Letters, 1992, 2(9), 1089-1092 and elsewhere.

Carboxylic ester intermediates 19 possessing a gem-dimethyl substitution at the carbon atom a to the ester carbonyl group (both $R^4$ and $R^5$ are methyl), such as 19(a-o)d(i), may be prepared by the methylation of the corresponding mono-α-methyl ester intermediate (stereochemical mixture) 19(a-o)b/c(i) as shown in Scheme 7b and reported in Shibasaki, M. et al, in *Chemical and Pharmaceutical Bulletin*, 1989, 37(6), 1647-1649.

Scheme 7c illustrates mono-alkylations of commercially available or prepared carboxylic esters 19(a-o)a with an alkylating agent $R^4/R^5$—$X^1$, wherein the $R^4/R^5$ group is a $C_1$-$C_4$ alkyl group and $X^1$ is a leaving group such as iodide or bromide to provide the corresponding mono-alkylated analogs 19(a-o)b/c, respectively. The mono-alkylated carboxylic ester analogs may be alkylated a second time; for example, mono-methylated carboxylic acid esters (stereochemical mixture) 19(a-o)b/c(i) may be methylated a second time to provide the corresponding gem-dimethyl substituted esters 19(a-o)d(i), as illustrated in Scheme 7d.

Scheme 7e illustrates the preparation of 1-$R^6$-substituted $C_3$-$C_5$ cycloalkylcarboxylic acids and their $C_1$-$C_4$ alkyl esters 19(a-o)e(ix-xi). Similar transformations are described in Yang, D. et. al. in *Journal of Organic Chemistry*, 2009, 74(22), 8726-8732; Cowling, S. J. and Goodby, J. W. in *Chemical Communications* (Cambridge, United Kingdom), 2006, 39, 4107-4709; Araldi, G. L. et. al. in WO 2003/103604; and others.

Enantiopure carboxylic esters 19(a-o)b(i-viii) and their stereoisomers, 19(a-o)c(i-viii) may be prepared according to the route illustrated in Scheme 7f. Alkylation of an appropriately-substituted carboxylic acid starting material, such as propionic acid ($R^4/R^5$ is a methyl group), at the carbon position alpha to the acid carbonyl group by treatment of the acid with an appropriate base, such as lithium diisopropylamide (about two molar equivalents) in the presence of a suitable solvent, such as THF, with an alkylating agent $R^6$—$X^1$ (Step A) provides the corresponding carboxylic acid intermediates 18(a-o)b/c(i-viii). Subsequent coupling of the carboxylic acid intermediate with N-hydroxysuccinimide (NHS) forms the corresponding NHS ester (an activated ester) stereoisomeric mixture 20(a-o)b/c(i-viii) (Step B). Treatment of the activated ester stereoisomeric mixture 20(a-o)b/c(i-viii) with (R)-2-amino-2-phenylethanol in THF results in the mixture of two amide diastereomers 21(a-o)b(i-viii) and 21(a-o)c(i-viii) (Step C), which may be separated by chromatography to provide each diastereomer (Step D). Recrystallization of the individual deastereomers may provide amides with even greater de purity. Amide hydrolysis of each diastereomer to its corresponding carboxylic acid 18(a-o)b(i-viii) and 18(a-o)c(i-viii), respectively (Step E), and subsequent esterification (Step F) provides corresponding individual carboxylic ester stereoisomers 19(a-o)b(i-viii) and 19(a-o)c(i-viii), respectively.

Scheme 7g shows a synthetic pathway to stereopure carboxylic esters 19(a-o)b(i-vii) ($R^5$ is hydrogen) employing the use of the chiral auxiliary for more-efficient (asymmetric) alkylation in Step C. Removal of the chiral auxiliary (Step D) following alkylation and subsequent derivatization (Steps E and F) provides the diastereomers separable by chromatography and further purified by crystallization (Step G). Acid-catalyzed amide hydrolysis (Step H) and subsequent esterification (Step I) provide the desired stereopure intermediates, which can be carried onto their corresponding stereopure β-keto phosphonate esters 9(a-o)b(i-vii).

Scheme 8 illustrates the conversions of acetylenic carboxylic esters 19(a-f)a and 19(a-f)(b-e)(i-xi) to the corresponding β-keto phosphonates by the previously-described general manner (Step A) and subsequent catalytic hydrogenation (Step B) to provide the corresponding saturated analogs.

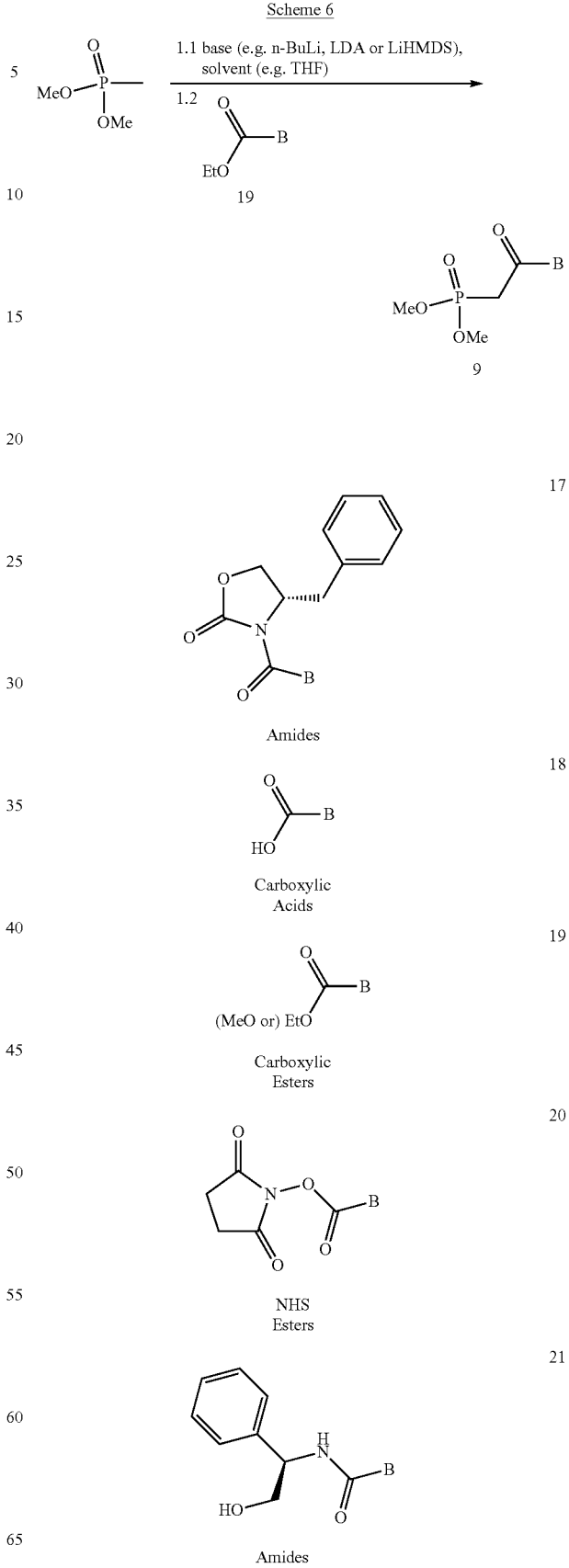

-continued

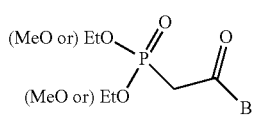

Phosphonate Esters

TABLE A of Lower Chains

| B | R⁴ | R⁵ | R⁶ |
|---|----|----|----|
| aa | H | H | 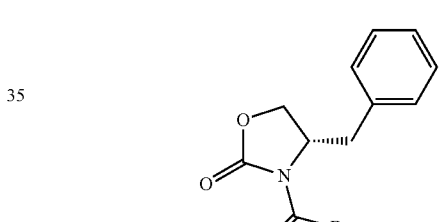 |
| ab(i) | Me | H | |
| ac(i) | H | Me | |
| ad(i) | Me | Me | |
| ab(ii) | Et | H | |
| ac(ii) | H | Et | |
| ad(ii) | Et | Et | |
| ab(iii) | n-Pr | H | |
| ac(iii) | H | n-Pr | |
| ad(iii) | n-Pr | n-Pr | |
| ab(iv) | i-Pr | H | |
| ac(iv) | H | i-Pr | |
| ad(iv) | i-Pr | i-Pr | |
| ab(v) | n-Bu | H | |
| ac(v) | H | n-Bu | |
| ad(v) | n-Bu | n-Bu | |
| ab(vi) | i-Bu | H | |
| ac(vi) | H | i-Bu | |
| ad(vi) | i-Bu | i-Bu | |
| ab(vii) | sec-Bu | H | |
| ac(vii) | H | sec-Bu | |
| ad(vii) | sec-Bu | sec-Bu | |
| ab(viii) | tert-Bu | H | |
| ac(viii) | H | tert-Bu | |
| ad(viii) | tert-Bu | tert-Bu | |
| ae(ix) | —CH₂—CH₂— | | |
| ae(x) | —(CH₂)₂—CH₂— | | |

TABLE A-continued of Lower Chains

| B | R⁴ | R⁵ | R⁶ |
|---|----|----|----|
| ae(xi) | —(CH₂)₃—CH₂— | | |

B = $\overset{R^4\ R^5}{\underset{}{\text{C}}}$—R⁶

R₄ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu = C₃-C₅ cycloalkyl
(ix) cyclopropyl
(x) cyclobutyl
(xi) cyclopentyl

*R⁴ and R⁵ may both be C₁-C₄ alkyl groups that are not the same. Although no examples of these embodiments are represented in these tables, their absence infers no limitation in scope.

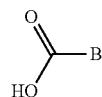

Amides

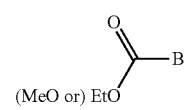

Carboxylic Acids

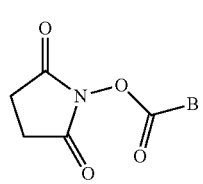

Carboxylic Esters

NHS Esters

-continued

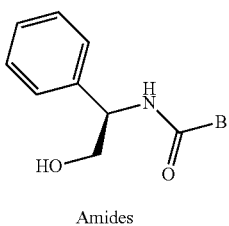

Amides

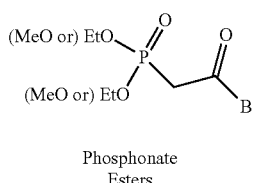

Phosphonate Esters

TABLE B of Lower Chains

| B | $R^4$ | $R^5$ | $R^6$ |
|---|---|---|---|
| ba | H | H | 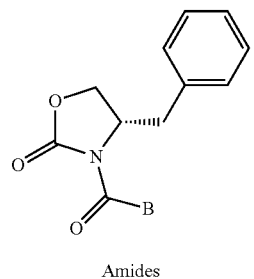 |
| bb(i) | Me | H | |
| bc(i) | H | Me | |
| bd(i) | Me | Me | |
| bb(ii) | Et | H | |
| bc(ii) | H | Et | |
| bd(ii) | Et | Et | |
| bb(iii) | n-Pr | H | |
| bc(iii) | H | n-Pr | |
| bd(iii) | n-Pr | n-Pr | |
| bb(iv) | i-Pr | H | |
| bc(iv) | H | i-Pr | |
| bd(iv) | i-Pr | i-Pr | |
| bb(v) | n-Bu | H | |
| bc(v) | H | n-Bu | |
| bd(v) | n-Bu | n-Bu | |
| bb(vi) | i-Bu | H | |
| bc(vi) | H | i-Bu | |
| bd(vi) | i-Bu | i-Bu | |
| bb(vii) | sec-Bu | H | |
| bc(vii) | H | sec-Bu | |
| bd(vii) | sec-Bu | sec-Bu | |
| bb(viii) | tert-Bu | H | |
| bc(viii) | H | tert-Bu | |
| bd(viii) | tert-Bu | tert-Bu | |
| be(ix) | | | —CH₂—CH₂— |
| be(x) | | | —(CH₂)₂—CH₂— |

TABLE B-continued of Lower Chains

| B | $R^4$ | $R^5$ | $R^6$ |
|---|---|---|---|
| be(xi) | | | —(CH₂)₃—CH₂— |

B = (structure with $R^4$, $R^5$, $R^6$)

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl
(ix) cyclopropyl
(x) cyclobutyl
(xi) cyclopentyl

*$R^4$ and $R^5$ may both be $C_1$—$C_4$ alkyl groups that are not the same. Although no examples of these embodiments are represented in these tables, their absence infers no limitation in scope.

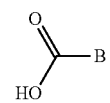

Amides

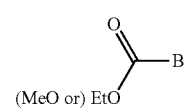

Carboxylic Acids

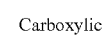

Carboxylic Esters

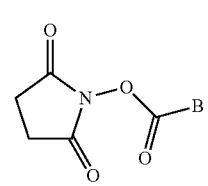

NHS Esters

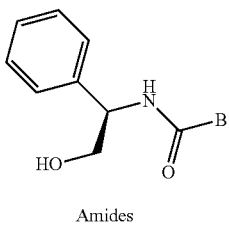

Amides

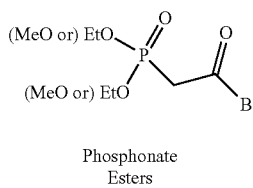

Phosphonate Esters

TABLE C

| | | of Lower Chains | |
|---|---|---|---|
| B | R⁴ | R⁵ | R⁶ |
| ca | H | H | ⁅wavy⁆–C≡C–CH₂CH₂CH₃ |
| cb(i) | Me | H | |
| cc(i) | H | Me | |
| cd(i) | Me | Me | |
| cb(ii) | Et | H | |
| cc(ii) | H | Et | |
| cd(ii) | Et | Et | |
| cb(iii) | n-Pr | H | |
| cc(iii) | H | n-Pr | |
| cd(iii) | n-Pr | n-Pr | |
| cb(iv) | i-Pr | H | |
| cc(iv) | H | i-Pr | |
| cd(iv) | i-Pr | i-Pr | |
| cb(v) | n-Bu | H | |
| cc(v) | H | n-Bu | |
| cd(v) | n-Bu | n-Bu | |
| cb(vi) | i-Bu | H | |
| cc(vi) | H | i-Bu | |
| cd(vi) | i-Bu | i-Bu | |
| cb(vii) | sec-Bu | H | |
| cc(vii) | H | sec-Bu | |
| cd(vii) | sec-Bu | sec-Bu | |
| cb(viii) | tert-Bu | H | |
| cc(viii) | H | tert-Bu | |
| cd(viii) | tert-Bu | tert-Bu | |
| ce(ix) | | –CH₂–CH₂– | |
| ce(x) | | –(CH₂)₂–CH₂– | |
| ce(xi) | | –(CH₂)₃–CH₂– | |

$B = $ with $R^4, R^5, R^6$ substituents $R^4$ and/or $R^5 = $ $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl
(ix) cyclopropyl
(x) cyclobutyl
(xi) cyclopentyl

*$R^4$ and $R^5$ may both be $C_1$—$C_4$ alkyl groups that are not the same. Although no examples of these embodiments are represented in these tables, their absence infers no limitation in scope.

17

Amides

18

Carboxylic Acids

19

Carboxylic Esters

20

NHS Esters

-continued

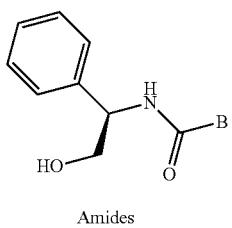

Amides

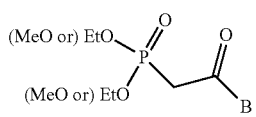

Phosphonate Esters

TABLE D of Lower Chains

| B | R⁴ | R⁵ | R⁶ |
|---|----|----|----|
| da | H | H | |
| db(i) | Me | H | |
| dc(i) | H | Me | |
| dd(i) | Me | Me | |
| db(ii) | Et | H | |
| dc(ii) | H | Et | |
| dd(ii) | Et | Et | 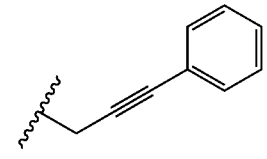 [SMILES: *CC#Cc1ccccc1] |
| db(iii) | n-Pr | H | |
| dc(iii) | H | n-Pr | |
| dd(iii) | n-Pr | n-Pr | |
| db(iv) | i-Pr | H | |
| dc(iv) | H | i-Pr | |
| dd(iv) | i-Pr | i-Pr | |
| db(v) | n-Bu | H | |
| dc(v) | H | n-Bu | |
| dd(v) | n-Bu | n-Bu | |
| db(vi) | i-Bu | H | |
| dc(vi) | H | i-Bu | |
| dd(vi) | i-Bu | i-Bu | |
| db(vii) | sec-Bu | H | |
| dc(vii) | H | sec-Bu | |
| dd(vii) | sec-Bu | sec-Bu | |
| db(viii) | tert-Bu | H | |
| dc(viii) | H | tert-Bu | |
| dd(viii) | tert-Bu | tert-Bu | |
| de(ix) | | | 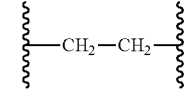 |
| de(x) | | | 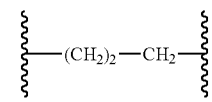 |

TABLE D-continued of Lower Chains

| B | R⁴ | R⁵ | R⁶ |
|---|----|----|----|
| de(xi) | | | 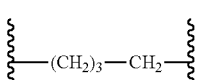 |

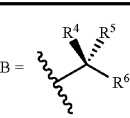

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu

 = C₃-C₅ cycloalkyl
(ix) cyclopropyl
(x) cyclobutyl
(xi) cyclopentyl

*R⁴ and R⁵ may both be C₁—C₄ alkyl groups that are not the same. Although no examples of these embodiments are represented in these tables, their absence infers no limitation in scope.

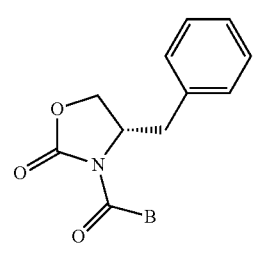

Amides

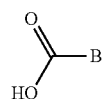

Carboxylic Acids

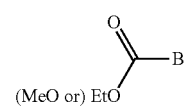

Carboxylic Esters

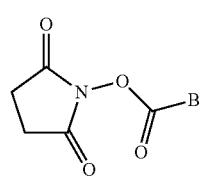

NHS Esters

-continued

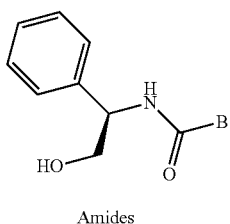

Amides

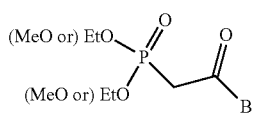

Phosphonate Esters

TABLE E of Lower Chains

| B | $R^4$ | $R^5$ | $R^6$ |
|---|---|---|---|
| ea | H | H | (phenylpropargyl group) |
| eb(i) | Me | H | |
| ec(i) | H | Me | |
| ed(i) | Me | Me | |
| eb(ii) | Et | H | |
| ec(ii) | H | Et | |
| ed(ii) | Et | Et | |
| eb(iii) | n-Pr | H | |
| ec(iii) | H | n-Pr | |
| ed(iii) | n-Pr | n-Pr | |
| eb(iv) | i-Pr | H | |
| ec(iv) | H | i-Pr | |
| ed(iv) | i-Pr | i-Pr | |
| eb(v) | n-Bu | H | |
| ec(v) | H | n-Bu | |
| ed(v) | n-Bu | n-Bu | |
| eb(vi) | i-Bu | H | |
| ec(vi) | H | i-Bu | |
| ed(vi) | i-Bu | i-Bu | |
| eb(vii) | sec-Bu | H | |
| ec(vii) | H | sec-Bu | |
| ed(vii) | sec-Bu | sec-Bu | |
| eb(viii) | tert-Bu | H | |
| ec(viii) | H | tert-Bu | |
| ed(viii) | tert-Bu | tert-Bu | |
| ee(ix) | | —(CH$_2$)$_2$—CH$_2$— | |
| ee(x) | | —(CH$_2$)$_2$—CH$_2$— | |

TABLE E-continued of Lower Chains

| B | $R^4$ | $R^5$ | $R^6$ |
|---|---|---|---|
| ee(xi) | | —(CH$_2$)$_3$—CH$_2$— | |

B = (tetrahedral carbon with $R^4$, $R^5$, $R^6$)

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl
(ix) cyclopropyl
(x) cyclobutyl
(xi) cyclopentyl

*$R^4$ and $R^5$ may both be $C_1$—$C_4$ alkyl groups that are not the same. Although no examples of these embodiments are represented in these tables, their absence infers no limitation in scope.

17

Amides

18

Carboxylic Acids

19

Carboxylic Esters

20

NHS Esters

-continued

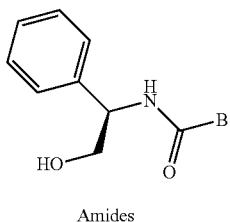

Amides

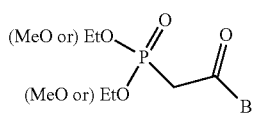

Phosphonate Esters

TABLE F of Lower Chains

| B | R⁴ | R⁵ | R⁶ |
|---|---|---|---|
| fa | H | H | |
| fb(i) | Me | H | |
| fc(i) | H | Me | |
| fd(i) | Me | Me | |
| fb(ii) | Et | H | |
| fc(ii) | H | Et | |
| fd(ii) | Et | Et | |
| fb(iii) | n-Pr | H | |
| fc(iii) | H | n-Pr | |
| fd(iii) | n-Pr | n-Pr | |
| fb(iv) | i-Pr | H | |
| fc(iv) | H | i-Pr | |
| fd(iv) | i-Pr | i-Pr | |
| fb(v) | n-Bu | H | |
| fc(v) | H | n-Bu | |
| fd(v) | n-Bu | n-Bu | |
| fb(vi) | i-Bu | H | |
| fc(vi) | H | i-Bu | |
| fd(vi) | i-Bu | i-Bu | |
| fb(vii) | sec-Bu | H | |
| fc(vii) | H | sec-Bu | |
| fd(vii) | sec-Bu | sec-Bu | |
| fb(viii) | tert-Bu | H | |
| fc(vii) | H | tert-Bu | |
| fd(viii) | tert-Bu | tert-Bu | |
| fe(ix) | | | —CH₂—CH₂— |
| fe(x) | | | —(CH₂)₂—CH₂— |

TABLE F-continued of Lower Chains

| B | R⁴ | R⁵ | R⁶ |
|---|---|---|---|
| fe(xi) | | | —(CH₂)₃—CH₂— |

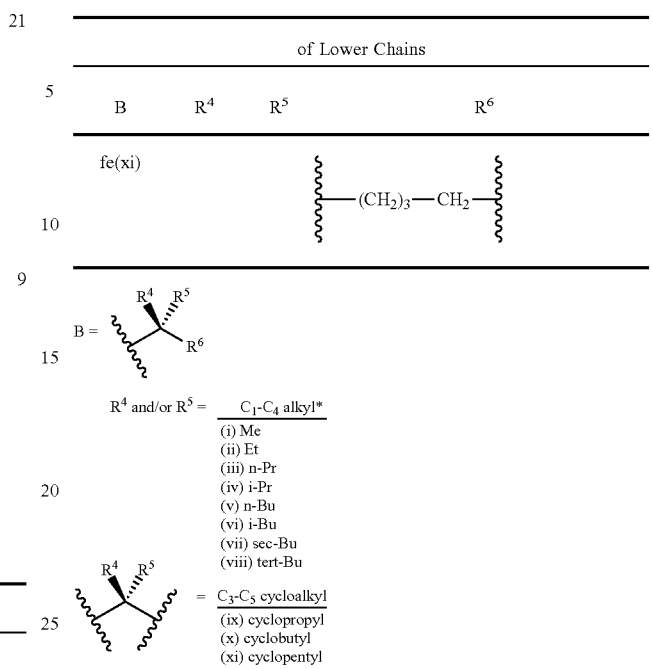

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu = $C_3$-$C_5$ cycloalkyl
(ix) cyclopropyl
(x) cyclobutyl
(xi) cyclopentyl

*$R^4$ and $R^5$ may both be $C_1$—$C_4$ alkyl groups that are not the same. Although no examples of these embodiments are represented in these tables, their absence infers no limitation in scope.

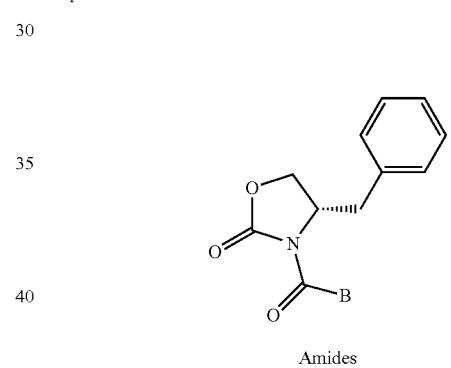

Amides

Carboxylic Acids

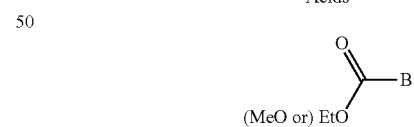

Carboxylic Esters

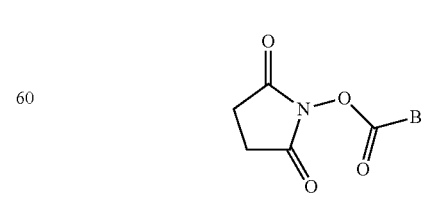

NHS Esters

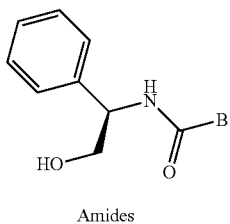

Amides

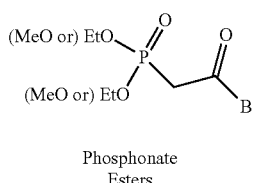

Phosphonate Esters

TABLE G of Lower Chains

| B | $R^4$ | $R^5$ | $R^6$ |
|---|---|---|---|
| ga | H | H | |
| gb(i) | Me | H | |
| gc(i) | H | Me | |
| gd(i) | Me | Me | |
| gb(ii) | Et | H | |
| gc(ii) | H | Et | |
| gd(ii) | Et | Et | |
| gb(iii) | n-Pr | H | |
| gc(iii) | H | n-Pr | |
| gd(iii) | n-Pr | n-Pr | |
| gb(iv) | i-Pr | H | |
| gc(iv) | H | i-Pr | |
| gd(iv) | i-Pr | i-Pr | |
| gb(v) | n-Bu | H | |
| gc(v) | H | n-Bu | |
| gd(v) | n-Bu | n-Bu | |
| gb(vi) | i-Bu | H | |
| gc(vi) | H | i-Bu | |
| gd(vi) | i-Bu | i-Bu | |
| gb(vii) | sec-Bu | H | |
| gc(vii) | H | sec-Bu | |
| gd(vii) | sec-Bu | sec-Bu | |
| gb(viii) | tert-Bu | H | |
| gc(viii) | H | tert-Bu | |
| gd(viii) | tert-Bu | tert-Bu | |
| ge(ix) | —CH$_2$—CH$_2$— | | |
| ge(x) | —(CH$_2$)$_2$—CH$_2$— | | |
| ge(xi) | —(CH$_2$)$_3$—CH$_2$— | | |

$R^4$ and/or $R^5$ =
- $C_1$-$C_4$ alkyl*
  - (i) Me
  - (ii) Et
  - (iii) n-Pr
  - (iv) i-Pr
  - (v) n-Bu
  - (vi) i-Bu
  - (vii) sec-Bu
  - (viii) tert-Bu
- $C_3$-$C_5$ cycloalkyl
  - (ix) cyclopropyl
  - (x) cyclobutyl
  - (xi) cyclopentyl

*$R^4$ and $R^5$ may both be $C_1$—$C_4$ alkyl groups that are not the same. Although no examples of these embodiments are represented in these tables, their absence infers no limitation in scope.

17

Amides

18

Carboxylic Acids

19

Carboxylic Esters

20

NHS Esters

-continued

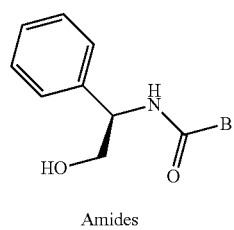

Amides

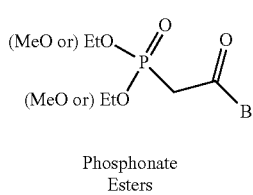

Phosphonate Esters

TABLE H of Lower Chains

| B | $R^4$ | $R^5$ | $R^8$ |
|---|---|---|---|
| ha | H | H | |
| hb(i) | Me | H | |
| hc(i) | H | Me | |
| hd(i) | Me | Me | |
| hb(ii) | Et | H | |
| hc(ii) | H | Et | |
| hd(ii) | Et | Et | |
| hb(iii) | n-Pr | H | |
| hc(iii) | H | n-Pr | |
| hd(iii) | n-Pr | n-Pr | |
| hb(iv) | i-Pr | H | |
| hc(iv) | H | i-Pr | |
| hd(iv) | i-Pr | i-Pr | |
| hb(v) | n-Bu | H | |
| hc(v) | H | n-Bu | |
| hd(v) | n-Bu | n-Bu | |
| hb(vi) | i-Bu | H | |
| hc(vi) | H | i-Bu | |
| hd(vi) | i-Bu | i-Bu | |
| hb(vii) | sec-Bu | H | |
| hc(vii) | H | sec-Bu | |
| hd(vii) | sec-Bu | sec-Bu | |
| hb(viii) | tert-Bu | H | |
| hc(viii) | H | tert-Bu | |
| hd(viii) | tert-Bu | tert-Bu | |
| he(ix) | | | —CH$_2$—CH$_2$— |
| he(x) | | | —(CH$_2$)$_2$—CH$_2$— |
| he(xi) | | | —(CH$_2$)$_3$—CH$_2$— |

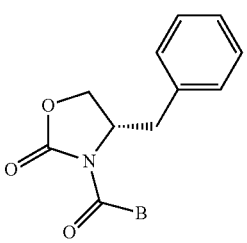

Amides

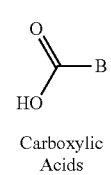

Carboxylic Acids

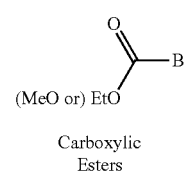

Carboxylic Esters

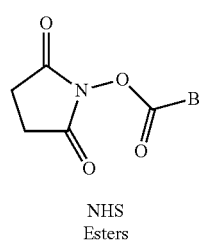

NHS Esters

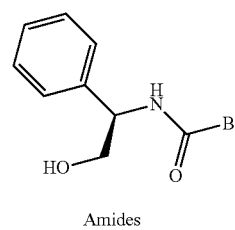

Amides

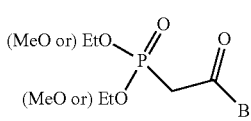

Phosphonate Esters

TABLE I of Lower Chains

| B | $R^4$ | $R^5$ | $R^6$ |
|---|---|---|---|
| ia | H | H | |
| ib(i) | Me | H | |
| ic(i) | H | Me | |
| id(i) | Me | Me | |
| ib(ii) | Et | H | |

TABLE I-continued of Lower Chains

| B | R⁴ | R⁵ | R⁶ |
|---|----|----|-----|
| ic(ii) | H | Et | |
| id(ii) | Et | Et | |
| ib(iii) | n-Pr | H | |
| ic(iii) | H | n-Pr | |
| id(iii) | n-Pr | n-Pr | |
| ib(iv) | i-Pr | H | |
| ic(iv) | H | i-Pr | |
| id(iv) | i-Pr | i-Pr | |
| ib(v) | n-Bu | H | |
| ic(v) | H | n-Bu | |
| id(v) | n-Bu | n-Bu | |
| ib(vi) | i-Bu | H | |
| ic(vi) | H | i-Bu | |
| id(vi) | i-Bu | i-Bu | |
| ib(vii) | sec-Bu | H | |
| ic(vii) | H | sec-Bu | |
| id(vii) | sec-Bu | sec-Bu | |
| ib(viii) | tert-Bu | H | |
| ic(viii) | H | tert-Bu | |
| id(viii) | tert-Bu | tert-Bu | |
| ie(ix) | | —CH₂—CH₂— | |
| ie(x) | | —(CH₂)₂—CH₂— | |
| ie(xi) | | —(CH₂)₃—CH₂— | |

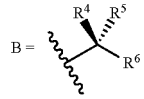

B =

R⁴ and/or R⁵ =   C₁–C₄ alkyl*
 (i) Me
 (ii) Et
 (iii) n-Pr
 (iv) i-Pr
 (v) n-Bu
 (vi) i-Bu
 (vii) sec-Bu
 (viii) tert-Bu

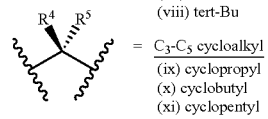 = C₃–C₅ cycloalkyl
 (ix) cyclopropyl
 (x) cyclobutyl
 (xi) cyclopentyl

*R⁴ and R⁵ may both be C₁–C₄ alkyl groups that are not the same. Although no examples of these emboiments are represented in these tables, their absence infers no limitation in scope.

17

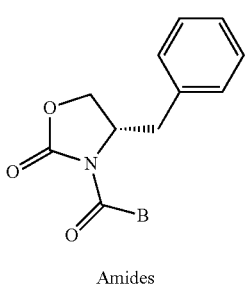

Amides

18

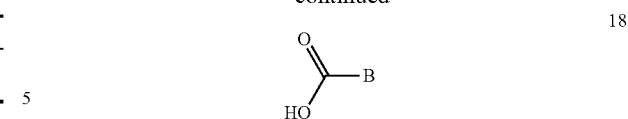

Carboxylic Acids

19

Carboxylic Esters

20

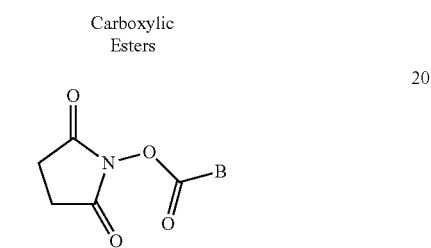

NHS Esters

21

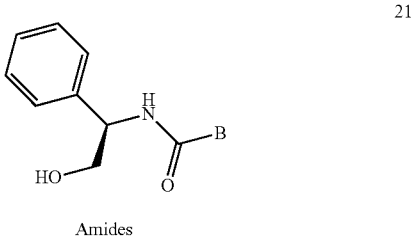

Amides

9

Phosphonate Esters

TABLE J of Lower Chains

| B | R⁴ | R⁵ | R⁶ |
|---|----|----|-----|
| ja | H | H | 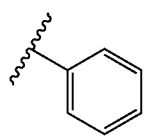 [SMILES: *c1ccccc1] |
| jb(i) | Me | H | |
| jc(i) | H | Me | |
| jd(i) | Me | Me | |
| jb(ii) | Et | H | |
| jc(ii) | H | Et | |
| jd(ii) | Et | Et | |
| jb(iii) | n-Pr | H | |
| jc(iii) | H | n-Pr | |
| jd(iii) | n-Pr | n-Pr | |
| jb(iv) | i-Pr | H | |
| jc(iv) | H | i-Pr | |
| jd(iv) | i-Pr | i-Pr | |
| jb(v) | n-Bu | H | |
| jc(v) | H | n-Bu | |
| jd(v) | n-Bu | n-Bu | |
| jb(vi) | i-Bu | H | |

TABLE J-continued of Lower Chains

| B | R⁴ | R⁵ | R⁶ |
|---|---|---|---|
| jc(vi) | H | i-Bu | |
| jd(vi) | i-Bu | i-Bu | |
| jb(vii) | sec-Bu | H | |
| jc(vii) | H | sec-Bu | |
| jd(vii) | sec-Bu | sec-Bu | |
| jb(viii) | tert-Bu | H | |
| jc(viii) | H | tert-Bu | |
| jd(viii) | tert-Bu | tert-Bu | |
| je(ix) | | —CH₂—CH₂— | |
| je(x) | | —(CH₂)₂—CH₂— | |
| je(xi) | | —(CH₂)₃—CH₂— | |

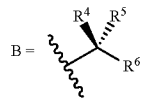

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu

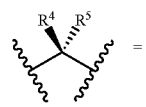 = C₃-C₅ cycloalkyl
(ix) cyclopropyl
(x) cyclobutyl
(xi) cyclopentyl

*R⁴ and R⁵ may both be C₁—C₄ alkyl groups that are not the same. Although no examples of these embodiments are represented in these tables, their absence infers no limitation in scope.

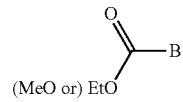

Amides    17

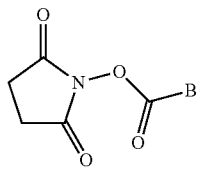

Carboxylic Acids    18

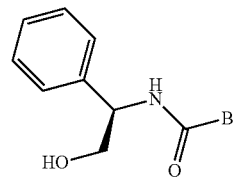

Carboxylic Esters    19

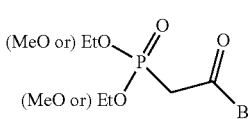

NHS Esters    20

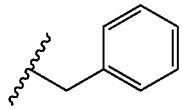 [SMILES: *Cc1ccccc1]

Amides    21

Phosphonate Esters    9

TABLE K of Lower Chains

| B | R⁴ | R⁵ | R⁶ |
|---|---|---|---|
| ka | H | H | 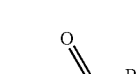 |
| kb(i) | Me | H | |
| kc(i) | H | Me | |
| kd(i) | Me | Me | |
| kb(ii) | Et | H | |
| kc(ii) | H | Et | |
| kd(ii) | Et | Et | |
| kb(iii) | n-Pr | H | |
| kc(iii) | H | n-Pr | |
| kd(iii) | n-Pr | n-Pr | |
| kb(iv) | i-Pr | H | |
| kc(iv) | H | i-Pr | |
| kd(iv) | i-Pr | i-Pr | |
| kb(v) | n-Bu | H | |
| kc(v) | H | n-Bu | |
| kd(v) | n-Bu | n-Bu | |
| kb(vi) | i-Bu | H | |
| kc(vi) | H | i-Bu | |
| kd(vi) | i-Bu | i-Bu | |
| kb(vii) | sec-Bu | H | |
| kc(vii) | H | sec-Bu | |
| kd(vii) | sec-Bu | sec-Bu | |
| kb(viii) | tert-Bu | H | |
| kc(viii) | H | tert-Bu | |
| kd(viii) | tert-Bu | tert-Bu | |

TABLE K-continued

| | of Lower Chains | | |
|---|---|---|---|
| B | $R^4$ | $R^5$ | $R^6$ |
| ke(ix) | | | 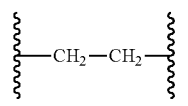 —CH$_2$—CH$_2$— |
| ke(x) | | | 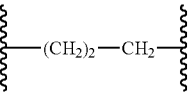 —(CH$_2$)$_2$—CH$_2$— |
| ke(xi) | | | 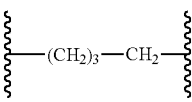 —(CH$_2$)$_3$—CH$_2$— |

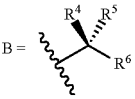

B =

$R^4$ and/or $R^5$ = $C_1$-$C_4$ alkyl*
(i) Me
(ii) Et
(iii) n-Pr
(iv) i-Pr
(v) n-Bu
(vi) i-Bu
(vii) sec-Bu
(viii) tert-Bu

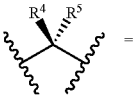 = $C_3$-$C_5$ cycloalkyl
(ix) cyclopropyl
(x) cyclobutyl
(xi) cyclopentyl

*$R^4$ and $R^5$ may both be $C_1$—$C_4$ alkyl groups that are not the same. Although no examples of these embodiments are represented in these tables, their absence infers no limitation in scope.

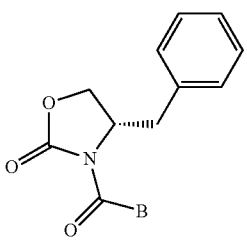

17

Amides

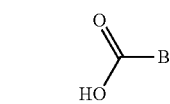

18

Carboxylic Acids

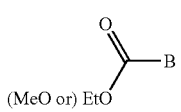

19

(MeO or) EtO

Carboxylic Esters

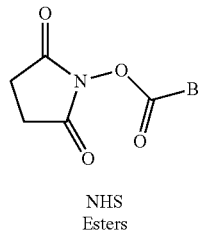

20

NHS Esters

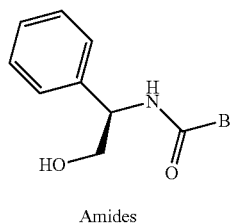

21

Amides

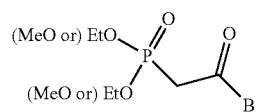

9

(MeO or) EtO
(MeO or) EtO

Phosphonate Esters

TABLE L

| | of Lower Chains | | |
|---|---|---|---|
| B | $R^4$ | $R^5$ | $R^6$ |
| Ia | H | H | 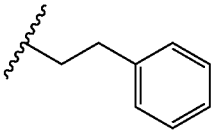 [SMILES: *CCc1ccccc1] |
| Ib(i) | Me | H | |
| Ic(i) | H | Me | |
| Id(i) | Me | Me | |
| Ib(ii) | Et | H | |
| Ic(ii) | H | Et | |
| Id(ii) | Et | Et | |
| Ib(iii) | n-Pr | H | |
| Ic(iii) | H | n-Pr | |
| Id(iii) | n-Pr | n-Pr | |
| Ib(iv) | i-Pr | H | |
| Ic(iv) | H | i-Pr | |
| Id(iv) | i-Pr | i-Pr | |
| Ib(v) | n-Bu | H | |
| Ic(v) | H | n-Bu | |
| Id(v) | n-Bu | n-Bu | |
| Ib(vi) | i-Bu | H | |
| Ic(vi) | H | i-Bu | |
| Id(vi) | i-Bu | i-Bu | |
| Ib(vii) | sec-Bu | H | |
| Ic(vii) | H | sec-Bu | |
| Id(vii) | sec-Bu | sec-Bu | |
| Ib(viii) | tert-Bu | H | |
| Ic(viii) | H | tert-Bu | |
| Id(viii) | tert-Bu | tert-Bu | |
| Ie(ix) | | | 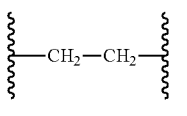 —CH$_2$—CH$_2$— |

TABLE L-continued of Lower Chains

| B | R⁴ | R⁵ | R⁶ |
|---|---|---|---|
| Ie(x) | | —(CH₂)₂—CH₂— | |
| Ie(xi) | | —(CH₂)₃—CH₂— | |

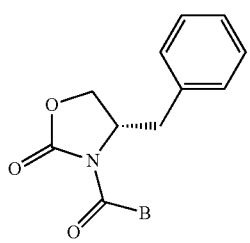

R⁴ and/or R⁵ = C₁–C₄ alkyl*
(i) Me
(ii) Et
(iii) n-Pr
(iv) i-Pr
(v) n-Bu
(vi) i-Bu
(vii) sec-Bu
(viii) tert-Bu = C₃–C₅ cycloalkyl
(ix) cyclopropyl
(x) cyclobutyl
(xi) cyclopentyl

*R⁴ and R⁵ may both be C₁–C₄ alkyl groups that are not the same. Although no examples of these embodiments are represented in these tables, their absence infers no limitation in scope.

17

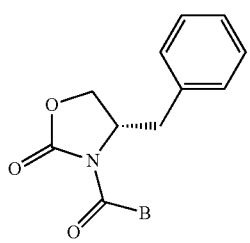

Amides

18

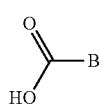

Carboxylic Acids

19

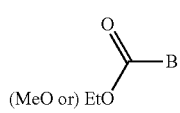

Carboxylic Esters

20

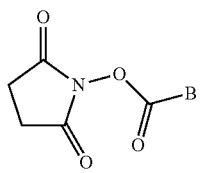

NHS Esters

21

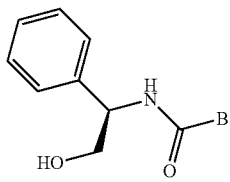

Amides

9

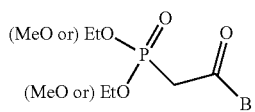

Phosphonate Esters

TABLE M of Lower Chains

| B | R⁴ | R⁵ | R⁶ |
|---|---|---|---|
| ma | H | H | |
| mb(i) | Me | H | |
| mc(i) | H | Me |  |
| md(i) | Me | Me | |
| mb(ii) | Et | H | |
| mc(ii) | H | Et | |
| md(ii) | Et | Et | |
| mb(iii) | n-Pr | H | |
| mc(iii) | H | n-Pr | |
| md(iii) | n-Pr | n-Pr | |
| mb(iv) | i-Pr | H | |
| mc(iv) | H | i-Pr | |
| md(iv) | i-Pr | i-Pr | |
| mb(v) | n-Bu | H | |
| mc(v) | H | n-Bu | |
| md(v) | n-Bu | n-Bu | |
| mb(vi) | i-Bu | H | |
| mc(vi) | H | i-Bu | |
| md(vi) | i-Bu | i-Bu | |
| mb(vii) | sec-Bu | H | |
| mc(vii) | H | sec-Bu | |
| md(vii) | sec-Bu | sec-Bu | |
| mb(viii) | tert-Bu | H | |
| mc(viii) | H | tert-Bu | |
| md(viii) | tert-Bu | tert-Bu | |
| me(ix) | | | —CH₂—CH₂— |
| me(x) | | | —(CH₂)₂—CH₂— |

TABLE M-continued of Lower Chains

| B | R⁴ | R⁵ | R⁶ |
|---|---|---|---|
| me(xi) | | | ⸺(CH₂)₃—CH₂⸺ |

$B = $ 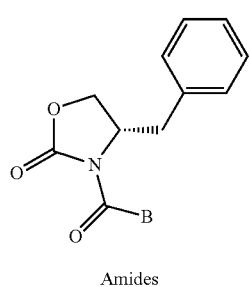

| R⁴ and/or R⁵ = | C₁-C₄ alkyl* |
|---|---|
| | (i) Me |
| | (ii) Et |
| | (iii) n-Pr |
| | (iv) i-Pr |
| | (v) n-Bu |
| | (vi) i-Bu |
| | (vii) sec-Bu |
| | (viii) tert-Bu |

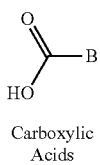 = C₃-C₅ cycloalkyl

| | |
|---|---|
| | (ix) cyclopropyl |
| | (x) cyclobutyl |
| | (xi) cyclopentyl |

*R⁴ and R⁵ may both be C₁—C₄ alkyl groups that are not the same. Although no examples of these embodiments are represented in these tables, their absence infers no limitation in scope.

17

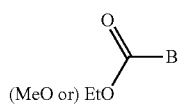

Amides

18

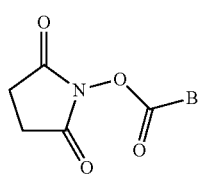

Carboxylic Acids

19

(MeO or) EtO—C(=O)—B

Carboxylic Esters

20

NHS Esters (structure shown)

21

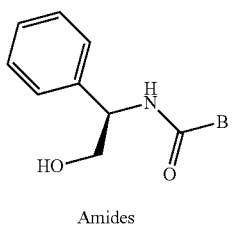

Amides

9

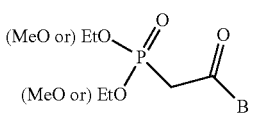

Phosphonate Esters

TABLE N of Lower Chains

| B | R⁴ | R⁵ | R⁶ |
|---|---|---|---|
| na | H | H | (phenylbutyl chain) |
| nb(i) | Me | H | |
| nc(i) | H | Me | |
| nd(i) | Me | Me | |
| nb(ii) | Et | H | |
| nc(ii) | H | Et | |
| nd(ii) | Et | Et | |
| nb(iii) | n-Pr | H | |
| nc(iii) | H | n-Pr | |
| nd(iii) | n-Pr | n-Pr | |
| nb(iv) | i-Pr | H | |
| nc(iv) | H | i-Pr | |
| nd(iv) | i-Pr | i-Pr | |
| nb(v) | n-Bu | H | |
| nc(v) | H | n-Bu | |
| nd(v) | n-Bu | n-Bu | |
| nb(vi) | i-Bu | H | |
| nc(vi) | H | i-Bu | |
| nd(vi) | i-Bu | i-Bu | |
| nb(vii) | sec-Bu | H | |
| nc(vii) | H | sec-Bu | |
| nd(vii) | sec-Bu | Sec-Bu | |
| nb(viii) | tert-Bu | H | |
| nc(viii) | H | tert-Bu | |
| nd(viii) | tert-Bu | tert-Bu | |
| ne(ix) | | | ⸺CH₂—CH₂⸺ |
| ne(x) | | | ⸺(CH₂)₂—CH₂⸺ |

TABLE N-continued of Lower Chains

| B | R⁴ | R⁵ | R⁶ |
|---|----|----|----|
| ne(xi) | | 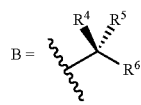 | |

$B = $ 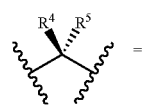

R⁴ and/or R⁵ = C₁-C₄ alkyl*
(i) Me
(ii) Et
(iii) n-Pr
(iv) i-Pr
(v) n-Bu
(vi) i-Bu
(vii) sec-Bu
(viii) tert-Bu = C₃-C₅ cycloalkyl
(ix) cyclopropyl
(x) cyclobutyl
(xi) cyclopentyl

*R⁴ and R⁵ may both be C₁—C₄ alkyl groups that are not the same. Although no examples of these embodiments are represented in these tables, their absence infers no limitation in scope.

17

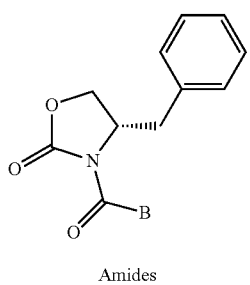

Amides

18

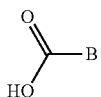

Carboxylic Acids

19

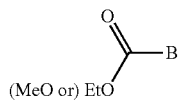

Carboxylic Esters

20

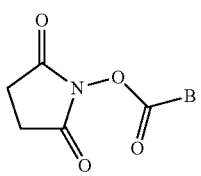

NHS Esters

21

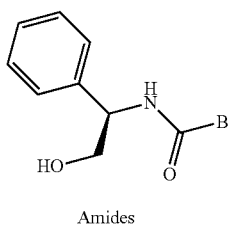

Amides

9

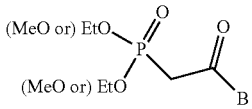

Phosphonate Esters

TABLE O of Lower Chains

| B | R⁴ | R⁵ | R⁶ |
|---|----|----|----|
| oa | H | H | 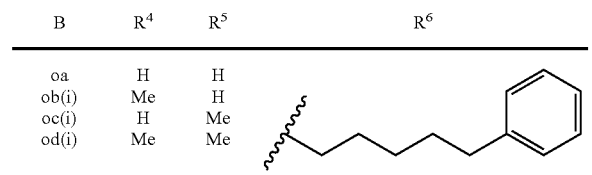 |
| ob(i) | Me | H | |
| oc(i) | H | Me | |
| od(i) | Me | Me | |
| ob(ii) | Et | H | |
| oc(ii) | H | Et | |
| od(ii) | Et | Et | |
| ob(iii) | n-Pr | H | |
| oc(iii) | H | n-Pr | |
| od(iii) | n-Pr | n-Pr | |
| ob(iv) | i-Pr | H | |
| oc(iv) | H | i-Pr | |
| od(iv) | i-Pr | i-Pr | |
| ob(v) | n-Bu | H | |
| oc(v) | H | n-Bu | |
| od(v) | n-Bu | n-Bu | |
| ob(vi) | i-Bu | H | |
| oc(vi) | H | i-Bu | |
| od(vi) | i-Bu | i-Bu | |
| ob(vii) | sec-Bu | H | |
| oc(vii) | H | sec-Bu | |
| od(vii) | sec-Bu | sec-Bu | |
| ob(viii) | tert-Bu | H | |
| oc(viii) | H | tert-Bu | |
| od(viii) | tert-Bu | tert-Bu | |
| oe(ix) | | 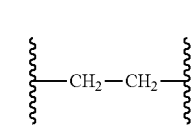 | |
| oe(x) | | 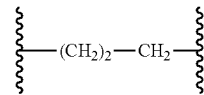 | |

TABLE O-continued of Lower Chains

| B | R⁴ | R⁵ | R⁶ |
|---|----|----|----|
| oe(xi) | | —(CH₂)₃—CH₂— | |

B = 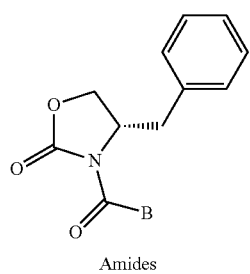

R⁴ and/or R⁵ = C₁-C₄ alkyl*
- (i) Me
- (ii) Et
- (iii) n-Pr
- (iv) i-Pr
- (v) n-Bu
- (vi) i-Bu
- (vii) sec-Bu
- (viii) tert-Bu = C₃-C₅ cycloalkyl
- (ix) cyclopropyl
- (x) cyclobutyl
- (xi) cyclopentyl

*R⁴ and R⁵ may both be C₁—C₄ alkyl groups that are not the same. Although no examples of these embodiments are represented in these tables, their absence infers no limitation in scope.

17

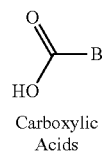

Amides

18

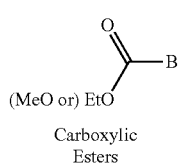

Carboxylic Acids

19

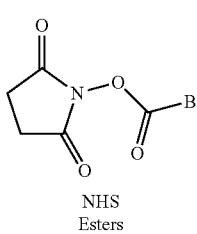

Carboxylic Esters

20

NHS Esters

21

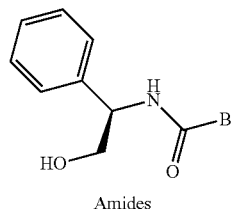

Amides

9

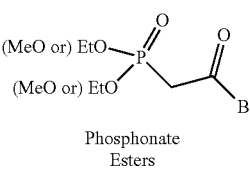

Phosphonate Esters

TABLE P/Q of Lower Chains

| B | |
|---|---|
| p | (alkyne with ethyl) |
| q | (alkyne with phenyl) |

Scheme 7a

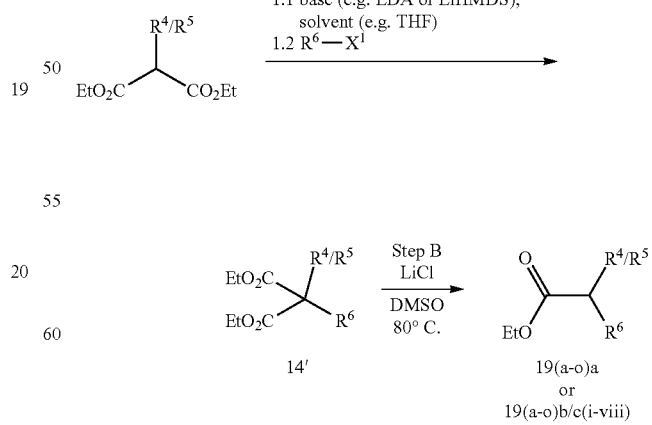

Step A
1.1 base (e.g. LDA or LiHMDS), solvent (e.g. THF)
1.2 R⁶—X¹

Step B
LiCl
DMSO
80° C.

14'

19(a-o)a
or
19(a-o)b/c(i-viii)

X¹ = leaving group
(e.g. iodide, bromide, or triflate)

Scheme 7b
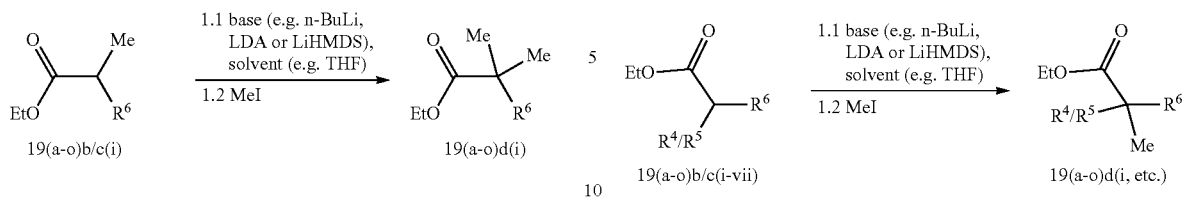
$X^1$ = leaving group
(e.g. bromide, iodide, or triflate)
Scheme 7c
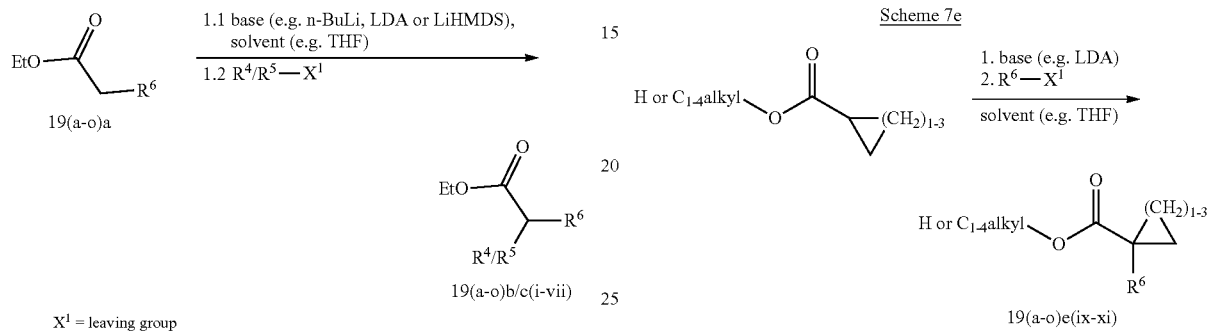
Scheme 7d
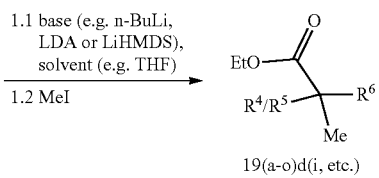
Scheme 7e
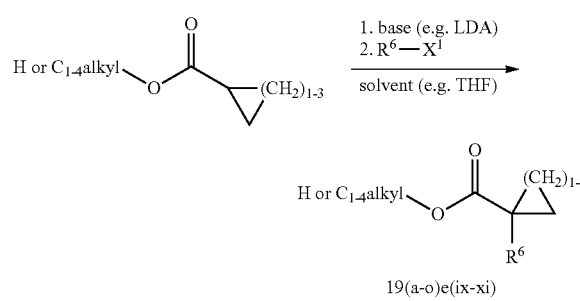
Scheme 7f
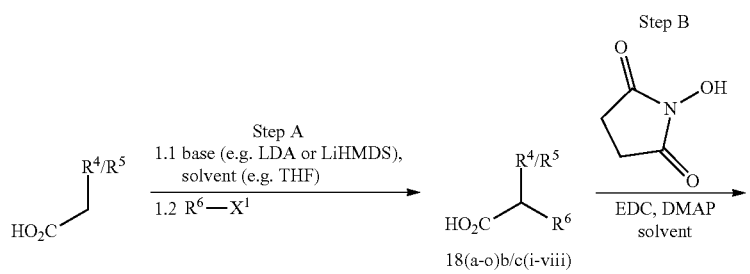
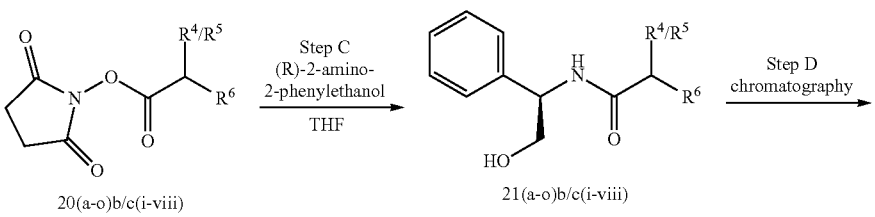
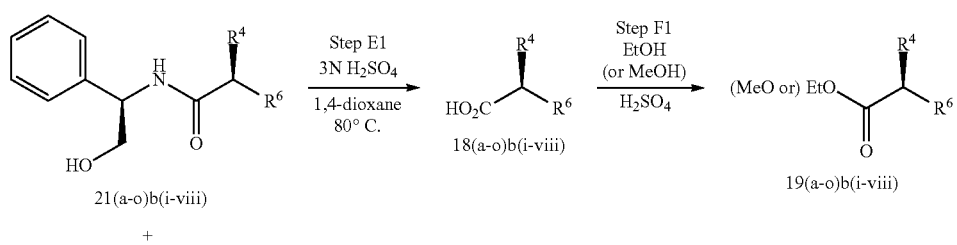

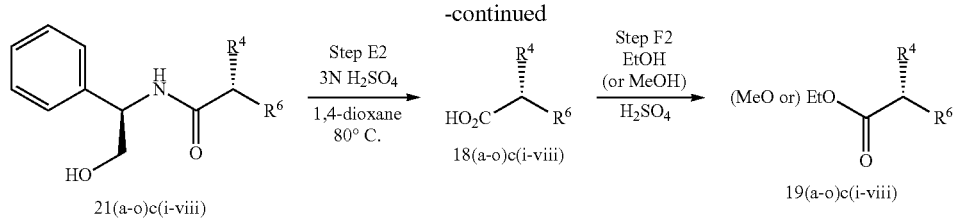
$X^1$ = leaving group (e.g. bromide, iodide, or triflate)
Scheme 7g
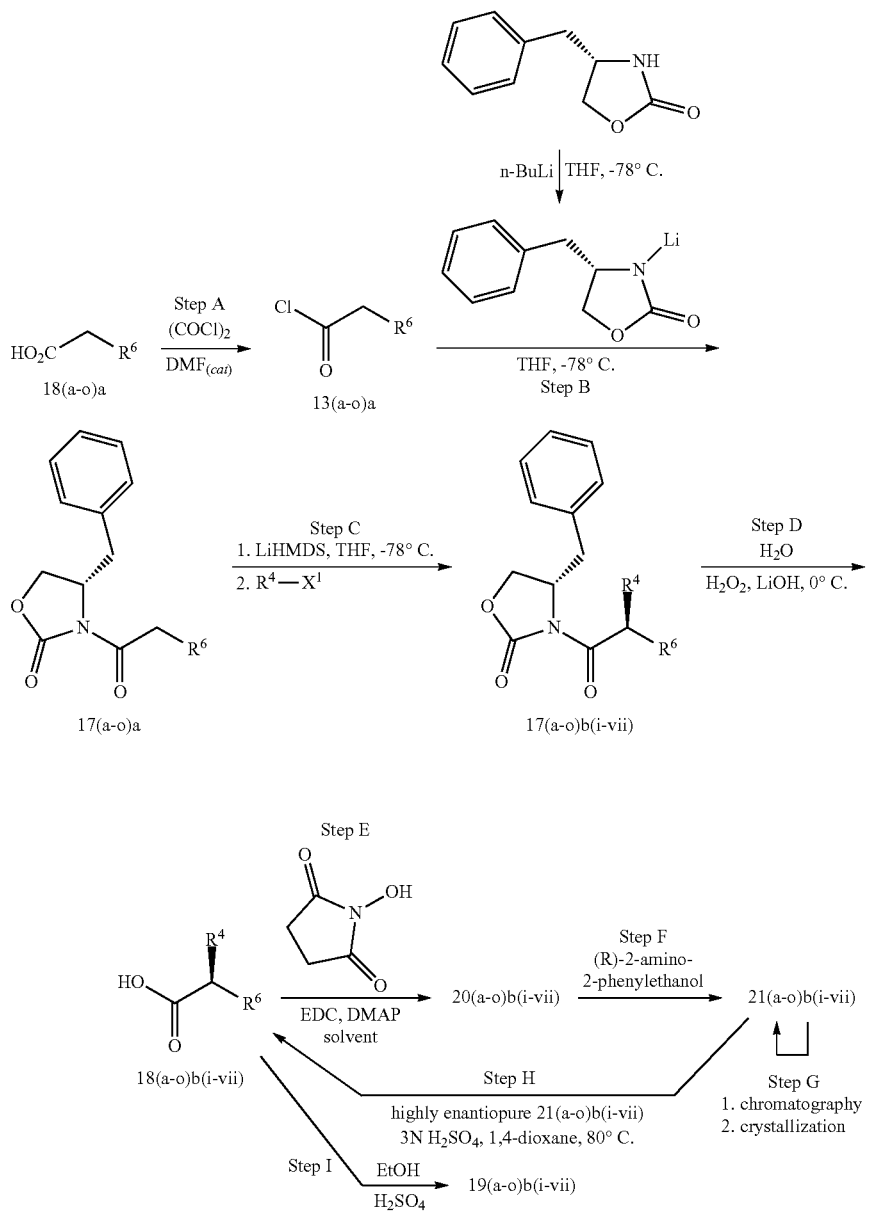
$X^1$ = leaving group (e.g. bromide, iodide, or triflate)

Scheme 8

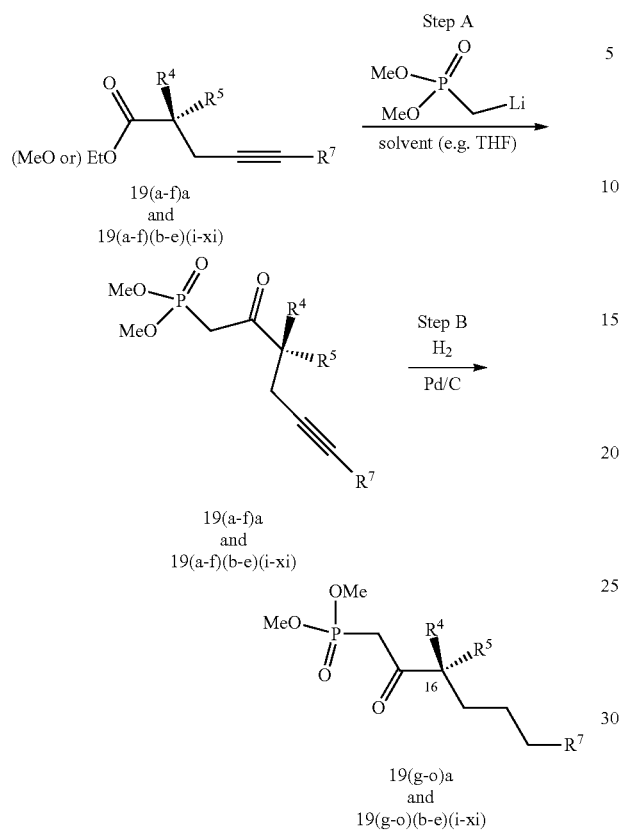

The present invention also provides the methods of synthesis of (R)-3,3-difluoro-5-(protected hydroxymethyl)pyrrolidin-2-one (5), the α,α-difluoro-γ-lactam scaffold which is one of the compounds of the present invention and common intermediate to additional compounds of the present invention that may be derived from (R)-5-(hydroxymethyl)pyrrolidin-2-one (0) as illustrated in Scheme 9. The simultaneous protection of the lactam NH and the exocyclic hydroxyl groups of compound 0 can be accomplished by the acid catalyzed incorporation (step xviii) of a ketal like

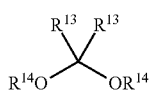

wherein $R^{13}$ and $R^{14}$ are defined as above to provide protected intermediate 1. Subsequent two step a carbonyl deprotonation followed by addition of electrophilic fluorine using NFSi (step xix) in a one-pot reaction technique affords the α,α-difluoropyrrolidone intermediate 2. Deprotection of 2 by an acid catalysis reaction, namely a strongly acidic sulfonic acid cation exchange resin, provides the intermediate 4. The hydroxyl moiety of 4 may be protected (step xxi) to give the lactam scaffold ready for the nitrogen-carbon bond forming reaction and installation of the upper chain of compounds of the present invention.

Scheme 9

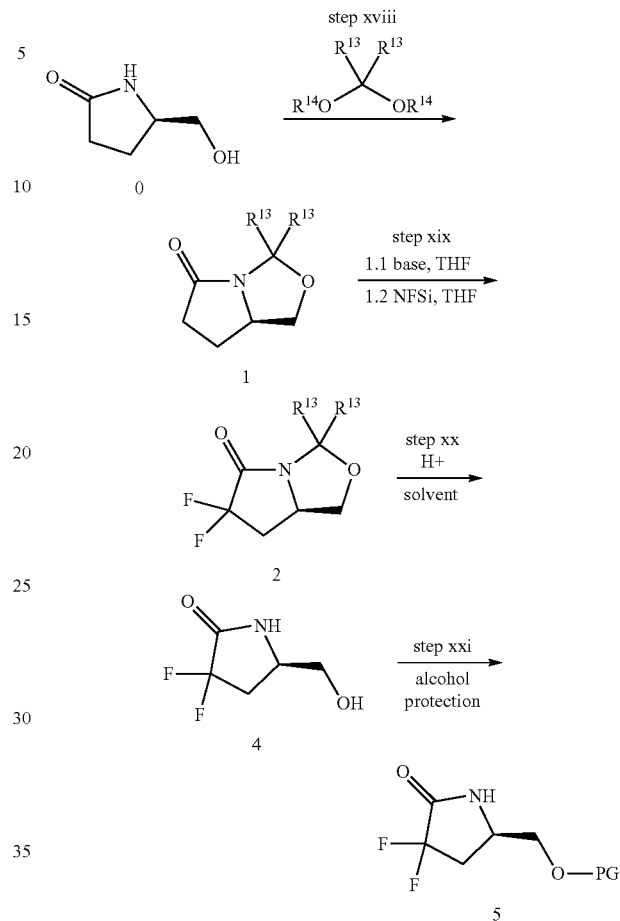

The present invention also provides the methods for constructing the compounds 8 from the components 3 and 5. N-alkylation (Scheme 10, step xxii) of scaffold 5 with an alkylating reagent $X^1$-$L^1$-$R^1$, wherein $X^1$, $L^1$, and $R^1$ are described above, such as 3a or 3b also described above affords intermediate 6. Alcohol deprotection (step xxiii) and subsequent controlled alcohol oxidation (step xxiv) provides the corresponding aldehyde intermediates 8 that may be employed in the subsequent olefination step.

Scheme 10

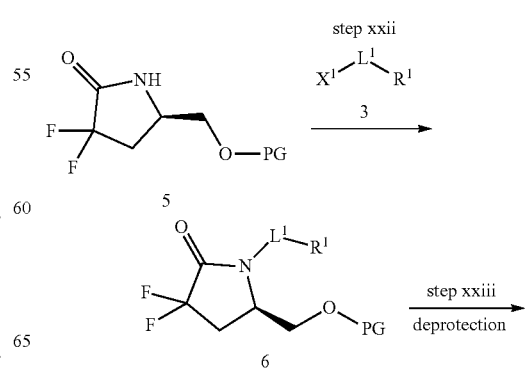

75
-continued

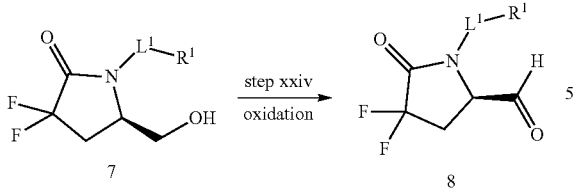

76
Preparation of
5-(3-bromopropyl)thiophene-2-carboxylic acid

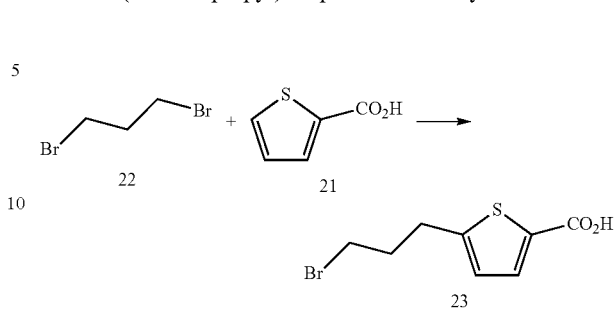

The present invention provides the methods of synthesis of compounds of Figure (IA) (11) from compounds 8 and 9. Utilizing a Horner-Emmons-Wadsworth type procedure (Scheme 11, step xxv), the lower chain may be installed by the coupling of an aldehyde intermediate 8 for which their preparations are described and illustrated above and an organic phosphonate ester such as those also described and illustrated above to produce an α,β-unsaturated ketone compound intermediate 10. The C15-oxo group may be chemo- and stereoselectively reduced to the corresponding C15-hydroxyl group as a stereoisomeric alcohol mixture (two or more diastereomers, not necessarily of equal quantity). The stereoisomeric alcohol mixture may be subsequently separated by HPLC to provide a pure, single C15α-hydroxy diastereomer 11 (i.e., Formula (IA)) and a pure, single C15β-hydroxy diastereomer (step xxvi).

Scheme 11

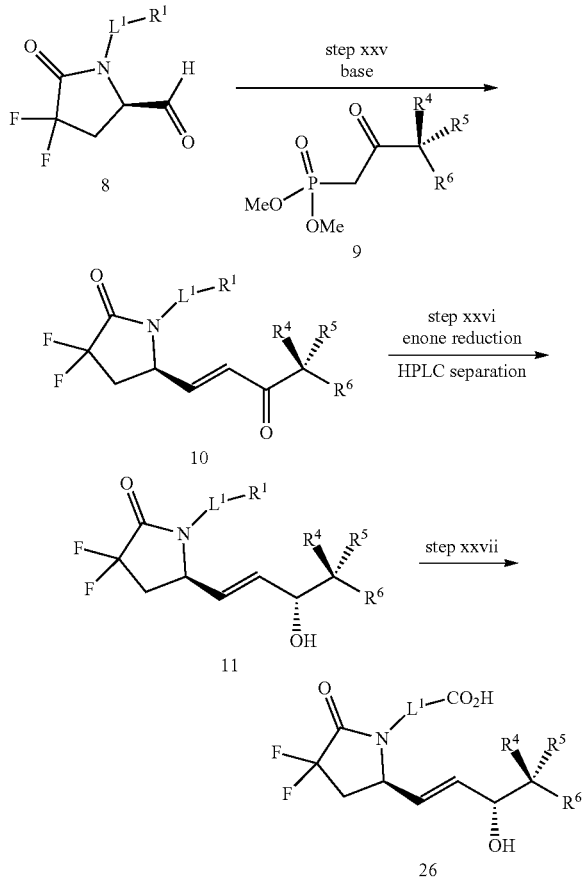

The following examples are not intended to limit the scope of the present invention.

To a −78° C. solution consisting of thienoic acid (10.0 g, 78 mmol) in THF (150 mL) was added LDA (85 mL, 170 mmol, 2$\underline{M}$) dropwise over 20 minutes, and the reaction was stirred 40 minutes. To the reaction mixture was then added dibromopropane (23.8 g, 117 mmol) in 1 portion, and the reaction was allowed to warm to room temperature and stirred for 3 days. To the reaction mixture was added 50 ml each a saturated aqueous solution of ammonium chloride, a saturated aqueous solution of sodium chloride, and 6$\underline{N}$ HCl. The organic material was extracted with ethyl acetate and the organic layer was dried over sodium sulfate, filtered and concentrated to give 24.0 g of the title compound as a yellow oil. The product was used without purification. TLC R$_f$ 0.5 (solvent system: 30:70:1 v/v ethyl acetate:hexanes:acetic acid).

Preparation of methyl
5-(3-bromopropyl)thiophene-2-carboxylate (3b)

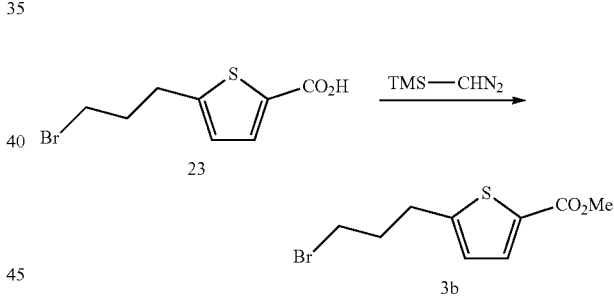

To a 0° C. solution consisting of 5-(3-bromopropyl)thiophene-2-carboxylic acid (24 g, 78 mmol) in ethyl acetate (150 mL) and methanol (15 mL) was added TMS-diazomethane (50 mL, 100 mmol, 2$\underline{M}$) dropwise over 1 hour, then allowed to warm to room temperature and stirred for 16 hours. The reaction mixture was concentrated under reduced pressure without workup. The residue was purified by silica gel chromatography eluting with ethyl acetate-heptanes (1:80 v:v) to afford 4.95 g (24% over two steps) of the title compound as a white solid; TLC R$_f$ 0.45 (solvent system: 15:85 v/v ethyl acetate:hexanes); MS (ESI$^+$) m/z 263, 265 (isotopic bromines, each (M+H)$^+$); $^1$HNMR (CDCl$_3$) δ 7.5 (d, 1H), 6.7 (d, 1H), 3.75 (s, 3H), 3.3 (t, 2H), 2.9 (t, 2H), 2.1-2.0 (m, 2H).

Scheme 7g, Step B: Preparation of (S)-4-benzyl-3-(5-phenylpentanoyl)oxazolidin-2-one (17ma)

To a −78° C. solution of (S)-4-benzyloxazolidin-2-one (0.9 g, 5.08 mmol) in THF (20 mL) was slowly added n-butyllithium (3.5 mL, 5.59 mmol, 1.6$\underline{M}$ solution in hexane). The mixture was stirred at −78° C. for 2 hours, at which time 5-phenylpentanoyl chloride (1 g, 5.08 mmol, prepared by treatment of 5-phenylpentanoic acid with oxalyl chloride and catalytic DMF) was added slowly. The reaction mixture was stirred at −78° C. for 2 hours and then allowed to come to room temperature overnight. The mixture was acidified with 5% KHSO$_4$ and extracted twice with ethyl acetate. The organic phase was washed with brine, dried over sodium sulfate, filtered and concentrated under vacuum. The residue was purified by silica gel chromatography eluting with ethyl acetate-heptane (25:75 v/v) to give 1.4 g (82%) of the title compound as a clear oil; TLC R$_f$0.40 (solvent system: 25:75 v/v ethyl acetate-heptane); MS (ESI$^+$) m/z 337.41 g (M+H)$^+$, 360.2 (M+Na)$^+$.

Scheme 7g, Step C: Preparation of (S)-4-benzyl-3-((S)-2-methyl-5-phenylpentanoyl)oxazolidin-2-one (17mb(i))

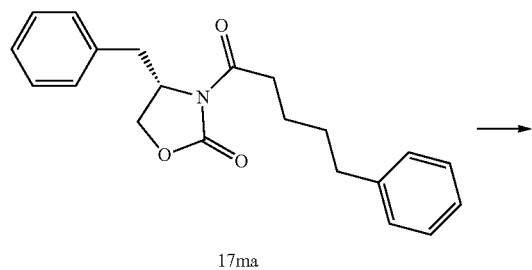

17ma

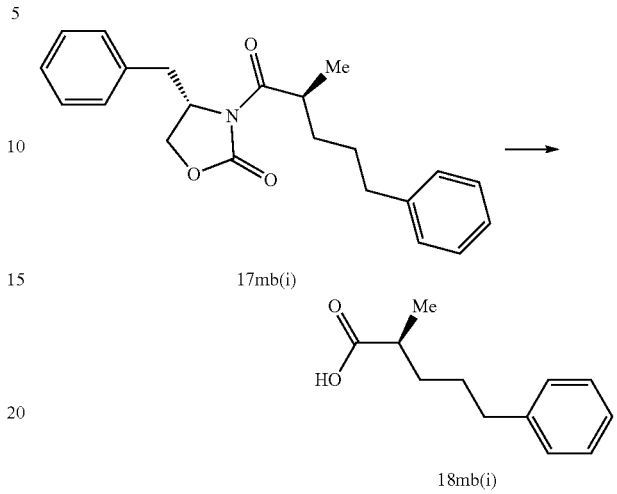

17mb(i)

To a −78° C. solution of (S)-4-benzyl-3-(5-phenylpentanoyl)oxazolidin-2-one (1.24 g, 3.68 mmol) in THF (20 mL) was slowly added lithium bis-(trimethylsilyl)amide (4.41 mL, 4.41 mmol, 1$\underline{M}$ solution in THF). The mixture was stirred at −78° C. for 1 hour, at which time, iodomethane (0.27 mL, 4.23 mmol) was added slowly, and the mixture was allowed to come to room temperature and stirred overnight. The mixture was acidified with 5% KHSO$_4$ and extracted twice with ethyl acetate. The organic layer was washed twice with brine, dried over sodium sulfate, filtered and concentrated under vacuum. The residue was purified by silica gel chromatography eluting with ethyl acetate-heptane (25:75 v/v) to give 563 mg (43.6%) of the title compound as a clear oil; TLC R$_f$0.53 (solvent system: 25:75 v/v ethyl acetate-heptane; MS (ESI$^+$) m/z 352.3 (M+H)$^+$374.2 (M+Na)$^+$.

Scheme 7g, Step D: Preparation of (S)-2-methyl-5-phenylpentanoic acid (18mb(i))

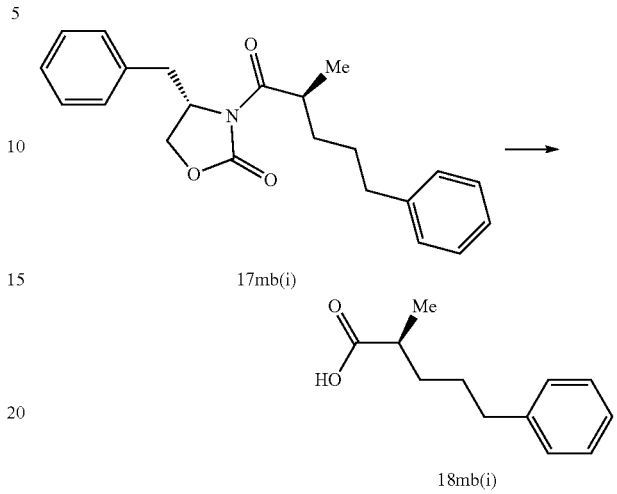

To solution of (S)-4-benzyl-3-((S)-2-methyl-5-phenyl-pentanoyl)oxazolidin-2-one was added water and the mixture was cooled to 0° C., added hydrogen peroxide and lithium hydroxide and stirred for 4 hours. The reaction mixture was acidified with 5% KHSO$_4$ and extracted twice with ethyl acetate, the organic layer was washed twice with brine, dried over sodium sulfate and concentrated under vacuum. The residue was purified by silica gel chromatography eluting with ethyl acetate-hepatane-acetic acid (25:75:0.4) to give 293 mg (95%) of the title compound as a colorless oil; TLC R$_f$0.35 (solvent system: 25:75:0.4 v/v/v ethyl acetate-heptane-acetic acid); HPLC retention time 12.08 min, stationary phase: Chiralpak IA 4.6×25 mm 5 g, ultraviolet detector at 210 nm, mobile phase: 1 mL/min 99:1:0.1 heptane: 2-propanol: acetic acid, 97.22% (S), 2.78% (R).

Scheme 7g, Step E: Preparation of (S)-2,5-dioxopyrrolidin-1-yl 2-methyl-5-phenylpentanoate (20mb(i))

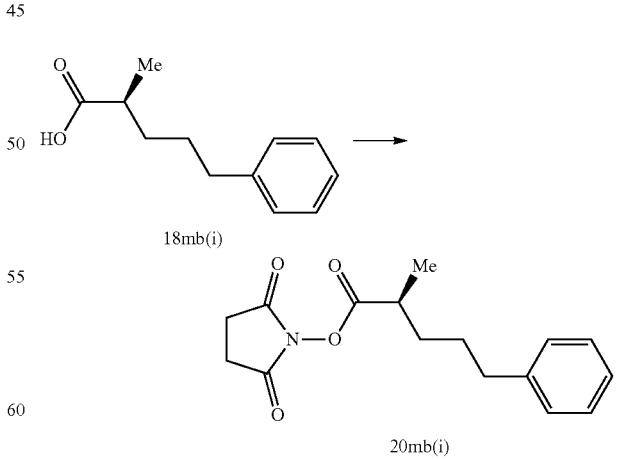

To (S)-2-methyl-5-phenylpentanoic acid (290 mg, 1.51 mmol) in dichloromethane (20 mL) was added N-hydroxysuccinimide (191 mg, 1.66 mmol), 4-dimethylaminopyridine (203 mg, 1.66 mmol) and 1-ethyl-(3-dimethylaminopropyl)carbodiimide hydrochloride (318 mg, 1.66 mmol) and the mixture stirred for 2 hours at room temperature. The reaction mixture was used in the next step.

Scheme 7g, Step F and G: Preparation of (S)—N—((R)-2-hydroxy-1-phenylethyl)-2-methyl-5-phenyl-pentanamide (21)

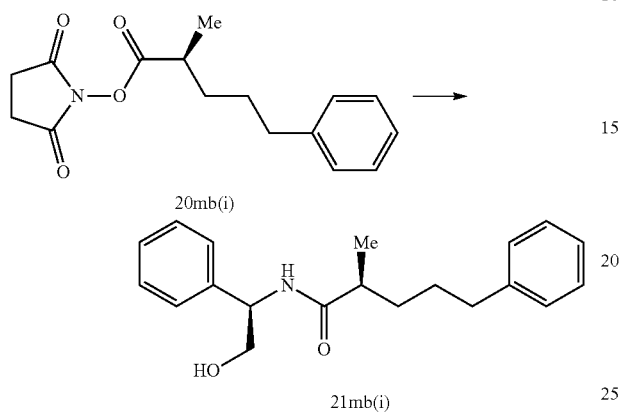

To the previous mixture from above was added R-(−)-2-phenylglycinol, and the mixture stirred overnight. The mixture was filtered and washed with THF and the filtrate was then concentrated under vacuum. The residue was purified by silica gel chromatography eluting with ethyl acetate-heptane (60:40 v/v). The solid obtained from the chromatography was crystallized from ethyl acetate-heptane to give 198 mg (42%) of the title compound as a white solid; TLC $R_f$ 0.21 (solvent system: 60:40 v/v ethyl acetate-heptane; HPLC retention time 14.68 minutes, stationary phase: Gemini, 5μ C18 250×4.6 mm, ultraviolet wavelength of 210 nm, mobile phase: 1 mL/min, 60:40:0.1 methanol-water-acetic acid, 100% (S); MS (ESI$^+$) m/z 312.2 (M+H)$^+$, 334.1 (M+Na)$^+$.

Scheme 7g, Step H: Preparation of (S)-(+)-2-methyl-5-phenylpentanoic acid (18mb(i))

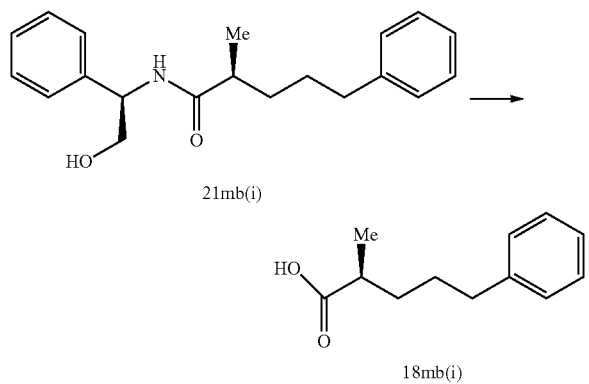

To a solution of (S)—N—((R)-2-hydroxy-1-phenylethyl)-2-methyl-5-phenylpentanamide (3.5 g, 11.24 mmol) in 1,4-dioxane (80 mL) was added sulfuric acid (36 mL, 3N solution in water) and the mixture was stirred overnight at 80° C. The reaction mixture was extracted with ethyl acetate three times and the organic layers were combined, dried over sodium sulfate, filtered and concentrated under vacuum. The residue was purified by silica gel chromatography eluting with ethyl acetate-hepatane-acetic acid (30:70:0.4 v/v/v) to give 2.4 g (quant) of the title compound as a clear oil; $R_f$ 0.48 (solvent system: 30:70:0.4 v/v/v ethyl aceate-hepatane-acetic acid; HPLC retention time 26.0 minutes; Chiralpak IA, 5μ, 4.6×25 mm, ultraviolet detector at 208 nm 0.75 ml/min 99:1:0.5 v/v heptanes-2-propanol-acetic acid; MS (ESI$^+$) m/z 191.1 (M−H)$^+$; $^1$H-NMR (CDCl$_3$) δ 7.33-7.27 (m, 2H), 7.22-7.16 (m, 3H), 2.67-2.60 (m, 2H), 2.56-2.46 (m, 1H), 1.80-1.60 (m, 3H), 1.59-1.36 (m, 1H), 1.25-1.14 (m, 3H); $[\alpha]^T_\lambda = \alpha/cl$, $[\alpha]^{21.9}_D = +0.089/(0.01501\ g/1.5\ mL)(0.5) = +17.79°$ (c=1, CHCl$_3$).

Scheme 7g, Step I: Preparation of (S)-(+)-ethyl 2-methyl-5-phenylpentanoate (19mb(i))

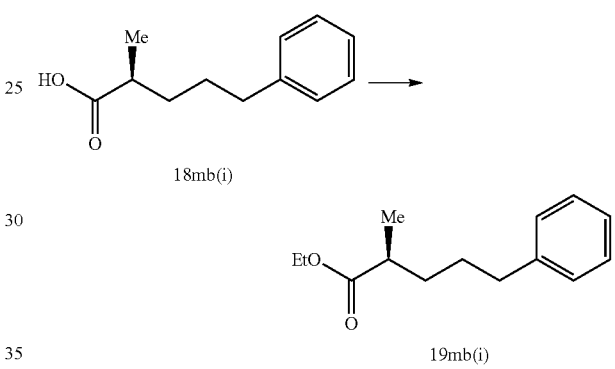

To a solution consisting of (S)-(+)-2-methyl-5-phenylpentanoic acid (2.3 g, 11.96 mmol) in ethanol (200 mL) was added 4 drops of sulfuric acid and the mixture refluxed overnight. The mixture was cooled concentrated under vacuum. The residue was diluted with ethyl acetate and washed twice with brine. The organic layer was dried over sodium sulfate, filtered and concentrated under vacuum to give 2.4 g (91%) of the title compound as a clear oil; TLC $R_f$ 0.66 (solvent system: 15:85:1 v/v/v ethyl acetate-heptane-acetic; MS (ESI$^+$) m/z 221.2 (M+H)$^+$; $^1$H-NMR (CDCl$_3$) δ 7.29-7.25 (m, 2H), 7.21-7.13 (m, 3H), 4.12 (q, J=6.96 Hz, 2H), 2.64-2.57 (m, 2H), 2.48-2.39 (m, 1H), 1.75-1.54 (m, 3H), 1.52-1.41 (m, 1H), 1.24 (t, J=7.14 Hz, 3H) 1.16-1.11 (m, 3H); $[\alpha]^T_\lambda = \alpha/cl$; $[\alpha]^{21.9}_D = +0.101/(0.01506\ g/1.5\ ml) (0.5) = +20.12°$ (c=1, CHCl$_3$).

Scheme 6: Preparation of (S)-(+)-dimethyl (3-methyl-2-oxo-6-phenylhexyl)phosphonate (9mb(i))

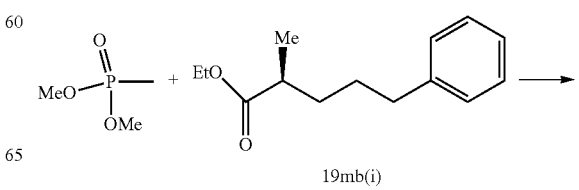

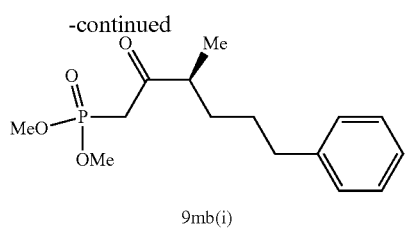

9mb(i)

To a −78° C. solution consisting of dimethyl methylphosphonate (23.37 g, 188.4 mmol) in THF (400 mL) was slowly added n-butyllithium (112 mL, 179.0 mmol, 1.6M solution in hexane). The mixture was stirred for 30 minutes, at which time, (S)-(+)-ethyl 2-methyl-5-phenylpentanoate (28.1 g, 94.2 mmol) in THF (100 mL) was added slowly, and the mixture stirred at −78° C. for 2 hours and then allowed to come to room temperature overnight. The reaction mixture was treated with 5% KHSO$_4$ and extracted with ethyl acetate three times. The organic layer was washed twice with 50:50 water-brine and the organic layer was dried over sodium sulfate, filtered and concentrated under vacuum. The residue was purified by silica gel chromatography eluting with ethyl acetate-hepatane (60:40 v/v) to give 11.9 g of the title compound as a clear oil, pure of unrelated components; TLC R$_f$0.22 (solvent system: 60:40 v/v ethyl acetate-heptane); HPLC retention time 14.5 minutes, 5μ Chiralpak IA 250×4.6 mm, ultraviolet detector at 210 nm, 1 ml/min, chiral purity 97.8% (S), 2.19% (R); MS (ESI$^-$) m/z 297.1 (M−H)$^-$; $^1$H NMR (CDCl$_3$) δ 7.28-7.21 (m, 2H), 7.17-7.12 (m, 3H), 3.76-3.71 (m, 6H), 3.10 (d, J=2.20 Hz, 1H), 3.04 (d, J=2.20 Hz, 1H), 2.79-2.70 (m, 1H), 2.54-2.62 (m, 2H), 1.74-1.54 (m, 3H), 1.42-1.24 (m, 1H), 1.07 (d, J=6.96 Hz, 3H); $[\alpha]^T_\lambda$=α/cl, $[\alpha]^{21.9}_D$=+0.084/(0.0169 g/1.5 mL)(0.5)=+14.91° (c=1.13, CHCl$_3$).

The chromatography also provided 8.3 g of 95% based on visual observation of TLC; chiral purity 98.19% (S), 1.81% (R).

Alternative preparation of (S)-(+)-dimethyl (3-methyl-2-oxo-6-phenylhexyl)phosphonate (9mb(i))

Scheme 7f, Step A: Preparation of (±)-2-methyl-5-phenylpentanoic acid (18mb(i))

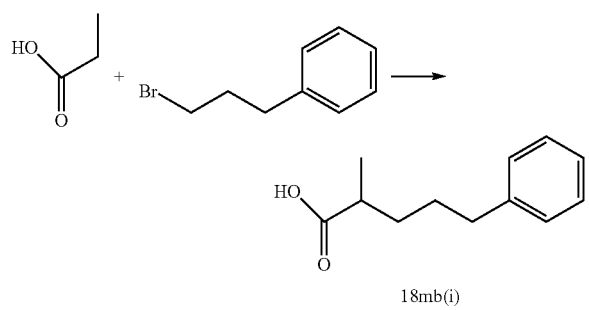

18mb(i)

To a solution of diisopropylamine (218.25 mL, 1557.3 mmol) in THF (400 mL) at −50° C. was added n-butyllithium (628 mL, 392.5 mmol, 1.6M solution in hexane). The mixture was stirred for 5 minutes then was allowed to warm to −20° C. To the reaction mixture was added a solution consisting of propionic acid (44.67 g, 603 mmol) in HMPA (102 mL) drop wise. The mixture was stirred at room temperature for 30 minutes, cooled to 0° C. and 1-bromo-3-phenylpropane (100 g, 502 mmol) in THF (200 mL) was added and the mixture stirred at room temp for 2 hours. The reaction mixture was diluted with water and extracted with ethyl acetate. The aqueous layer was separated and then acidified with 2M HCl until acidic. The aqueous layer was then extracted 3 times with ethyl acetate, and the organic layers were combined and dried over sodium sulfate, filtered, and concentrated to give 105 g (quant) of a clear oil; TLC R$_f$0.44 (solvent system: 25:75:1 v/v/v ethyl acetate-heptane-acetic acid.

Scheme 7f, Step B: Preparation of (f)-2,5-dioxopyrrolidin-1-yl 2-methyl-5-phenylpentanoate (20mb(i))

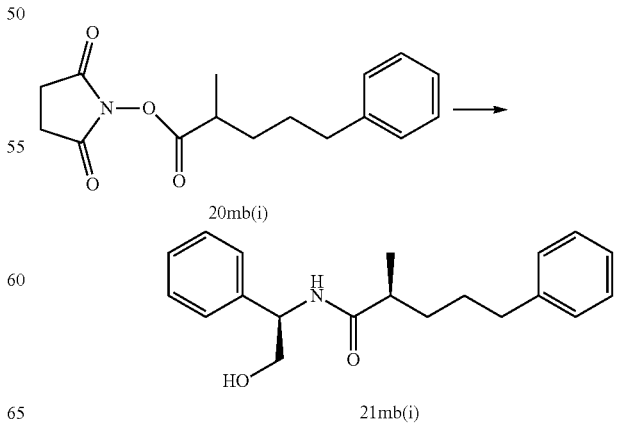

To a mixture consisting of (+)-2-methyl-5-phenylpentanoic acid (105.6 g, 549.1 mmol) in dichloromethane (800 mL) was added N-hydroxysuccinimide (69.5 g, 604.0 mmol), 4-dimethylaminopyridine (73.8 g, 604.04 mmol) and 1-ethyl-(3-dimethylaminopropyl) carbodiimide hydrochloride (115.8 g, 604.0 mmol) and the mixture stirred overnight at room temperature. The mixture was extracted with dichloromethane and washed twice with brine, dried over sodium sulfate, filtered, and concentrated under vacuum. The residue was purified by silica gel chromatography eluting with ethyl acetate-heptane (30:70 v/v) to afford 85.6 g (54%) of the title compound; TLC R$_f$0.32 (solvent system 25:75 v/v ethyl acetate-heptane.

Scheme 7f, Steps C and D: Preparation of (S)—N—((R)-2-hydroxy-1-phenylethyl)-2-methyl-5-phenylpentanamide (21mb(i))

To a solution consisting of (±)-2,5-dioxopyrrolidin-1-yl 2-methyl-5-phenyl pentanoate (85.6 g, 295.9 mmol) in THF (3000 mL) at 48° C. was added R-(−)-2-phenylglycinol (65.9 g, 480.4 mmol, Bridge Organics) in portions, and the mixture stirred at 48° C. for 40 hours. The white precipitate was filtered from the reaction mixture and washed with THF. The filtrate was concentrated under vacuum and the residue, consisting of the diastereomeric pair, was chromatographed on silica gel eluting with ethyl acetate-heptane (50:50 v/v). The pure diastereomer, the title compound, was obtained, 31.3 g (34%), as a colorless solid; TLC $R_f$ 0.205 (solvent system: 50:50 v/v ethyl acetate-heptane); HPLC retention time 15.1 minutes, stationary phase: Gemini 5µ C18 250× 4.6 mm, ultraviolet detector at 210 nm, mobile phase: 1 mL/min, 60:40:0.1 v/v methanol-water-acetic acid.

Scheme 7f, Steps E and F and Scheme 6: Preparation of (S)-(+)-dimethyl (3-methyl-2-oxo-6-phenylhexyl)phosphonate (9mb(i))

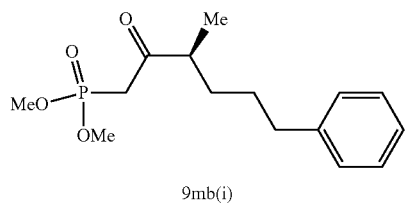 [SMILES: COP(=O)(CC(=O)[C@@H](C)CCCc1ccccc1)OC]

9mb(i)

(S)-(+)-Dimethyl (3-methyl-2-oxo-6-phenylhexyl)phosphonate (9mb(i)) is prepared in three steps in the same manner as that described above from (S)—N—((R)-2-hydroxy-1-phenylethyl)-2-methyl-5-phenylpentanamide (21mb(i)).

Preparation of (R)—N—((R)-2-hydroxy-1-phenylethyl)-2-methyl-5-phenylpentanamide (21mc(i))

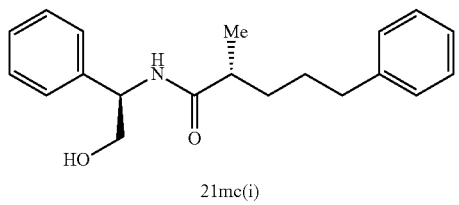 [SMILES: C[C@H](CCCc1ccccc1)C(=O)N[C@@H](CO)c1ccccc1]

21mc(i)

(R)—N—((R)-2-Hydroxy-1-phenylethyl)-2-methyl-5-phenylpentanamide was prepared in the same manner as (S)—N—((R)-2-hydroxy-1-phenylethyl)-2-methyl-5-phenylpentanamide. Silica gel chromatography of the diastereomeric pair described above in Scheme 7f, Steps C and D reaction gave 30.2 g (33%) of the title compound as a white solid; TLC $R_f$ 0.33 (solvent system: 50:50 v/v ethyl acetate-heptane); HPLC retention time 13.25 minutes, Gemini 5µ C18 250×4.6 mm, at ultraviolet wavelength of 210 nm, 1 mL/min, 60:40:0.1 methanol-water-acetic acid, chiral purity 99.36% (R), 0.64% (S); $[\alpha]^T_\lambda = \alpha/cl$, $[\alpha]^{21.9}_D = -0.066/(0.01573 \text{ g}/2 \text{ mL})(0.5) = -16.78°$ (c=0.7865, CHCl$_3$).

Preparation of (R)-(+)-2-methyl-5-phenylpentanoic acid (18mc(i))

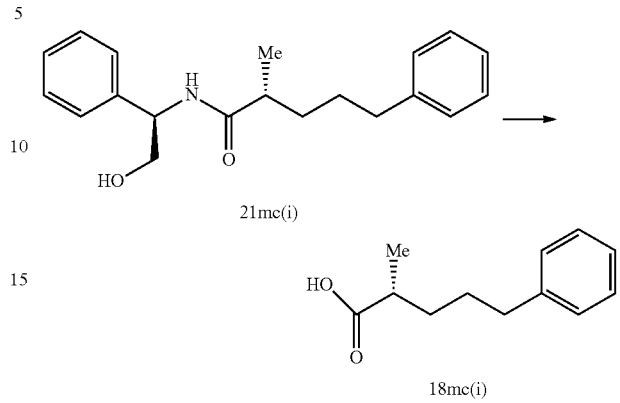

(R)-(+)-2-Methyl-5-phenylpentanoic acid was prepared in the same manner as (S)-2-methyl-5-phenylpentanoic acid. The residue was purified by silica gel chromatography eluting with ethyl acetate-hepatane-acetic acid (20:80:0.4 v/v/v) to give 20.8 g of the title compound as a clear oil; TLC $R_f$ 0.51 (solvent system: 30:70:1 v/v/v ethyl aceate-hepatane-acetic acid; HPLC retention time 24.46 min; Chiralpak IA 4.6×25 mm 5µ, at a wavelength of 208 nm 0.75 mL/min, 99:1:0.5 heptane: 2-propanol: acetic acid, chiral purity 99.32% (R), 0.68% (S); MS (ESI$^-$) m/z 191.1 (M−H)$^-$; $^1$H-NMR (CDCl$_3$) δ 7.31-7.26 (m, 2H), 7.21-7.15 (m, 3H), 2.67-2.57 (m, 2H), 2.54-2.44 (m, 1H), 1.79-1.59 (m, 3H), 1.58-1.41 (m, 1H), 1.18 (d, J=6.96 Hz, 3H).

Preparation of (R)-ethyl 2-methyl-5-phenylpentanoate (19mc(i))

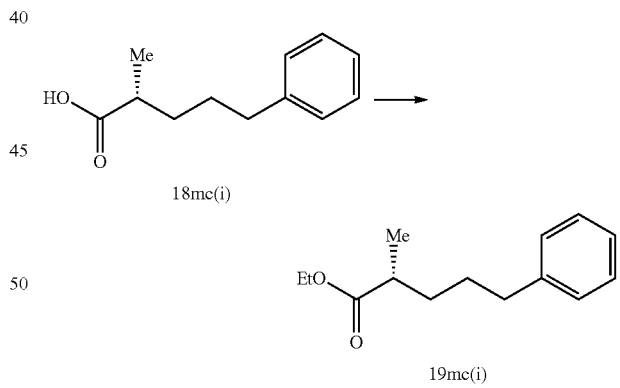

(R)-Ethyl 2-methyl-5-phenylpentanoate was prepared in the same manner as (S)-ethyl 2-methyl-5-phenylpentanoate. The residue was purified by silica gel chromatography eluting with ethyl acetate-heptane (5:95 v/v) to give 21.0 g (88%) of the title compound as a clear oil; TLC $R_f$ 0.66 (solvent system: 15:85:1 v/v/v ethyl acetate-heptane-acetic acid; MS (ESI$^+$) m/z 221.2 (M+H)$^+$; $^1$H-NMR (CDCl$_3$) δ 7.32-7.26 (m, 2H), 7.20-7.14 (m, 3H), 4.11 (q, J=7.32 Hz, 2H), 2.64-2.57 (m, 2H), 2.48-2.39 (m, 1H), 1.75-1.53 (m, 3H), 1.52-1.41 (m, 1H), 1.27-1.21 (m, 3H), 1.13 (d, J=6.96 Hz, 3H); $[\alpha]^T_\lambda = \alpha/cl$, $[\alpha]^{21.9}_D = -0.114/(0.01771 \text{ g}/1.5 \text{ mL})(0.5) = -19.31°$ (c=1.18, CHCl$_3$).

Scheme 6: Preparation of (R)-dimethyl (3-methyl-2-oxo-6-phenylhexyl)phosphonate (9mc(i))

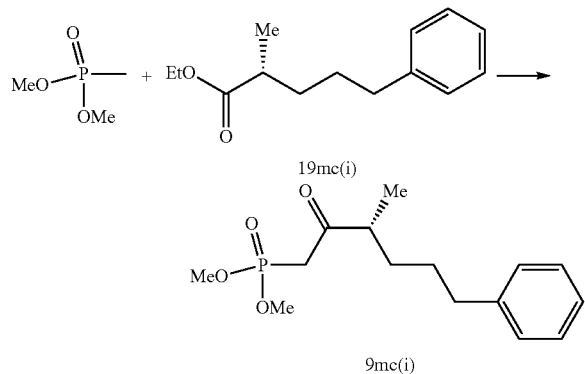

9mc(i)

(R)-Dimethyl (3-methyl-2-oxo-6-phenylhexyl)phosphonate was prepared in the same manner as (S)-dimethyl (3-methyl-2-oxo-6-phenylhexyl)phosphonate. The residue was purified by silica gel chromatography eluting with ethyl acetate-heptane (70:30 v/v) to give 83 mg (66%) of the title compound as a colorless oil; TLC $R_f$ 0.22 (solvent system: 70:30 v/v ethyl acetate-heptane); HPLC retention time 12.36 min, 5μ Chiralpak OJ-H 4.6×250 mm, at ultraviolet wavelength of 210 nm, 90:10:0.1 heptane:ethanol:acetic acid 1 mL/min, chiral purity 100% (R); MS (ESI$^-$) m/z 297.1 (M–H)$^-$; $^1$H NMR (CDCl$_3$) δ 7.29 (d, J=6.51 Hz, 2H), 7.22-7.16 (m, 3H), 3.77 (d, J=11.35 Hz, 3H), 3.78 (d, J=11.35 Hz, 3H), 3.13 (d, J=1.83 Hz, 1H), 3.08 (d, J=1.83 Hz, 1H), 2.78 (d, J=6.96 Hz, 1H), 2.67-2.56 (m, 2H), 1.61-1.52 (m, 3H), 1.45-1.32 (m, 1H), 1.11 (d, J=6.96 Hz, 3H); $[\alpha]^T_\lambda$=α/cl, $[\alpha]^{21.9}_D$=–0.080/(0.01742 g/1.5 mL) (0.5) =–13.78° (c=1.16, CHCl$_3$).

Scheme 7a, Steps A and B and Scheme 6: Preparation of (S)-(+)-dimethyl (3-methyl-2-oxooct-5-yn-1-yl)phosphonate (9bb(i))

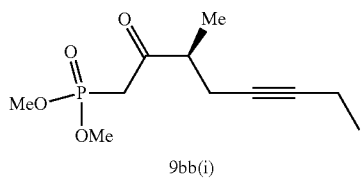 [SMILES: CCC#CC[C@H](C)C(=O)CP(=O)(OC)OC]

9bb(i)

(S)-(+)-Dimethyl (3-methyl-2-oxooct-5-yn-1-yl)phosphonate (9bb(i)) was prepared by following the sequence of reaction steps described in Scheme 7a, 7f and Scheme 6. The intermediate 2-methylhept-4-ynoic acid (18bb(i)) was prepared according to a method described in WO 2011/003058 A1 (Scheme 7a, Steps A and B, followed by a base hydrolysis). (S)-(+)-Dimethyl (3-methyl-2-oxooct-5-yn-1-yl) phosphonate (9bb(i)) was prepared according to the method described in the *Journal of Medicinal Chemistry*, 1986, 29(3), 313-315, except that 2,5-dioxopyrrolidin-1-yl 2-methylhept-4-ynoate (N-hydroxysuccinimide 2-methylhept-4-ynoate) (20bb(i)/20bc(i), Scheme 7f, Step B) was prepared as an activated acyl species (activated ester) instead of 2-methylhept-4-ynoyl chloride to make the chiral auxiliary intermediate diastereomeric pair (S)—N—((R)-2-hydroxy-1-phenylethyl)-2-methylhept-4-ynamide and (R)—N—((R)-2-hydroxy-1-phenylethyl)-2-methylhept-4-ynamide. The diastereomers were separated by silica gel chromatography and (S)—N—((R)-2-hydroxy-1-phenylethyl)-2-methylhept-4-ynamide (21bb(i) was subsequently manipulated as described (Scheme 7f, Step E1 and F1, Scheme 6) to afford the title intermediate as a clear oil. The absolute stereochemistry of the title intermediate was proven by determination of its specific rotation: $[\alpha]^T_\lambda$=α/cl, $[\alpha]^{21.9}_D$=+0.574/(0.025 g/l mL) (0.5)=+45.920 (c=2.5, CHCl$_3$); literature-reported specific rotation for (S)-(+)-diethyl (3-methyl-2-oxooct-5-yn-1-yl)phosphonate from *Liebigs Annalen der Chemie*, 1989, 11, 1081-1083; $[\alpha]^{20}_D$=+37.7° (c=1, CHCl$_3$); chiral analytical HPLC (stationary phase: Chiralcel OJ-H normal phase 250×4.6 mm; mobile phase: 85:15 hexane/l-propanol; flow rate: 1 mL/min) retention time 6.4 min, 100% purity; TLC $R_f$ 0.32 (solvent system: 4:1 v/v ethyl acetate-hexane); $^1$H-NMR (CDCl$_3$) δ 3.76-3.80 (m, 6H), 3.11-3.29 (m, 2H), 2.86-2.95 (m, 1H), 2.36-2.44 (m, 1H), 2.26-2.33 (m, 1H), 2.09-2.16 (m, 2H), 1.16-1.20 (m, 3H), 1.06-1.11 (m, 3H); MS (ESI$^+$) m/z 247 (M+H)$^+$.

A second preparation of the title intermediate by the same process described above afforded the title intermediate wherein the specific rotation (c=1, CHCl$_3$) is +49°.

Alternative preparation of (S)-(+)-dimethyl (3-methyl-2-oxo-6-phenylhexyl)phosphonate (9mb(i))

Scheme 8, Step A: Preparation of (S)-(+)-dimethyl (3-methyl-2-oxo-6-phenylhex-5-yn-1-yl)phosphonate (9db(i))

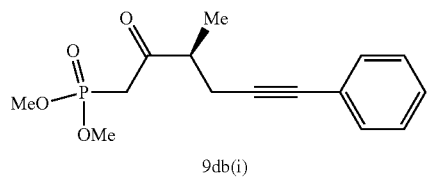 [SMILES: COP(=O)(CC(=O)[C@@H](C)CC#Cc1ccccc1)OC]

9db(i)

(S)-(+)-Dimethyl (3-methyl-2-oxo-6-phenylhex-5-yn-1-yl)phosphonate was prepared in the same manner as that described for the preparation of intermediate 9bb(i) except that intermediate (S)-2-methyl-5-phenylpent-4-ynoic acid (18db(i) was prepared instead of (S)-2-methylhept-4-ynoic acid (18bb(i)) and used as shown in Scheme 5, steps xv, xvi, and xvii followed by Scheme 4, steps xi, xii, and xiii to complete the synthesis of the title compound 9h as a clear oil; TLC $R_f$ 0.22 (solvent system: 4:1 v/v ethyl acetate-hexane); MS (ESI$^+$) m/z 295 (M+H)$^+$.

Scheme 8, Step B: Preparation of (S)-(+)-dimethyl (3-methyl-2-oxo-6-phenylhexyl)phosphonate (9mb (i))

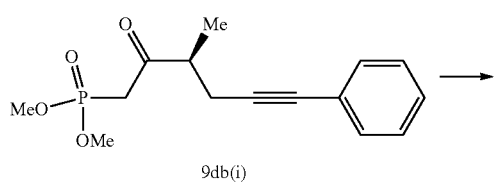

9db(i)

-continued

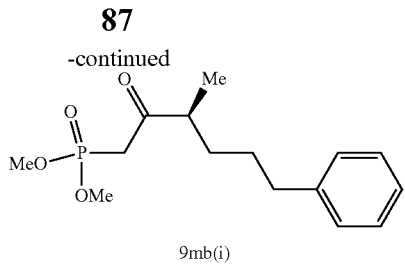

9mb(i)

To a solution consisting of ((S)-dimethyl (3-methyl-2-oxo-6-phenylhex-5-yn-1-yl)phosphonate) (0.98 g, 3.3 mmol) in methanol (25 mL) was added palladium 5% on activated carbon (100 mg) and the reaction atmosphere was replaced with one atmosphere of hydrogen gas. Upon completion of the reaction, after the uptake of hydrogen had ceased, the mixture was filtered through a thin pad of celite and concentrated under vacuum. The residue was purified by silica gel chromatography eluting with ethyl acetate-heptane (70:30 v/v) to give 930 mg (93.9%) of the title compound as a colorless oil; TLC R$_f$=0.24 (solvent system: 70:30 v/v ethyl acetate-heptane; $^1$H-NMR (CDCl$_3$) δ 7.3-7.2 (m, 2H), 7.2-7.1 (m, 3H), 3.8-3.7 (m, 6H), 3.12 (s, 1H), 3.07 (s, 1H), 2.8-2.7 (m, 1H), 2.7-2.5 (m, 2H), 1.8-1.7 (m, 2H), 1.7-1.5 (m, 2H), 1.1 (d, 3H); MS (ESI$^+$) m/z 299 (M+H)$^+$.

Detailed procedures for preparing the protected alcohol intermediates (5) are described below. The following examples are not intended to limit the scope of the present invention.

Preparation of O-protected (R)-3,3-difluoro-5-(hydroxymethyl)pyrrolidin-2-one (5)

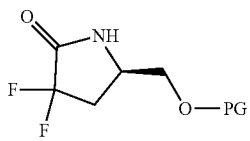

5

Scheme 9, Step xviii: Preparation of (R)-3,3-dimethyltetrahydropyrrolo[1,2-c]oxazol-5(3H)-one (1)

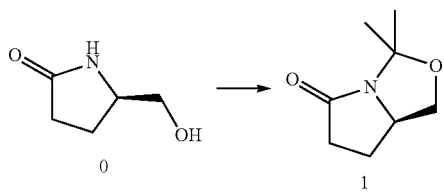

To a solution consisting of (R)-5-hydroxymethyl-2-pyrrolidinone (DL Chiral, 5.3 g, 46 mmol) in 2,2-dimethoxypropane (DMP) (40 mL) was added camphorsulfonic acid (530 mg). The mixture was brought to reflux at 75° C. for 4 hours, and was subsequently concentrated in vacuo. Fresh DMP (40 mL) was then added and the mixture was brought to reflux overnight. After concentration, the remaining residue was purified by silica gel chromatography. Elution with ethyl acetate:heptanes (1:2 v/v) afforded the title intermediate (3.6 g) as a clear oil; TLC R$_f$0.20 (solvent system 50:50 v/v heptanes:ethyl acetate); $^1$H-NMR (CDCl$_3$) δ 4.3-4.2 (1H, m), 4.1 (1H, dd), 3.5 (1H, t), 2.9-2.7 (1H, m), 2.6-2.5 (1H, m), 2.2-2.1 (1H, m), 1.9-1.7 (1H, m), 1.7 (3H, s), 1.5 (3H, s); MS (ESI$^+$) m/z 156.2 (M+H)$^+$.

Scheme 9, Step xviii: Alternate preparation of (R)-3,3-dimethyltetrahydropyrrolo[1,2-c]oxazol-5(3H)-one (1)

To a solution of R-5-hydroxymethyl-2-pyrrolidinone (20 g, 174 mmol) in 2,2-dimethoxypropane (1.4 L, 1139 mmol) was added camphorsulfonic acid (1.0 g, 4.3 mmol). The mixture was refluxed at 75° C. for 20 hours. The reaction was treated with a saturated aqueous solution of sodium bicarbonate, diluted with water, and extracted with ethyl acetate. The combined organic phase was washed with a saturated aqueous solution of sodium chloride, dried over sodium sulfate, filtered and concentrated. The residue was purified by silica gel chromatography eluting with methanol:dichloromethane (1:70 v:v) to afford 21.2 g (78%) of the title compound as a white solid; TLC R$_f$0.6 (solvent system: 25:75 v/v ethyl acetate-hexane); MS (ESI$^+$) m/z 156.1 (M+H)$^+$, 178.1 (M+Na)$^+$; $^1$H-NMR (CDCl$_3$) δ 4.3-4.2 (m, 1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Scheme 9, Step xviii: Alternate preparation of (R)-3,3-dimethyltetrahydropyrrolo[1,2-c]oxazol-5(3H)-one (1)

To a solution of R-5-hydroxymethyl-2-pyrrolidinone (50.0 g, 434 mmol) in 2,2-dimethoxypropane (533 mL, 4.3 mol) was added camphorsulfonic acid (2.85 g, 10.8 mmol). The mixture was refluxed at 88° C. for 1.5 hours, distilling off the methanol. The reaction was heated to 95° C. for 1 hour, cooled to room temperature, treated with 5 mL of triethylamine, and stirred for 5 minutes. The mixture was then diluted with 500 mL (hexanes:ethyl acetate 1:3), washed sequentially with a 50% aqueous solution of sodium chloride and a saturated aqueous solution of sodium chloride. The organic phase was dried over sodium sulfate, filtered and concentrated. The residue was purified by crystalization from hexanes to afford 30.48 g (45%) of the title compound as white crystalline solid. TLC R$_f$0.4 (solvent system: 5:95 v/v methanol:dichloromethane) MS (ESI$^+$) m/z 156.1 (M+H)$^+$, 178.1 (M+Na)$^+$; $^1$H-NMR (CDCl$_3$) δ 4.3-4.2 (m, 1H), 4.1 (dd, 1H), 3.5 (t, 1H), 2.9-2.7 (m, 1H), 2.6-2.5 (m, 1H), 2.2-2.1 (m, 1H), 1.9-1.7 (m, 1H), 1.7 (s, 3H), 1.5 (s, 3H).

Preparation of (7aR)-6-fluoro-3,3-dimethyltetrahydropyrrolo[1,2-c]oxazol-5(3H)-one (1.1)

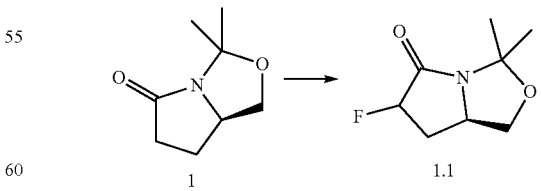

To a −75° C. solution consisting of (R)-3,3-dimethyltetrahydropyrrolo[1,2-c]oxazol-5(3H)-one (intermediate 1, 18.5 g, 119.2 mmol) in dry THF (400 mL) was added lithium diisopropylamide (74.5 mL, 149 mmol, 2M in heptanes/THF/ethylbenzene from Sigma Aldrich) dropwise over 20 minutes, then stirred for 1 hour. The reaction was then treated with N-fluorobenzenesulfonimide (56.6 g, 166.9 mmol, NFSi, from Oakwood Chemical) in 300 ml of THF over 30 minutes, then stirred for 16 hours, warming to room temperature. To the reaction was added a saturated aqueous solution of ammonium chloride. The organic material was extracted twice with ethyl acetate. The organic layer was washed with a 50% aqueous solution of sodium chloride, followed by a saturated solution of sodium chloride, and dried over sodium sulfate, filtered and concentrated. The residue was redissolved in 200 mL of ethyl acetate and treated with 200 mL of heptanes causing a white precipitate. The precipitate was filtered and washed with 50% ethyl acetate in heptanes. The combined filtrate was concentrated. The residue was again redissolved in 200 mL of ethyl acetate and treated with 200 mL of heptanes. The precipitate again was filtered and washed with 50% ethyl acetate in heptanes. The filtrate was concentrated and the residue (31 g) was purified by silica gel chromatography eluting with ethyl acetate:hexanes (1:3 v:v) to afford pure samples of each of the diasteriomers of the title compounds (4.1 g of each as tan solids) and 3.8 g of the mixed (approx. 1:1 ratio) diastereomers. The total yield was 12.0 g (65%).

(6S,7aR)-6-fluoro-3,3-dimethyltetrahydropyrrolo[1,2-c]oxazol-5(3H)-one (1.1α) and (6R,7aR)-6-fluoro-3,3-dimethyltetrahydropyrrolo[1,2-c]oxazol-5(3H)-one (1.1β)

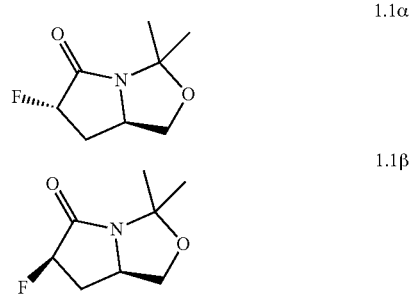

Separation of the two isomers by chromatography gives the two pure epimers.

(1.1α) TLC R$_f$0.55 (solvent system: 60:40 v/v ethyl acetate:hexanes); HPLC on an Agilent 1100 instrument, ultraviolet detector at 210 nm, stationary phase Gemini 3m C18, 50×2 mm column, mobile phase, water:methanol:acetic acid gradient over 4 min (90:10:0.1 to 10:90:0.1), retention time 2.33 minutes; MS (ESI$^+$) m/z 174.1 (M+H)$^+$; 1H-NMR (CDCl$_3$) δ 5.085 (ddd, J=51.6, 6.0, 0.8 Hz, 1H) 4.5-4.4 (m, 1H), 4.15 (dd, 1H), 3.4 (dd, 1H), 2.5-2.3 (m, 1H), 2.1-1.7 (m, 1H), 1.65 (s, 3H), 1.5 (s, 3H); $^{19}$F-NMR (CDCl$_3$, 376 MHz) δ −184.5 (ddd, J=52, 41, 22 Hz, 1F).

(1.1β) TLC R$_f$0.45 (solvent system: 60:40 v/v ethyl acetate:hexanes); HPLC on an Agilent 1100 instrument, ultraviolet detector at 210 nm, stationary phase Gemini 3m C18, 50×2 mm column, mobile phase, water:methanol:acetic acid gradient over 4 min (90:10:0.1 to 10:90:0.1), retention time 1.69 minutes; MS (ESI$^+$) m/z 174.1 (M+H)$^+$; 1H-NMR (CDCl$_3$) δ 5.325 (ddd, J=52.4, 9.9, 7.7 Hz, 1H) 4.2 (dd, 1H), 4.0-3.9 (m, 1H), 3.5 (dd, 1H), 2.8-2.7 (m, 1H), 2.0-1.9 (m, 1H), 1.7 (s, 3H), 1.5 (s, 3H); $^{19}$F-NMR (CDCl$_3$, 376 MHz) δ −185.9 (dd, J=52, 23 Hz, 1F).

Preparation of (R)-6,6-difluoro-3,3-dimethyltetrahydropyrrolo[1,2-c]oxazol-5(3H)-one (2)

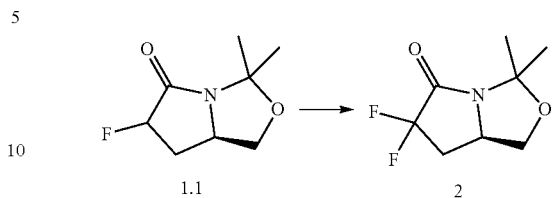

To a −75° C. solution consisting of (7aR)-6-fluoro-3,3-dimethyltetrahydropyrrolo[1,2-c]oxazol-5(3H)-one (8.0 g, 46.2 mmol, mixture of diastereomers of 1.1) in dry THF (300 mL) was added lithium his(trimethylsilyl)amide (50.8 mL, 50.8 mmol, LiHMDS 1M in THF) dropwise over 10 minutes, then stirred for 1 hour. The reaction was then treated with a solution of N-fluorobenzenesulfonimide (17.5 g, 55.4 mmol) in THF (100 mL) over 10 minutes, then stirred for 30 minutes. Lithium bis(trimethylsilyl)amide (10.0 mL, 10 mmol) was added, and the reaction stirred for 16 hours, warming to room temperature. To the reaction mixture was added a 50% aqueous solution of ammonium chloride. The organic material was extracted with ethyl acetate:heptanes (5:1). The organic layer was washed sequentially with a 50% aqueous solution of sodium chloride, water, and a saturated solution of sodium chloride, then dried over sodium sulfate, filtered and concentrated. The residue was purified by silica gel chromatography eluting with ethyl acetate:hexanes (1:5 v:v) to afford 7.39 g (79%) of the title compounds as a tan solid; TLC R$_f$0.70 (solvent system: 50:50 v/v ethyl acetate:hexanes); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 9, Step xix: Alternative preparation of (R)-6,6-difluoro-3,3-dimethyltetrahydropyrrolo[1,2-c]oxazol-5 (3H)-one (2)

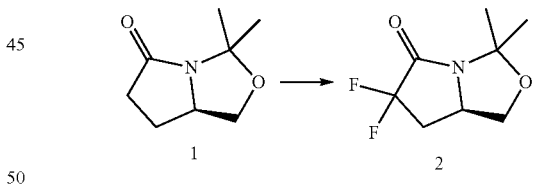

To a −78° C. solution consisting of (R)-3,3-dimethyltetrahydropyrrolo[1,2-c]oxazol-5(3H)-one (1) (15.5 g, 100.0 mmol) in dry THF (300 mL) was added sec-butyl lithium (78.5 mL, 110 mmol, 1.4M in cyclohexane, from Sigma Aldrich) dropwise over 5 minutes, then stirred for 1 hour. The reaction was then treated with N-fluorobenzene sulfonimide (35 g, 111 mmol, NFSi, from Oakwood) in THF (100 mL) over 5 minutes, then stirred for 1 hour. To the reaction mixture was then added lithium bis(trimethylsilyl)amide (110 mL, 110 mmol, 1.0M in THF, from Sigma Aldrich) dropwise over 5 minutes, then stirred for 1 hour. The reaction was then treated with NFSi (34.4 g, 109 mmol) in THF (100 mL) over 5 minutes, then stirred for 2 hours. To the reaction, at −78° C., was added lithium bis(trimethylsilyl)amide (40 mL, 40 mmol, 1M in THF) and stirred for 30 minutes. The cooling bath was removed and a saturated aqueous solution of ammonium chloride added. The reaction mixture was allowed to warm to room temperature, and the organic material was extracted with ethyl acetate. The organic layer was sequentially washed with water, a 50% saturated aqueous solution of sodium chloride, and a saturated solution of sodium chloride, dried over sodium sulfate, filtered and concentrated. The residue was purified by silica gel chromatography eluting with ethyl acetate:hexanes (1:3 v:v) to afford 11.64 g (61%) of the title compound as a solid; TLC $R_f$ 0.4 (solvent system: 5:95 v/v methanol:dichloromethane); $^1$H-NMR (CDCl$_3$) δ 4.3 (dd, 1H), 4.2-4.0 (m, 1H), 3.5 (t, 1H), 2.9-2.7 (m, 1H), 2.2-2.0 (m, 1H), 1.7 (s, 3H), 1.5 (s, 3H).

Scheme 9, Step xx: Preparation of (R)-3,3-difluoro-5-(hydroxymethyl)pyrrolidin-2-one ((R)-4)

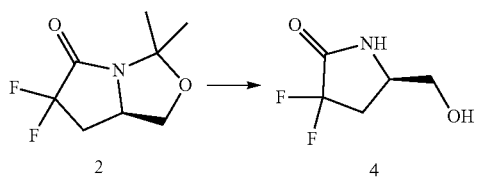

To a solution consisting of (R)-6,6-difluoro-3,3-dimethyltetrahydropyrrolo[1,2-c]oxazol-5(3H)-one (12.5 g, 65.4 mmol) in water:1,4-dioxane (300 mL, 1:1) was added Amberlite IR-120H* (6.23 g), and the reaction heated to 115° C. for 6 hours. The reaction mixture was filtered through celite and washed with methanol before concentrating with toluene and ethanol. The residue was washed with diethyl ether to give 8.8 g (89%) of the title compound as a tan solid and used without further purification; TLC $R_f$ 0.25 (solvent system: 70:30 v/v ethyl acetate:hexanes)

*Amberlite IR-120H ion-exchange resin, strongly acid gel-type resin with sulfonic acid functionality, CAS: 39389-20-3. 75 g of Amberlite was washed and decanted three times with deionized water. The fourth wash was filtered using suction filtration and the semi-dry resin was quickly washed with 2-propanol then diethyl ether. The resin was dried to give 54 g of free flowing dark brown bead resin.

Scheme 9, Step xxi: Preparation of (5R)-5-((1-ethoxyethoxy)methyl)-3,3-difluoropyrrolidin-2-one (5; PG=EE)

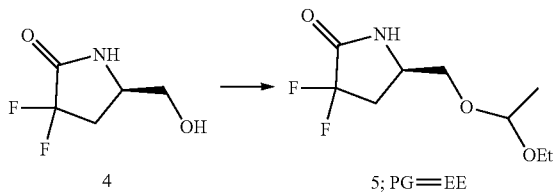

To a solution consisting of (R)-3,3-difluoro-5-(hydroxymethyl)pyrrolidin-2-one (intermediate 4, 540 mg, 3.57 mmol) in dichloromethane (20 mL) and THF (10 mL) was added ethyl vinyl ether (1.4 mL, 15 mmol) followed by trifluoroacetic acid (20 mg). The reaction mixture was stirred at room temperature for 16 hours. To the reaction was then added THF (10 ml) to dissolve precipitate, followed by ethyl vinyl ether (0.4 mL, 4.2 mmol) and the reaction stirred for 3 hours. The reaction mixture was diluted with ethyl acetate (150 mL) and washed with a saturated aqueous solution of sodium bicarbonate (10 mL) and brine (5 mL) before being dried over sodium sulfate, filtered, and concentrated. The residue was purified by silica gel chromatography. Elution with methanol:dichloromethane (1:80 v/v) afforded 726 mg (91%) of the title intermediate as a clear oil; TLC $R_f$ 0.60 (solvent system: 93:7 v/v dichloromethane:methanol); $^1$H-NMR (CDCl$_3$) δ 4.8-4.6 (m, 1H), 4.0-3.8 (m, 1H), 3.7-3.5 (m, 2H), 3.5-3.4 (m, 2H), 2.8-2.6 (m, 1H), 2.4-2.2 (m, 1H), 1.3 (d, 3H), 1.2 (t, 3H); MS (ESI$^+$) m/z 241.1 (M+NH$_4$)$^+$, 246.1 (M+Na)$^+$; (ESI$^-$) m/z 222.1 (M-H)$^-$.

Scheme 9, Step xxi: Preparation of (R)-5-(((tert-butyldimethylsilyl)oxy)methyl)-3,3-difluoropyrrolidin-2-one (5; PG=TBS)

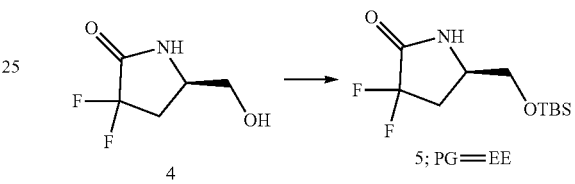

To a solution consisting of (R)-3,3-difluoro-5-(hydroxymethyl)pyrrolidin-2-one (intermediate 4, 880 mg, 3.57 mmol) in DMF (10 mL) and THF (10 mL) was added tert-butyldimethylchlorosilane (1.40 g, 9.23 mmol) followed by imidazole (800 mg, 6.55 mmol). The reaction mixture was stirred at room temperature for 16 hours. The reaction mixture was diluted with water (10 mL) and extracted thrice with ethyl acetate (55 ml, 2×25 ml). The combined organics were washed with 1:1 water:brine (3×10 mL) and brine (5 mL) before being dried over sodium sulfate, filtered, and concentrated. The residue was purified by silica gel chromatography. Elution with methanol:dichloromethane (1:50 v/v) afforded the title intermediate (1528 mg) as a clear oil; TLC $R_f$ 0.60 (solvent system: 95:5 v/v dichloromethane:methanol); $^1$H-NMR (CDCl$_3$) δ 3.8-3.7 (m, 1H), 3.7-3.6 (m, 1H), 3.5-3.4 (m, 1H), 2.6-2.5 (m, 1H), 2.3-2.1 (m, 1H), 0.8 (s, 9H), 0.0 (s, 6H); MS (ESI$^+$) m/z 266.1 (M+H)$^+$.

Scheme 10, Step xxii: Preparation of methyl 7-((5R)-5-((1-ethoxyethoxy)methyl)-3,3-difluoro-2-oxopyrrolidin-1-yl)heptanoate (6A; PG=EE)

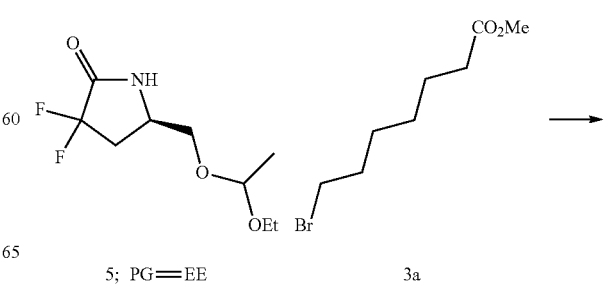

93

-continued

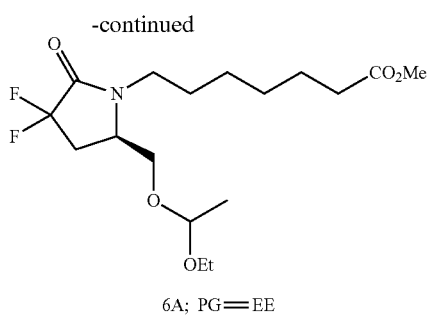

6A; PG=EE

To a suspension consisting of sodium hydride (60% in mineral oil, 18 mg, 0.45 mmol) and sodium iodide (74 mg, 0.49 mmol) in DMF (5 mL) was added dropwise a solution of (5R)-5-((1-ethoxyethoxy)methyl)-3,3-difluoropyrrolidin-2-one (intermediate 5; PG=EE, 100 mg, 0.45 mmol) in DMF (5 mL). The mixture was stirred at room temperature for two hours followed by 50° C. for 30 minutes. To the reaction mixture was added dropwise methyl 7-bromoheptanoate (compound 3a, available from Alfa Aesar, 120 mg, 0.538 mmol) and stirring continued overnight at 50° C. The mixture was diluted with ethyl acetate (200 mL) and washed sequentially with 0.5N hydrochloric acid (20 mL), a 5% aqueous solution of sodium thiosulfate (10 mL), 50% brine (4×25 mL), and brine (25 mL). The organic phase was dried over sodium sulfate, filtered, and concentrated. The residue was purified by silica gel chromatography. Elution with methanol:dichloromethane (1:100 v/v) afforded 128 mg (78%) of the title intermediate as a clear oil; TLC $R_f$ 0.95 (solvent system: 93:7 v/v dichloromethane:methanol); $^1$H-NMR (CDCl$_3$) δ 4.7 (dq, 1H), 3.85-3.75 (m, 1H), 3.75-3.4 (m, 8H), 3.15-3.05 (m, 1H), 2.65-2.35 (m, 1H), 2.3 (t, 2H), 1.7-1.4 (m, 4H), 1.4-1.3 (m, 4H), 1.3 (d, 3H), 1.2 (t, 3H); MS (ESI$^+$) m/z 383.2 (M+NH$_4$)$^+$, 388.1 (M+Na)$^+$.

To a suspension consisting of sodium hydride (60% in mineral oil, 108 mg, 2.7 mmol) and sodium iodide (450 mg, 3.0 mmol) in DMF (30 mL) was added dropwise a solution of (5R)-5-((1-ethoxyethoxy)methyl)-3,3-difluoropyrrolidin-2-one (intermediate 5; PG=EE, 600 mg, 2.68 mmol) in DMF (30 mL). The mixture was stirred at room temperature for two hours followed by 50° C. for 30 minutes. To the reaction mixture was added dropwise methyl 7-bromoheptanoate (compound 3a, available from Alfa Aesar, 720 mg, 2.23 mmol) and stirring continued overnight at 50° C. The mixture was diluted with ethyl acetate and washed sequentially with 0.5N hydrochloric acid, a 5% aqueous solution of sodium thiosulfate, 50% saturate aqueous solution of sodium chloride, and saturate aqueous solution of sodium chloride. The organic phase was dried over sodium sulfate, filtered, and concentrated. The residue was purified by silica gel chromatography. Elution with methanol:dichloromethane (1:125 v/v) afforded 888 mg (90%) of the title intermediate as a tan solid; TLC $R_f$ 0.95 (solvent system: 93:7 v/v dichloromethane:methanol); MS (ESI$^+$) m/z 383.2 (M+NH$_4$)$^+$, 388.1 (M+Na)$^+$.

94

Scheme 10, Step xxiii: Preparation of (R)-methyl 7-(3,3-difluoro-5-(hydroxymethyl)-2-oxopyrrolidin-1-yl)heptanoate (7A)

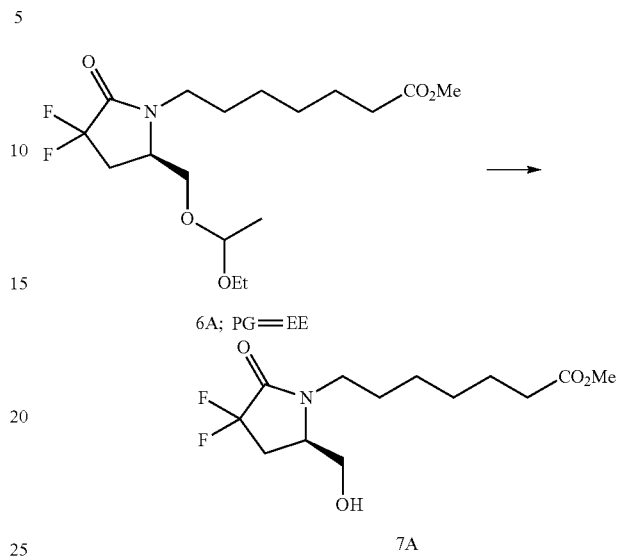

To a solution consisting of methyl 7-((5R)-5-((1-ethoxyethoxy)methyl)-3,3-difluoro-2-oxopyrrolidin-1-yl)heptanoate (intermediate 6A; PG=EE, 113 mg, 0.310 mmol) in methanol (10 mL) was added p-toluenesulfonic acid monohydrate (2 mg) and the mixture was stirred at room temperature for 18 hours. The reaction mixture was concentrated to give a crude residue that was purified by silica gel chromatography. Elution with methanol-dichloromethane (1:80 v/v) afforded 86 mg (97%) of the title intermediate as a pale yellow oil; TLC $R_f$ 0.55 (solvent system: 7:93 v/v methanol:dichloromethane); $^1$H-NMR (CDCl$_3$) δ 3.85-3.6 (m, 4H), 3.65 (s, 3H), 3.2-3.1 (m, 1H), 2.6-2.4 (m, 2H), 2.3 (t, 2H), 1.7-1.4 (m, 4H), 1.4-1.2 (m, 4H); MS (ESI$^+$) m/z 311.2 (M+NH$_4$)$^+$, 316.1 (M+Na)$^+$.

Scheme 10, Step xxiv: Preparation of (R)-methyl 7-(3,3-difluoro-5-formyl-2-oxopyrrolidin-1-yl) heptanoate (8A)

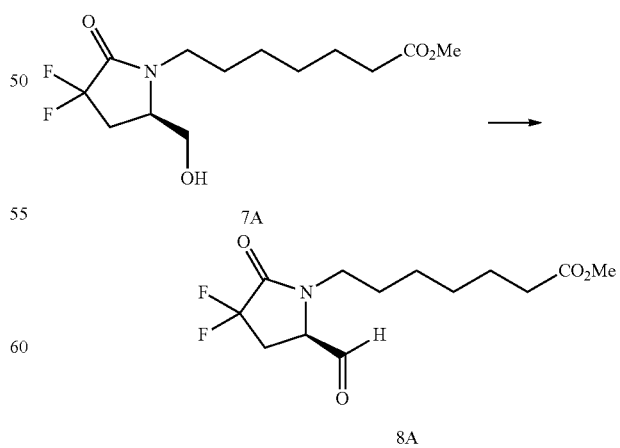

To a solution consisting of (R)-methyl 7-(3,3-difluoro-5-(hydroxymethyl)-2-oxopyrrolidin-1-yl)heptanoate (intermediate 7A, 85 mg, 0.29 mmol) in dichloromethane (10 mL) was added Dess-Martin periodinate (150 mg, 0.348 mmol), and the reaction mixture was stirred for four hours. The reaction mixture was filtered and the filtrate was subsequently concentrated. Without further workup, the residue was purified by silica gel chromatography. Elution with methanol-dichloromethane (1:200 v/v) afforded 77 mg (91%) of the title intermediate as a pale yellow oil; TLC $R_f$ 0.60 (solvent system: 7:93 v/v methanol: dichloromethane).

Scheme 10, Step xxii: Preparation of (R)-methyl 5-(3-(5-(((tert-butyldimethylsilyl)oxy)methyl)-3,3-difluoro-2-oxopyrrolidin-1-yl)propyl)thiophene-2-carboxylate (6C; PG=TBS)

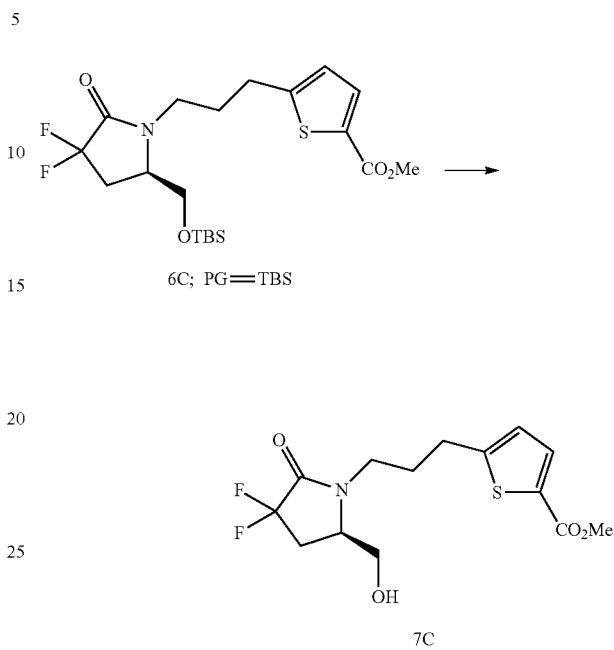

To a suspension consisting of sodium hydride (60% in mineral oil, 458 mg, 11.45 mmol) and sodium iodide (1.79 g, 12.0 mmol) in DMF (60 mL) was added dropwise a solution consisting of (R)-5-(((tert-butyldimethylsilyl)oxy)methyl)-3,3-difluoropyrrolidin-2-one (5; PG=TBS, 2.9 g 10.9 mmol) in DMF (10 mL). The mixture was stirred at room temperature for 90 minutes. To the reaction mixture was added dropwise methyl 5-(3-bromopropyl)thiophene-2-carboxylate (24, 3.16 g, 12.0 mmol, preparation described above) and stirring was continued at 50° C. for 16 hours. The mixture was treated with an aqueous solution of ammonium chloride and extracted with 2:1 ethyl acetate:heptanes. The combined organics were washed with a 50% saturated aqueous solution of sodium chloride, followed by a saturated aqueous solution of sodium chloride and was dried over sodium sulfate. The residue was purified by silica gel chromatography. Elution with ethyl acetate:heptanes (1:5 v/v) afforded 4.6 g (93%) of the title intermediate; TLC $R_f$ 0.30 (solvent system: 75:25 v/v heptanes:ethyl acetate); $^1$H-NMR (CDCl$_3$) δ 7.6 (d, 1H), 6.8 (d, 1H), 3.8 (s, 3H), 3.7-3.6 (m, 1H), 3.6-3.5 (m, 1H), 3.3-3.1 (m, 1H), 2.8 (t, 2H), 2.6-2.4 (m, 1H), 2.4-2.2 (m, 1H), 2.0 (s, 3H), 1.2 (t, 1H), 0.8 (s, 9H), 0.0 (s, 6H); MS (ESI$^+$) m/z 465.1 (M+NH$_4$)$^+$.

Scheme 10, Step xxiii: Preparation of (R)-methyl 5-(3-(3,3-difluoro-5-(hydroxymethyl)-2-oxopyrrolidin-1-yl)propyl)thiophene-2-carboxylate (7C)

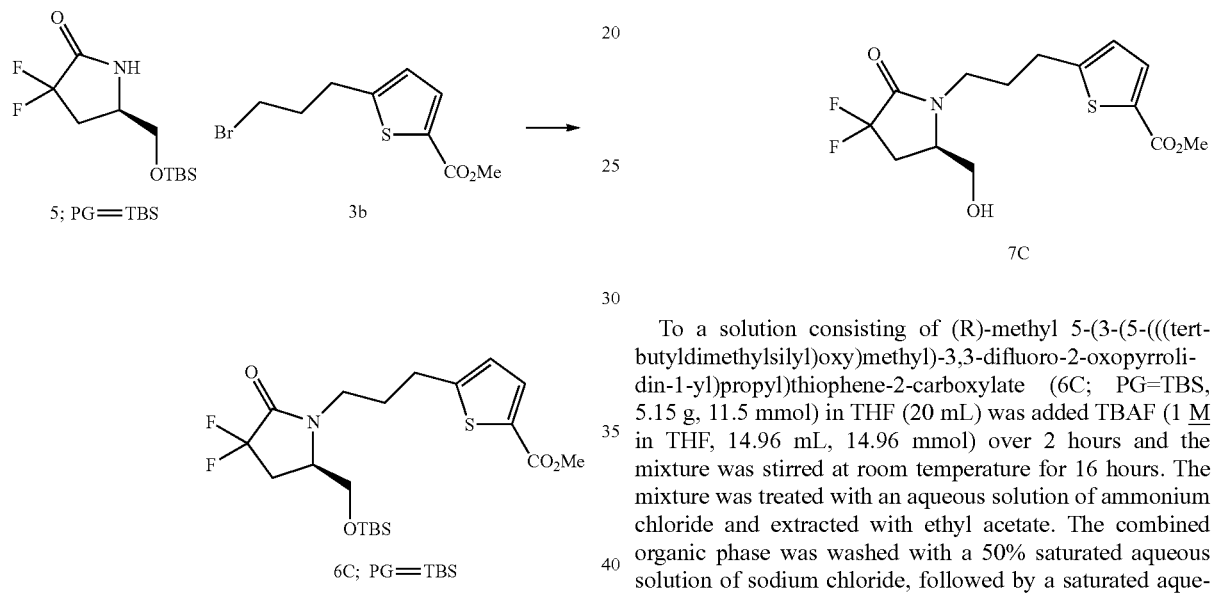

To a solution consisting of (R)-methyl 5-(3-(5-(((tert-butyldimethylsilyl)oxy)methyl)-3,3-difluoro-2-oxopyrrolidin-1-yl)propyl)thiophene-2-carboxylate (6C; PG=TBS, 5.15 g, 11.5 mmol) in THF (20 mL) was added TBAF (1 M in THF, 14.96 mL, 14.96 mmol) over 2 hours and the mixture was stirred at room temperature for 16 hours. The mixture was treated with an aqueous solution of ammonium chloride and extracted with ethyl acetate. The combined organic phase was washed with a 50% saturated aqueous solution of sodium chloride, followed by a saturated aqueous solution of sodium chloride and was dried over sodium sulfate, filtered and concentrate. The residue was purified by silica gel chromatography. Elution with methanol-dichloromethane (1:80 v/v) afforded 3.4 g (88%) of the title intermediate as a pale yellow oil; TLC $R_f$ 0.5 (solvent system: 5:95 v/v methanol:dichloromethane); $^1$H-NMR (CDCl$_3$) δ 7.6 (d, 1H), 6.8 (d, 1H), 3.85 (s, 3H), 3.8-3.6 (m, 4H), 3.3-3.1 (m, 1H), 2.85 (t, 2H), 2.6-2.4 (m, 2H), 2.1-1.9 (m, 2H); MS (ESI$^+$) m/z 351.0 (M+NH$_4$)$^+$.

Scheme 10, Step xxiv: Preparation of (R)-methyl 5-(3-(3,3-difluoro-5-formyl-2-oxopyrrolidin-1-yl)propyl)thiophene-2-carboxylate (8C)

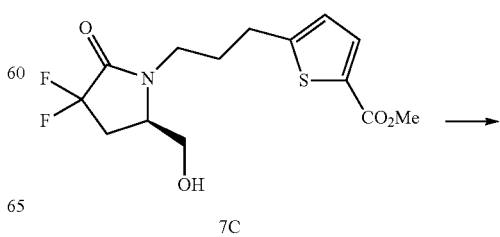

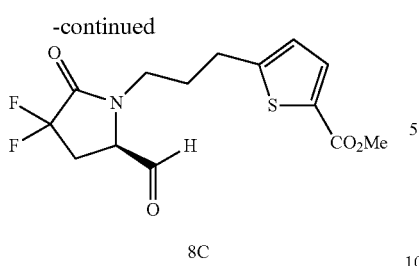

8C (R)-Methyl 5-(3-(3,3-difluoro-5-formyl-2-oxopyrrolidin-1-yl)propyl)thiophene-2-carboxylate was prepared from 7C using the oxidation procedure described for the preparation of intermediate 8A from intermediate 7A to afford the title intermediate (80 mg) as a pale yellow oil; TLC $R_f$ 0.60 (solvent system: 7:93 v/v methanol:dichloromethane).

Details for the methods of preparation of embodiments of the Figure IA are described below. The following examples are not intended to limit the scope of the present invention.

Figure IA

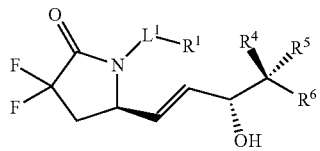

Scheme 11, Step xxv: Preparation of methyl 7-((R)-3,3-difluoro-5-((S,E)-4-methyl-3-oxonon-1-en-6-yn-1-yl)-2-oxopyrrolidin-1-yl)heptanoate (10A)

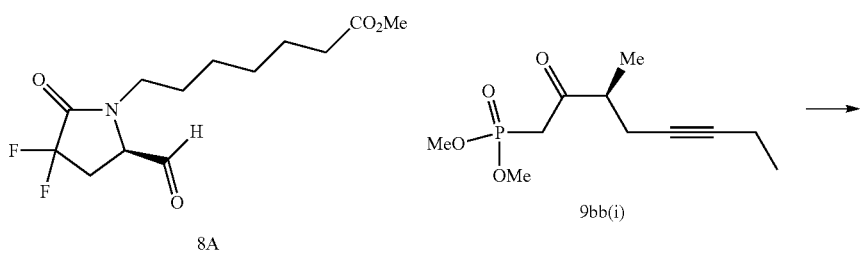

8A

9bb(i)

10A

To an ice cooled mixture consisting of dimethyl (S)-(3-methyl-2-oxooct-5-yn-1-yl)phosphonate (71.2 mmg, 0.29 mmol), (R)-methyl 7-(3,3-difluoro-5-formyl-2-oxopyrrolidin-1-yl) heptanoate (76.6 mg, 0.26 mmol) and lithium chloride (33.4 mg, 0.79 mmol) in THF (3 mL) was added triethylamine (39.9 mg, 0.39 mmol), and the reaction was stirred for 16 hours, warming to room temperature. To the reaction mixture was added an equal amount of a saturated aqueous solution of ammonium chloride and water, and the organic material was extracted three times with ethyl acetate. The combined organic phase was dried over sodium sulfate, filtered and concentrated. The residue was purified by silica gel chromatography eluting with methanol:dichloromethane (1:300 v:v) to afford 81 mg (75%) of the title compound as a clear oil; TLC $R_f$ 0.80 (solvent system: 7:93 v/v methanol:dichloromethane); MS (ESI+) m/z 412.1 (M+H)$^+$, (ESI−) 410.1 (M−H)$^-$; $^1$H-NMR (CDCl$_3$) δ 6.6-6.5 (m, 1H), 6.4 (d, 1H), 4.3-4.2 (m, 1H), 3.65 (s, 3H), 3.7-3.6 (m, 1H) 3.0-2.7 (m, 3H), 2.5-2.4 (m, 1H) 2.4-2.2 (m, 4H) 2.2-2.1 (m, 2H), 1.7-1.4 (m, 4h), 1.4-1.2 (m, 4H), 1.2 (d, 3H), 1.1 (t, 3H).

Scheme 11, Step xxvi: Primary preparation of methyl 7-((R)-3,3-difluoro-5-((3 S,4S,E)-3-hydroxy-4-methylnon-1-en-6-yn-1-yl)-2-oxopyrrolidin-1-yl)heptanoate (11A-1) and methyl 7-((R)-3,3-difluoro-5-((3R,4S,E)-3-hydroxy-4-methylnon-1-en-6-yn-1-yl)-2-oxopyrrolidin-1-yl)heptanoate (11A-2)

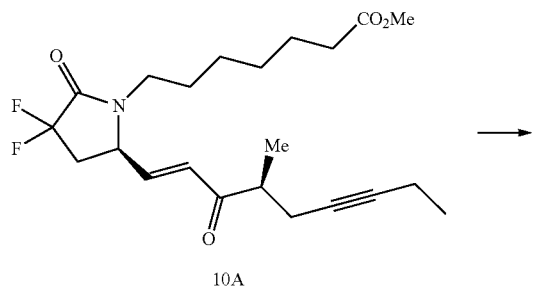

10A

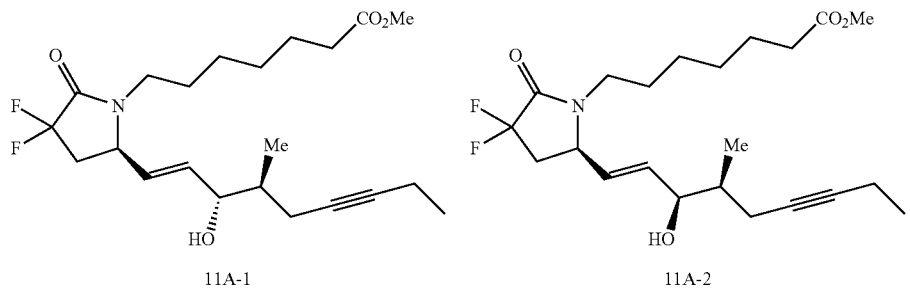

11A-1                                11A-2

To a −40° C. solution consisting of methyl 7-((R)-3,3-difluoro-5-((S,E)-4-methyl-3-oxonon-1-en-6-yn-1-yl)-2-oxopyrrolidin-1-yl)heptanoate (61 mg, 0.148 mmol) in methanol (5 mL) was added cerium chloride heptahydrate in one portion. The reaction was stirred for 15 minutes, then cooled to −78° C. for 20 minutes. Sodium borohydride (12 mg, 0.324 mmol) was added and the reaction stirred for 3 hours. To the reaction mixture was added equal parts water and a saturated aqueous solution of ammonium chloride, and the mixture was warmed to room temperature. The mixture was diluted with a saturated aqueous solution of sodium chloride, and the organic material was extracted three times with ethyl acetate. The combined organic phase was dried over sodium sulfate, filtered and concentrated to a cloudy white oil. The epimeric mixture of the title compounds was isolated by silica gel chromatography eluting with methanol:dichloromethane (1:300 v:v).

From the stereoisomeric mixture comprising of 11A-1 and 11A-2 was isolated the stereospecific isomers by prep HPLC on an Agilent Semi-Prep instrument; ultraviolet detector at 210 nm; Luna Silica 250×10 mm column; mobile phase of heptane-ethanol (98:2 v/v), 5 mL/min.

11A-1: (8.1 mg, 13%); a clear oil; HPLC retention time 57 min; TLC $R_f$ 0.60 (solvent system: 7:93 v/v methanol:dichloromethane); HPLC: retention time 19.076 min, Agilent 1100, Luna Silica 4.6×250 mm, 5μ, ultraviolet detector at 210 nm, in 95:5 heptane:ethanol; MS (ESI$^+$) m/z 414.1 (M+H)$^+$ (ESI$^-$) m/z 412.1 (M−H)$^-$.

11A-2: (20.5 mg); a clear oil; HPLC retention time 42 min; MS (ESI$^+$) m/z 414.1 (M+H)$^+$ (ESI$^-$) m/z 412.1(M−H)$^-$.

Scheme 11, Step xxvi: Alternative preparation of methyl 7-((R)-3,3-difluoro-5-((3 S,4S,E)-3-hydroxy-4-methylnon-1-en-6-yn-1-yl)-2-oxopyrrolidin-1-yl)heptanoate (11A-1) and methyl 7-((R)-3,3-difluoro-5-((3S,4R,E)-3-hydroxy-4-methylnon-1-en-6-yn-1-yl)-2-oxopyrrolidin-1-yl)heptanoate (11A-2)

To a solution consisting of methyl 7-((R)-3,3-difluoro-5-((S,E)-4-methyl-3-oxonon-1-en-6-yn-1-yl)-2-oxopyrrolidin-1-yl)heptanoate (169 mg, 0.460 mmol) and (R)-Corey-Bakshi-Shibata catalyst (1 M in THF, 0.46 mmol) in dichloromethane (100 mL) at −40° C. was added catechol borane (1 M in THF, 0.46 mmol) dropwise over 10 minutes. The reaction mixture was stirred overnight, warming to room temperature, then quenched with 1 N HCl (10 mL). The reaction mixture was extracted with ethyl acetate. The combined organic phase was dried over sodium sulfate and concentrated to a cloudy brown oil. The residue was purified by silica gel chromatography. Elution with methanol:dichloromethane (1:200 v:v) afforded a mixture of 11A-1 and 1A-2 (52 mg) as a clear oil; $R_f$ 0.65 (solvent system: 7:93 v/v methanol: dichloromethane).

The epimers were separated and purified. Epimer 11A-1 (15.2 mg) was isolated using the prep HPLC method described of the original preparation of this compound above.

Scheme 11, Step xxvii: Preparation of 7-((R)-3,3-difluoro-5-((3S,4S,E)-3-hydroxy-4-methylnon-1-en-6-yn-1-yl)-2-oxopyrrolidin-1-yl)heptanoic acid (26A-1)

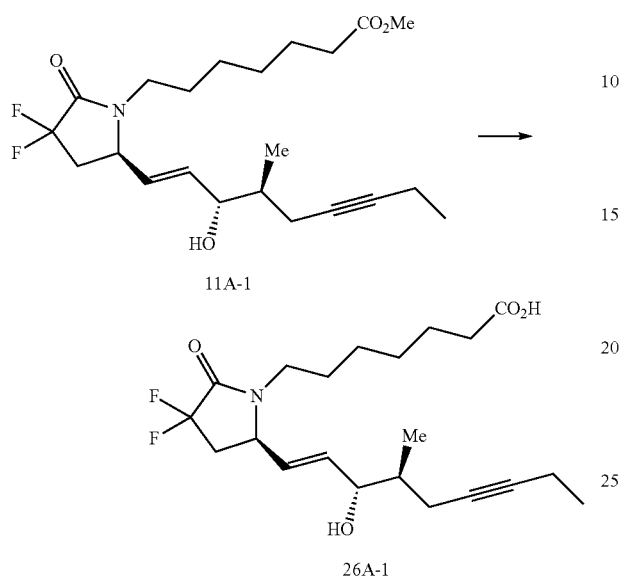

To a solution of methyl 7-((R)-3,3-difluoro-5-((3S,4S,E)-3-hydroxy-4-methylnon-1-en-6-yn-1-yl)-2-oxopyrrolidin-1-yl)heptanoate (14 mg, 0.034 mmol) in methanol (450 μL) was added lithium hydroxide (300 μL, 0.30 mmol), and the reaction was stirred for 4 hours. To the reaction mixture was added a saturated aqueous solution of potassium bisulfate, and the organic material was extracted four times with ethyl acetate. The organic phase was dried over sodium sulfate, filtered and concentrated. The residue was purified by silica gel chromatography eluting with acetic acid:methanol:dichloromethane (1:2:100 v:v) to afford 12.0 mg (89%) of the title compound as a clear oil; TLC $R_f$ 0.45 (solvent system: 1:5:95 v/v acetic acid:methanol:dichloromethane); $^1$H-NMR (CDCl$_3$) δ 5.9-5.8 (m, 1H), 5.6-5.5 (m, 1H), 4.2-4.1 (m, 2H), 3.7-3.5 (m, 1H), 3.1-2.9 (m, 1H), 2.8-2.7 (br s, 1H), 2.4-2.3 (t, 2H), 2.3-2.1 (m, 5H), 1.9-1.8 (m, 1H), 1.7-1.5 (m, 5H), 1.4-1.2 (m, 4H), 1.1 (t, 3H), 1.0 (d, 3H); $^{19}$F-NMR (CDCl$_3$, 376 Hz) δ -103.5 (dt, J=13.2, 267 Hz, 1F), -105.5 (dt, J=15.1, 267, 1F).

Scheme 11, Step xxvii: Preparation of 7-((R)-3,3-difluoro-5-((3R,4S,E)-3-hydroxy-4-methylnon-1-en-6-yn-1-yl)-2-oxopyrrolidin-1-yl)heptanoic acid (26A-2)

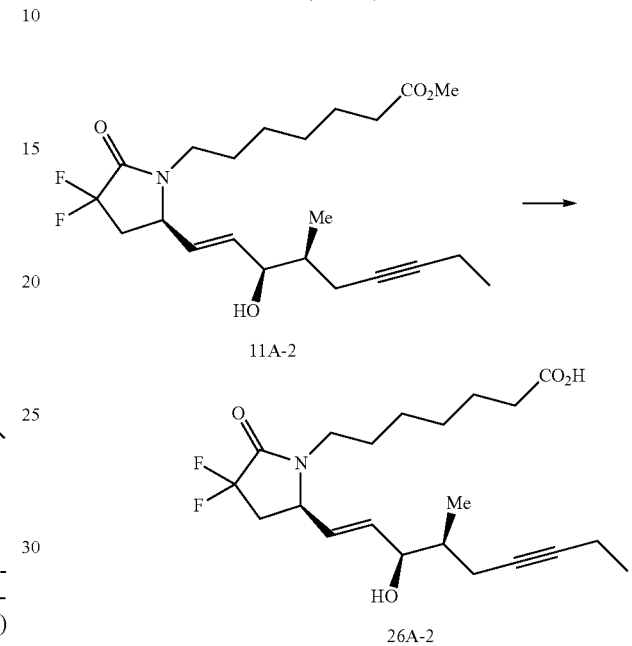

14.8 mg of a clear oil; TLC $R_f$ 0.45 (solvent system: 95:5:1 v/v dichloromethane-methanol-acetic acid); MS (ESI$^+$) m/z 400 (M+H)$^+$, MS (ESI$^-$) m/z 398 (M-H)$^-$.

Scheme 11, Step xxv: Preparation of methyl 7-((R)-3,3-difluoro-5-((S,E)-4-methyl-3-oxo-7-phenylhept-1-en-1-yl)-2-oxopyrrolidin-1-yl)heptanoate (10B)

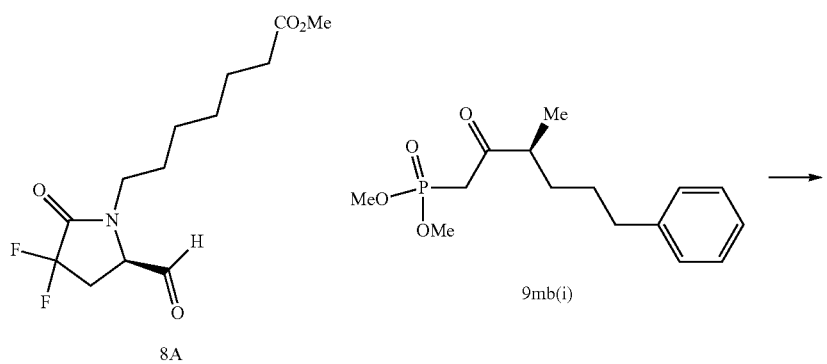

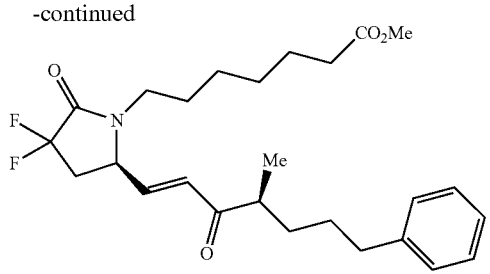

10B

To a 0° C. mixture consisting of dimethyl (S)-(3-methyl-2-oxo-6-phenylhexyl) phosphonate (596.6 mg, 2.0 mmol), (R)-methyl 7-(3,3-difluoro-5-formyl-2-oxopyrrolidin-1-yl)heptanoate (585 mg, 2.0 mmol) and lithium chloride (254 mg, 6.0 mmol) in THF (30 mL) was added triethyl amine (405 mg, 4.0 mmol) dropwise over 5 minutes. The reaction was stirred for one hour at 0° C., then for 2 hours at room temperature. To the reaction mixture was added a saturated aqueous solution of ammonium chloride and the organic material was extracted with ethyl acetate. The organic phase was dried over sodium sulfate, filtered and concentrated. The residue was purified by silica gel chromatography eluting with methanol:dichloromethane (1:200 v:v) to afford 608 mg (65%) of the title compound as a clear oil; TLC R$_f$ 0.50 (solvent system: 1:99 v/v methanol:dichloromethane); MS (ESI+) m/z 464.2 (M+H)$^+$, 486.1 (M+Na)$^+$; (ESI−) m/z 462.1 (M−H)$^−$; 1H-NMR (CDCl3) δ 7.3 (t, 2H), 7.2 (d, 3H), 6.6-6.4 (m, 1H), 6.3 (d, 1H), 4.3-4.2 (m, 1H), 3.9-3.8 (m, 1H), 3.7 (s, 3H), 3.7-3.5 (m, 1H), 3.0-2.8 (m, 1H), 2.8-2.5 (m, 2H), 2.4-2.2 (m, 4H), 1.8-1.2 (m, 12H), 1.1 (d, 3H).

Scheme 11, Step xxvi: Preparation of methyl 7-((R)-3,3-difluoro-5-((3S,4S,E)-3-hydroxy-4-methyl-7-phenylhept-1-en-1-yl)-2-oxopyrrolidin-1-yl)heptanoate (11B-1) and methyl 7-((R)-3,3-difluoro-5-((3R,4S,E)-3-hydroxy-4-methyl-7-phenylhept-1-en-1-yl)-2-oxopyrrolidin-1-yl)heptanoate (11B-2)

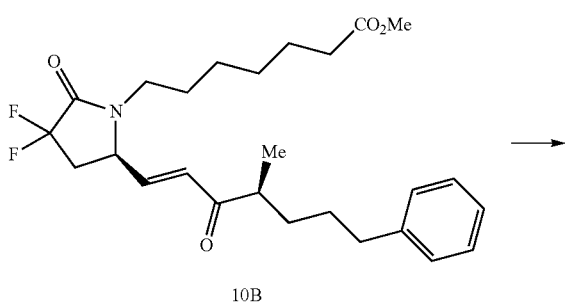

10B

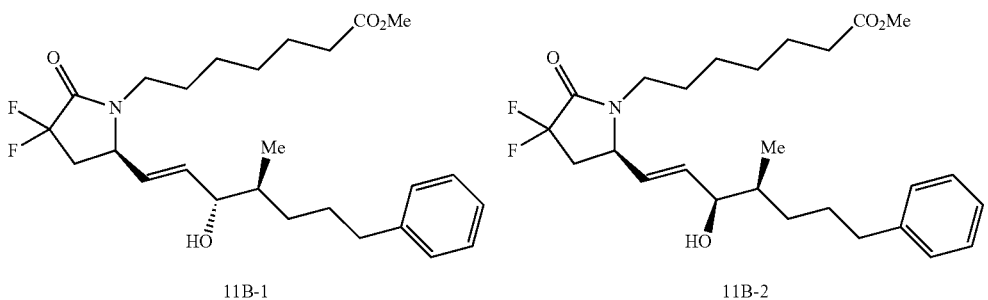

11B-1      11B-2

To a −40° C. solution of methyl 7-((R)-3,3-difluoro-5-((S,E)-4-methyl-3-oxo-7-phenylhept-1-en-1-yl)-2-oxopyrrolidin-1-yl)heptanoate (137 mg, 0.3 mmol) and (R)-(+)-2-methyl-CBS-oxazaborolidine (0.36 mL, 0.36 mmol, 1M in toluene) in dichloromethane (20 mL) was added catecholborane (0.99 mL, 0.99 mmol, 1M in THF) over 10 minutes. The reaction was stirred for 6 hours between −40° C. and −30° C. The reaction was quenched with 1M HCl$_{aq}$ and warmed to room temperature. The reaction mixture was extracted with ethyl acetate and organic phase was washed sequentially with a 50% saturated aqueous solution of sodium chloride and a saturated aqueous solution of sodium chloride and dried over sodium sulfate, filtered and concentrated. The epimeric mixture (ratio 1.12:1.00, 11B-1 to 11B-2) of the title compounds was isolated by silica gel chromatography eluting with methanol:dichloromethane (1:200 v:v); TLC R$_f$ 0.65 (solvent system: 5:95 v/v methanol:dichloromethane).

Scheme 11, Step xxvii: Preparation of 7-((R)-3,3-difluoro-5-((3S,4S,E)-3-hydroxy-4-methyl-7-phenyl-hept-1-en-1-yl)-2-oxopyrrolidin-1-yl)heptanoic acid (26B-1)

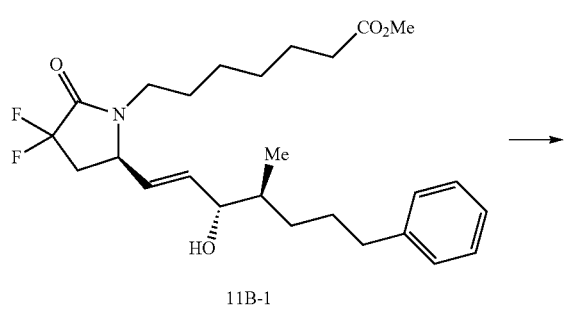

11B-1

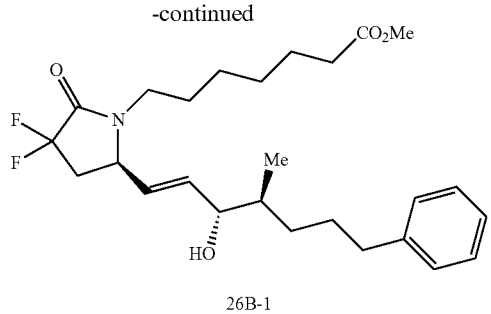

26B-1

To a solution consisting of methyl 7-((R)-3,3-difluoro-5-((3S,4S,E)-3-hydroxy-4-methyl-7-phenylhept-1-en-1-yl)-2-oxopyrrolidin-1-yl)heptanoate (3.3 mg, 0.007 mmol) in methanol (300 μL) was added lithium hydroxide (40 μL, 0.04 mmol, 1M aqueous solution) and the reaction was stirred for 16 hours. The reaction was quenched with the addition of a saturated aqueous solution of KHSO$_4$ and brine, and organic material was extracted with ethyl acetate. The organic phase was concentrated, redissolved in ethyl acetate, filtered, and concentrated to give 7.7 mg (crude) of a clear oil; TLC R$_f$ 0.45 (solvent system: 1:10:90 v/v acetic acid:methanol:dichloromethane); $^1$H-NMR (CDCl$_3$) δ 7.3 (t, 2H), 7.2 (d, 3H), 5.9-5.7 (m, 1H), 5.5-5.4 (m, 1H), 4.2-4.0 (m, 2H), 3.6-3.5 (m, 1H), 3.0-2.9 (m, 1H), 2.8-2.6 (br s, 1H), 2.6 (t, 2H), 2.4-2.0 (m, 6H), 1.8-1.4 (m, 7H), 1.4-1.0 (m, 6H), 0.9 (dt, 3H)

Scheme 11, Step xxv: Preparation of methyl 5-(3-((R)-3,3-difluoro-5-((S,E)-4-methyl-3-oxo-7-phenyl-hept-1-en-1-yl)-2-oxopyrrolidin-1-yl)propyl)thiophene-2-carboxylate (10C)

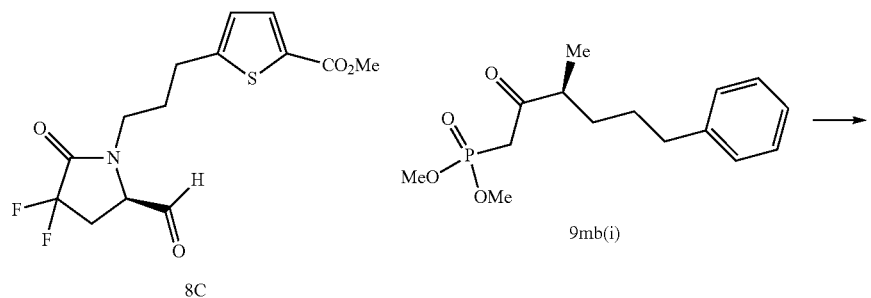

8C

9mb(i)

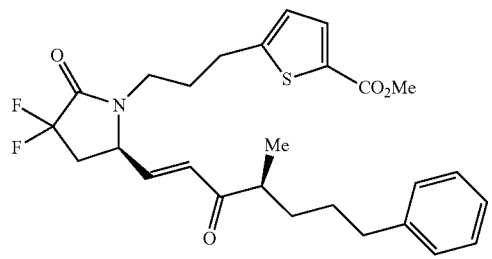

10C

To a 0° C. mixture consisting of dimethyl (S)-(3-methyl-2-oxo-6-phenylhexyl) phosphonate (1.79 g, 6.0 mmol), methyl (R)-5-(3-(3,3-difluoro-5-formyl-2-oxopyrrolidin-1-yl)propyl)thiophene-2-carboxylate (3.1 g, 6.0 mmol), and lithium chloride (763 mg, 18.0 mmol) in THF (70 mL) was added triethylamine (1.67 g, 12.0 mmol) dropwise over 1 minute. The reaction was stirred for 16 hours, warming to room temperature. To the reaction mixture was added a saturated aqueous solution of ammonium chloride and the organic material was extracted with ethyl acetate. The combined organic phase was washed with a saturated aqueous solution of sodium chloride and dried over sodium sulfate, filtered and concentrated. The residue was purified by silica gel chromatography eluting with methanol:dichloromethane (1:200 v:v) to afford 1.97 g (63%) of the title compound as a clear oil; TLC $R_f$ 0.75 (solvent system: 95:5 v/v dichloromethane:methanol); $^1$H-NMR (CDCl$_3$) δ 7.6 (d, 1H), 7.3-7.2 (m, 2H), 7.2-7.1 (m, 3H), 6.8 (d, 1H), 6.45 (dd, 1H), 6.25 (d, 1H), 4.2-4.1 (m, 1H), 3.85 (s, 3H), 3.7-3.6 (m, 1H), 3.0-2.9 (m, 1H), 2.83 (t, 2H), 2.7-2.6 (m, 4H), 2.4-2.2 (m, 1H), 2.0-1.9 (m, 2H), 1.7-1.5 (m, 3H), 1.5-1.3 (m, 1H), 1.1 (d, 3H).

Scheme 11, Step xxvi: Preparation of methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (11C-1) and methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (11C-2)

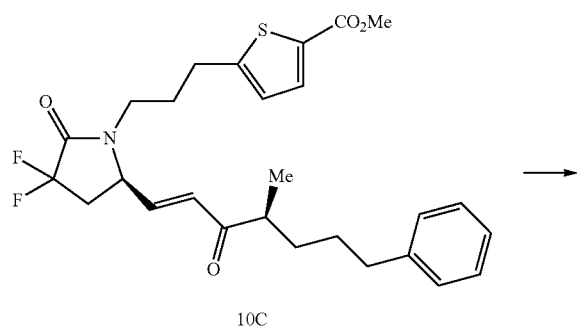

10C

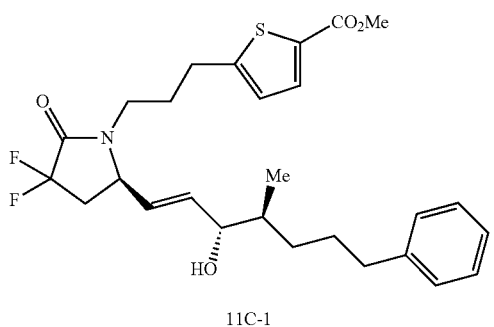

11C-1

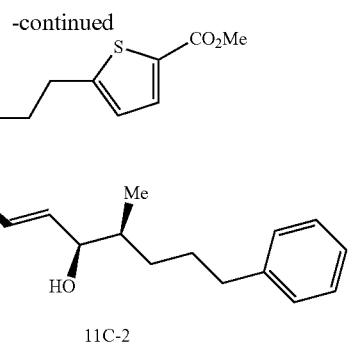

11C-2

Reaction 1: To a solution consisting of methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate (50.0 mg, 0.1 mmol) and (R)-(+)-2-methyl-CBS-oxazaborolidine (0.12 mL, 0.12 mmol, 1M in toluene) in dichloromethane (1 mL) was added catecholborane (0.1 mL, 0.1 mmol, 1M in THF) in dichloromethane (5 mL) over 15 minutes. The reaction was stirred for 2 hours. The reaction was quenched with 1M HCl and extracted with ethyl acetate. The combined organic phase was sequentially washed with a 50% saturated aqueous solution of sodium chloride and a saturated aqueous solution of sodium chloride, dried over sodium sulfate, filtered and concentrated. The residue, comprising the epimeric mixture of the title compounds in relation to C15-OH, was isolated by silica gel chromatography eluting with methanol:dichloromethane (1:250 v:v) to afford 23 mg as a clear oil; TLC $R_f$ 0.50 (solvent system: 97:3 v/v dichloromethane:methanol).

Reaction 2: Methyl 5-(3-((R)-3,3-difluoro-5-((4S,E)-3-hydroxy-4-methyl-7-phenylhept-1-en-1-yl)-2-oxopyrrolidin-1-yl)propyl)thiophene-2-carboxylate, the epimeric mixture of the title compounds, was prepared by the method as described above in reaction 1 except 4 molar equivalents of catecholborane (0.4 mL, 0.4 mmol, 1M in THF) was used instead of 1 equivalent to afford 70 mg as a clear oil; TLC $R_f$ 0.50 (solvent system: 3:97 v/v dichloromethane:methanol).

Reaction 3: Methyl 5-(3-((R)-3,3-difluoro-5-((4S,E)-3-hydroxy-4-methyl-7-phenylhept-1-en-1-yl)-2-oxopyrrolidin-1-yl)propyl)thiophene-2-carboxylate, the epimeric mixture of the title compounds, was prepared by the method as described above in reaction 1 except on a larger scale. The reaction mixture comprising methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate (553 mg, 1.1 mmol), (R)-(+)-2-methyl-CBS-oxazaborolidine (1.32 mL, 1.32 mmol, 1M in toluene) and catecholborane (1.1 mL, 1.1 mmol, 1M in THF) afforded 226 mg as a clear oil; TLC $R_f$ 0.50 (solvent system: 3:97 v/v dichloromethane:methanol).

The pure single epimer 11C-1 was isolated from the combined epimeric mixture of the title compounds from Reactions 1, 2 and 3 by prep HPLC on an Agilent 1100 instrument, stationary phase Luna 5 m Silica 250×21.2 mm column, mobile phase 96:4 heptane:ethanol, retention time 26-29 minutes.

11C-1: 110 mg (17%) as a white solid; TLC $R_f$ 0.50 (solvent system: 97:3 v/v dichloromethane:methanol); analytical HPLC, retention time 16.3 min, Agilent 1100 ultra-violet detector at 210 nm, stationary phase, Phenomenex Luna Silica, 5μ, 4.6×250 mm, mobile phase, 95:5 heptane:ethanol, flow rate 1 mL/min; $^1$H-NMR (CDCl$_3$) δ 7.6 (d, 1H), 7.3-7.2 (m, 2H), 7.2-7.1 (m, 3H), 6.8 (d, 1H), 5.75 (dd, 1H), 5.4 (dd, 1H), 4.1-4.0 (m, 2H), 3.82 (s, 3H), 3.6-3.5 (m, 1H), 3.0-2.9 (m, 1H), 2.80 (t, 2H), 2.6-2.5 (m, 3H), 2.2-2.1 (m, 1H), 2.1-2.0 (m, 1H), 1.9-1.8 (m, 2H), 1.7-1.4 (m, 4H), 1.2-1.1 (m, 1H), 0.84 (d, 3H); $^{19}$F-NMR (CDCl$_3$, 376 Hz) δ −103.6 (ddd, J=270, 15, 3 Hz, 1F), −105.6 (ddd, J=271, 17, 15 Hz, 1F).

Reaction 4: To a solution consisting of methyl 5-(3-((R)-3,3-difluoro-5-((S,E)-4-methyl-3-oxo-7-phenylhept-1-en-1-yl)-2-oxopyrrolidin-1-yl)propyl)thiophene-2-carboxylate (10 mg, 0.02 mmol) and (R)-(+) 2-methyl-CBS-oxazaborolidine (0.040 mL, 0.04 mmol, 1M in toluene) in dichloromethane (1 mL) was added catecholborane (0.060 mL, 0.06 mmol, 1M in THF) in dichloromethane (1 mL) over 15 minutes. The reaction was stirred for 2 hours. The reaction was quenched with 1 M HCl and extracted with ethyl acetate. The crude product, as a clear oil, was analyzed by HPLC using a Phenomenex Luna 5µ Silica (2) 4.6×250 mm column at 30° eluting with 95:5:0.1 hexanes:2-propanol: acetic acid to reveal a diastereomeric ratio relative to C15 hydroxy group of 64:36 methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (11C-1) to methyl 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylate (11C-2); TLC R$_f$0.50 (solvent system: 3:97 v/v dichloromethane:methanol).

Scheme 11, Step xxvii: Preparation of 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylic acid (26C-1)

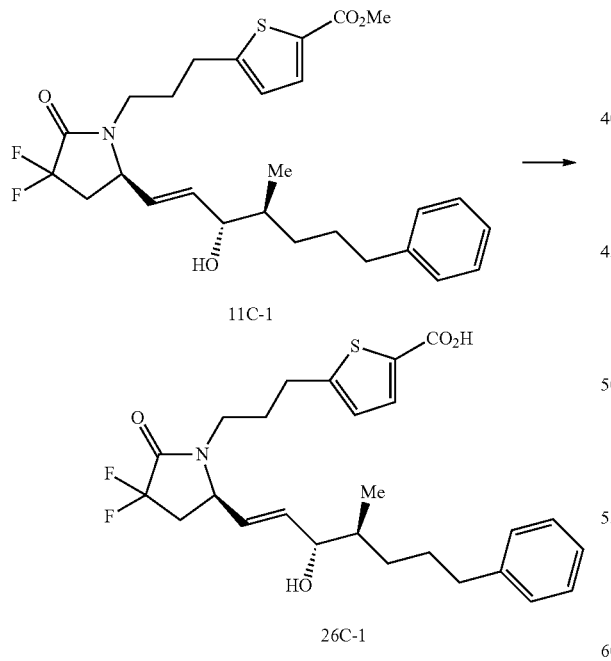

11C-1

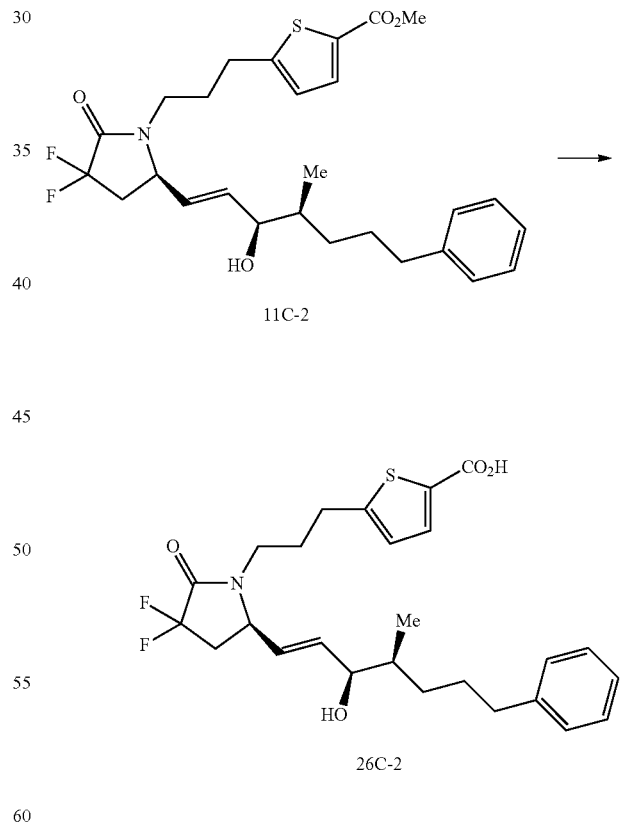

11C-2

26C-1

26C-2

To a solution of methyl 5-(3-((R)-3,3-difluoro-5-((3S,4S,E)-3-hydroxy-4-methyl-7-phenylhept-1-en-1-yl)-2-oxopyrrolidin-1-yl)propyl)thiophene-2-carboxylate (96 mg, 0.19 mmol) in methanol (3 mL) was added lithium hydroxide (950 mL, 0.95 mmol), and the reaction mixture was stirred for 16 hours. The reaction was quenched with the addition of a saturated aqueous solution of KHSO$_4$, and the organic material was extracted with ethyl acetate. The combined organic phase was washed with a saturated solution of sodium chloride, dried over sodium sulfate, filtered and concentrated. The residue was purified by silica gel chromatography eluting with acetic acid:methanol:dichloromethane (1:2:140 v:v) to afford 75 mg (80%) of the title compound as a white solid; TLC R$_f$0.50 (solvent system: 1:4:96 v/v acetic acid:methanol:dichloromethane); $^1$H-NMR (CDCl$_3$) δ 7.7 (d, 1H), 7.3-7.2 (m, 2H), 7.2-7.1 (m, 3H), 6.85 (d, 1H), 5.75 (dd, 1H), 5.42 (dd, 1H), 4.1-4.0 (m, 2H), 3.7-3.5 (m, 1H), 3.1-3.0 (m, 1H), 2.85 (dt, 2H), 2.7-2.5 (m, 3H), 2.2 (dq, 1H), 2.0-1.9 (m, 2H), 1.8-1.5 (m, 3H), 1.5-1.4 (m, 1H), 1.2-1.1 (m, 1H) 0.84 (d, 3H); $^{13}$C-NMR (CDCl$_3$) δ 166.62, 163.64 (t, J=21 Hz) 153.28, 142.24, 137.77, 135.29, 129.32 (d, J=233 Hz), 128.35 (2C), 128.31 (2C), 126.25, 125.79, 75.27, 55.24, 40.48, 38.66, 36.54 (t, J=21 Hz), 36.00, 31.60, 28.82, 28.37, 27.77, 14.99, 14.18; $^{19}$F-NMR (CDCl$_3$) δ −103.6 (ddd, J=271, 16, 3 Hz, 1F), −105.6 (ddd, J=270, 17, 15 Hz, 1F).

Scheme 11, Step xxvii: Preparation of 5-(3-((R)-3,3-difluoro-5-((3R,4S,E)-3-hydroxy-4-methyl-7-phenylhept-1-en-1-yl)-2-oxopyrrolidin-1-yl)propyl)thiophene-2-carboxylic acid (26C-2)

5-(3-((R)-3,3-Difluoro-5-((3R,4S,E)-3-hydroxy-4-methyl-7-phenylhept-1-en-1-yl)-2-oxopyrrolidin-1-yl)propyl)thiophene-2-carboxylic acid was prepared in the same manner, by the hydrolysis of the corresponding methyl ester 11C-2 as described for 26C-1; TLC R$_f$0.55 (solvent system: 96:4:1 v/v dichloromethane-methanol-acetic acid); MS (ESI$^-$) m/z 490.2 (M−H)$^-$.

Scheme 11, Step xxv: Preparation of methyl 5-(3-((R)-3,3-difluoro-5-((R,E)-4-methyl-3-oxo-7-phenyl-hept-1-en-1-yl)-2-oxopyrrolidin-1-yl)propyl)thio-phene-2-carboxylate (10D)

Scheme 11, Step xxvi: Preparation of methyl 5-(3-((R)-3,3-difluoro-5-((3S,4R,E)-3-hydroxy-4-methyl-7-phenylhept-1-en-1-yl)-2-oxopyrrolidin-1-yl)pro-pyl)thiphene-2-carboxylate (11D-1) and methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate (11D-2)

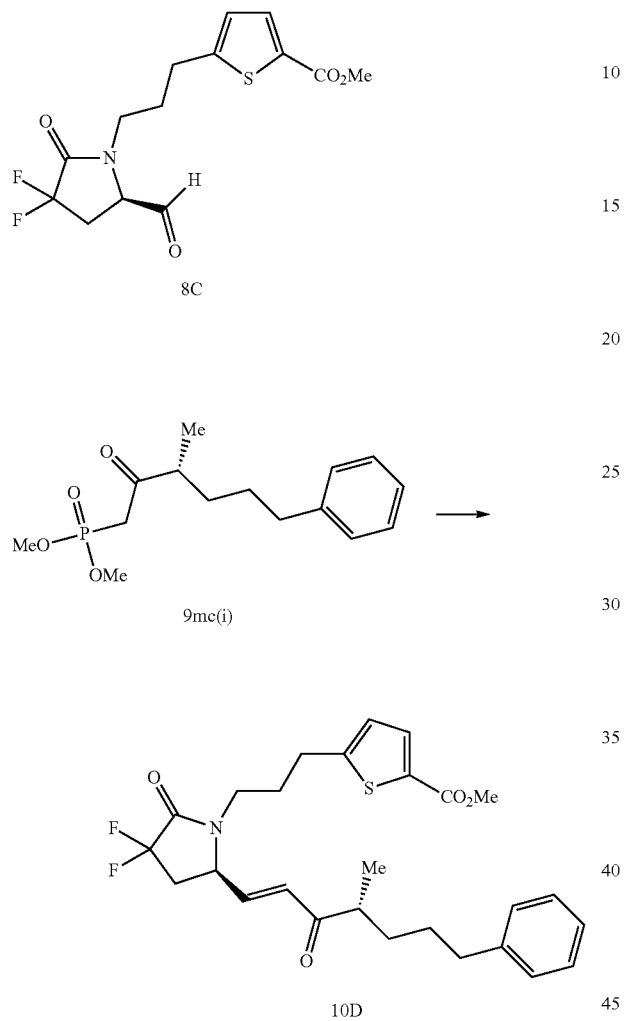

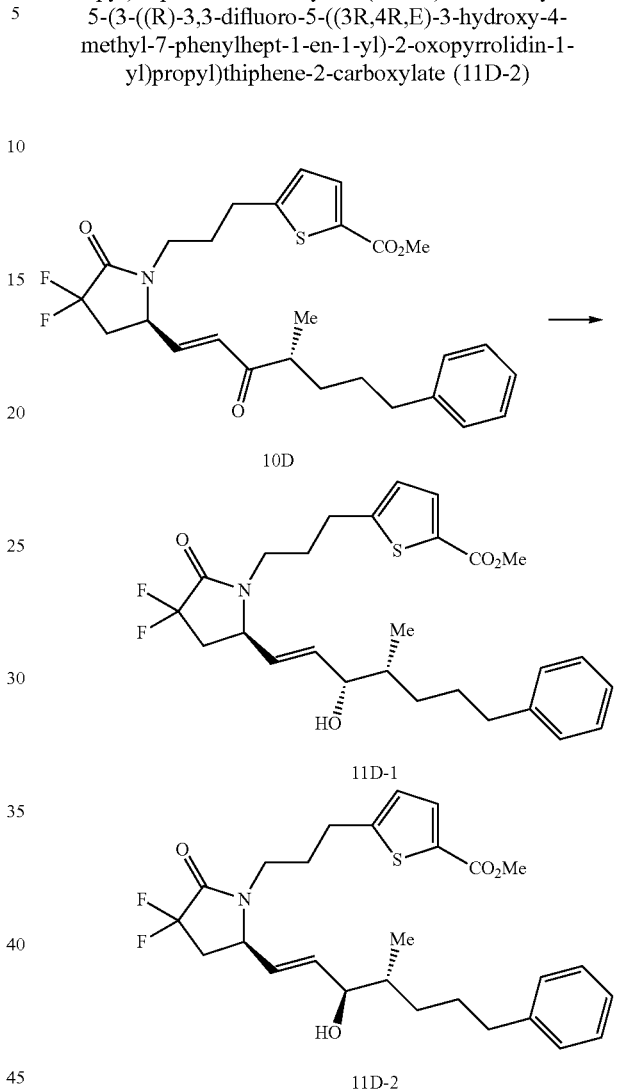

Methyl 5-(3-((R)-3,3-difluoro-5-((R,E)-4-methyl-3-oxo-7-phenyl-1-en-1-yl)-2-oxopyrrolidin-1-yl)propyl)thio-phene-2-carboxylate was prepared in the same manner described above for (10C) using (R)-methyl 5-(3-(3,3-dif-luoro-5-formyl-2-oxopyrrolidin-1-yl)propyl)thiophene-2-carboxylate (8C) and (R)-dimethyl (3-methyl-2-oxo-6-phe-nylhexyl)phosphonate (9mc(i)) to give 1.3 g (53%) of a colorless oil; TLC $R_f$ 0.42 (solvent system 35:65 v/v ethyl acetate-heptane); MS (ESI⁻) m/z 502 (M−H)⁻; ¹H NMR (CD₃OD) δ 7.60 (d, J=3.66 Hz, 1H), 7.28-7.18 (m, 2H), 7.17-7.11 (m, 3H), 6.89 (d, J=3.94 Hz 1H), 6.55 (dd, J=8.79, 15.38 Hz, 1H), 6.42 (d, J=15.75 Hz, 1H), 4.43 (td, J=4.07, 8.33 Hz, 1H), 3.82 (s, 3H), 3.63-3.47 (m, 1H), 3.13-3.01 (m, 1H), 2.91-2.72 (m, 4H), 2.58 (t, J=7.32 Hz, 2H), 2.35 (d, J=15.01 Hz, 1H), 2.01-1.84 (m, 2H), 1.71-1.51 (m, 3H), 1.41-1.28 (m, 1H), 1.04 (d, J=6.59 Hz, 3H); ¹⁹F NMR (CD₃OD) δ −104.2 (ddd, 1F), −107.2 (ddd, 1F); $[\alpha]^T_\lambda$=α/cl, $[\alpha]^{21.9}_D$=−0.090/(0.01606 g/1.5 mL)(0.5)=−16.81 (c=1.07, CHCl₃).

Methyl 5-(3-((5R)-3,3-difluoro-5-((4R,E)-3-hydroxy-4-methyl-7-phenylhept-1-en-1-yl)-2-oxopyrrolidin-1-yl)pro-pyl)thiophene-2-carboxylate, the epimeric mixture of the title compound, was prepared by the primary method described for 11A-1 and 11A-2 using cerium chloride hep-tahydrate and sodium borohydride.

The pure epimers of 11D-1 and 11D-2 were isolated following separation by prep HPLC from its epimeric part-ner.

Gilson Prep HPLC, Luna silica 5p, 21.2×250 mm, ultra-violet detector 210 nm, mobile phase 96:4:0.1 heptane-ethanol-acetic acid, 21.2 ml/min.

11D-1: 175 mg as a clear oil; TLC $R_f$ 0.31 (solvent system: 35:65 v/v ethyl acetate-heptane); HPLC retention time 39 min; MS (ESI⁺) m/z 528 (M+Na)⁺; ¹H NMR (CD₃OD) δ 7.62 (d, J=3.66 Hz, 1H), 7.25-7.10 (m, 5H), 6.91 (d, J=3.92 Hz, 1H), 5.81 (dd, J=6.23, 15.38 Hz, 1H), 5.42 (dd, J=9.34, 15.20 Hz, 1H), 4.25 (dd, J=4.58, 7.87 Hz, 1H), 3.99-3.89 (m, 1H), 3.80 (s, 3H), 3.55-3.47 (m, 1H), 3.34 (s, 1H), 3.16-3.03 (m, 1H), 2.85 (dt, J=3.48, 7.42 Hz, 3H), 2.71-2.51 (m, 2H), 2.32-2.19 (m, 1H), 1.99-1.85 (m, 2H), 1.71-1.44 (m, 4H), 1.11 (s, 1H), 0.86 (d, J=6.96 Hz, 3H); $^{19}$F NMR (CD$_3$OD) δ −104.4 (ddd, 1F), −107.3 (ddd, 1F); $[α]^T_λ$=α/cl, $[α]^{21.9}_D$=−0.004/(0.01568 g/1.5 mL)(0.5)=−0.765° (c=1.045, CHCl$_3$).

11D-2: 580 mg as a clear oil; TLC R$_f$ 0.31 (solvent system: 35:65 v/v ethyl acetate-heptane); HPLC retention time 35 min; MS (ESI$^+$) m/z 528 (M+Na)$^+$; $^1$H NMR (CD$_3$OD) δ 7.63-7.61 (m, 1H), 7.25-7.10 (m, 5H), 6.92 (d, J=3.91 Hz, 1H), 5.85 (dd, J=5.68, 15.20 Hz, 1H), 5.43 (dd, J=9.34, 15.20 Hz, 1H), 4.29-4.22 (m, 1H), 3.96 (dt, J=1.46, 5.49 Hz, 1H), 3.82-3.80 (m, 3H), 3.59-3.47 (m, 1H), 3.36-3.32 (m, 1H), 3.11 (dd, J=6.04, 7.87 Hz, 1H), 2.85 (t, J=7.51 Hz, 2H), 2.79-2.67 (m, 1H), 2.59 (t, J=7.51 Hz, 2H), 2.28-2.15 (m, 1H), 1.99-1.86 (m, 2H), 1.75-1.52 (m, 3H), 1.47 (td, J=5.17, 13.46 Hz, 1H), 1.17-1.07 (m, 1H), 0.85 (d, J=6.59 Hz, 3H); $^{19}$F NMR (CD$_3$OD) δ −104.5 (ddd, 1F), −107.2 (ddd, 1F).

Scheme 11, Step xxvi: Alternative preparation of methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (11D-1) and methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate (11D-2)

To a solution consisting of methyl 5-(3-((R)-3,3-difluoro-5-((R,E)-4-methyl-3-oxo-7-phenylhept-1-en-1-yl)-2-oxopyrrolidin-1-yl)propyl)thiophene-2-carboxylate (10 mg, 0.02 mmol) and (R)-(+) 2-methyl-CBS-oxazaborolidine (0.040 mL, 0.04 mmol, 1$\underline{M}$ in toluene) in dichloromethane (1 mL) was added catecholborane (0.060 mL, 0.06 mmol, 1$\underline{M}$ in THF) in dichloromethane (1 mL) over 15 minutes. The reaction was stirred for 2 hours. The reaction was quenched with 1 $\underline{M}$ HCl and extracted with ethyl acetate. The crude product, as a clear oil, was analyzed by HPLC using a Phenomenex Luna 5μ Silica (2) 4.6×250 mm column at 30° eluting with 95:5:0.1 hexanes:2-propanol:acetic acid to reveal a diastereomeric ratio relative to C15 hydroxy group of 99:1 methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (11D-1) to methyl 5-(3-((R)-3,3-difluoro-5-((3R,4R,E)-3-hydroxy-4-methyl-7-phenylhept-1-en-1-yl)-2-oxopyrrolidin-1-yl)propyl)thiphene-2-carboxylate (11D-2); TLC R$_f$ 0.50 (solvent system: 3:97 v/v dichloromethane:methanol).

Scheme 11, Step xxvii: Preparation of 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (26D-1)

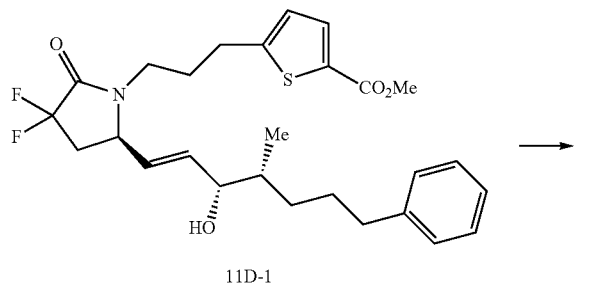

11D-1

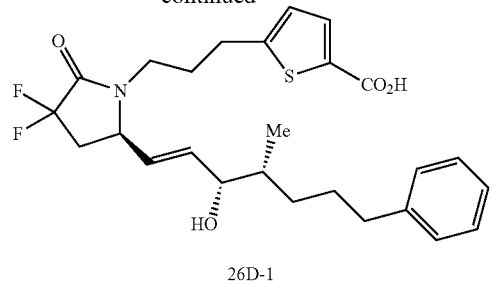

26D-1

To a solution consisting of methyl 5-(3-((R)-3,3-difluoro-5-((3S,4R,E)-3-hydroxy-4-methyl-7-phenylhept-1-en-1-yl)-2-oxopyrrolidin-1-yl)propyl)thiphene-2-carboxylate (140 mg, 0.28 mmol) in a mixture of 1:1 methanol-THF (6 mL) was added aqueous 2$\underline{M}$ lithium hydroxide (3 mL). The mixture stirred at room temperature for 6 hours. The mixture was cooled to 0° C. and acidified with 6$\underline{M}$ HCl and extracted with ethyl acetate three times. The combined organic layer was washed with brine three times, dried over sodium sulfate, filtered and concentrated under vacuum. The residue was purified by silica gel chromatography eluting with ethyl acetate-heptane-acetic acid (50:50:0.4 v/v/v) to give 60 mg (44%) of the title compound as a colorless oil; TLC R$_f$ 0.45 (solvent system: 60:40:1 v/v/v ethyl acetate-heptane-acetic acid; MS (ESI$^-$) m/z 490 (M−H)$^-$; $[α]^T_λ$=α/cl, $[α]^{21.9}_D$=−0.011/(0.0163 g/1.5 mL)(0.5)=−2.03° (c=1.09, CHCl$_3$).

We claim:
1. A method of preparing a compound of formula (10)

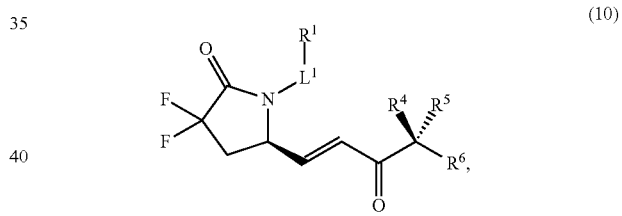

(10)

the method comprising reacting a compound of formula (8) with a compound of formula (9) in the presence of a trialkylamine base and lithium chloride;

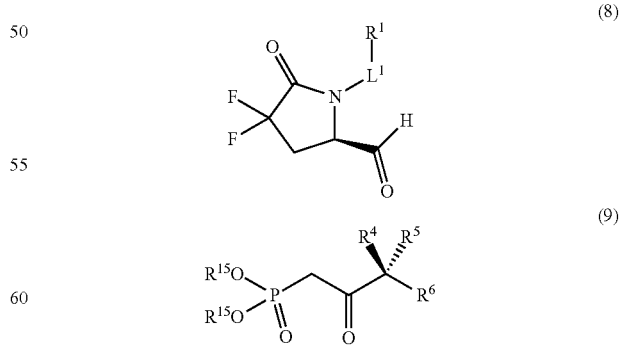

wherein:
L$^1$ is
a) C$_3$-C$_7$alkylene, C$_3$-C$_7$alkenylene, or C$_3$-C$_7$alkynylene; or b) —$(CH_2)_{n1}$-$G^2$-$(CH_2)_p$—, —$(CH_2)_{n2}$—C≡C-$G^2$-, or —$(CH_2)_{n2}$—C($R^{12}$)=C($R^{12}$)-$G^2$-, wherein n1 is 2, 3, 4, or 5, n2 is 1, 2, or 3, p is 0, 1, 2, or 3, and n1+p=2, 3, 4, 5, or 6;

$G^2$ is

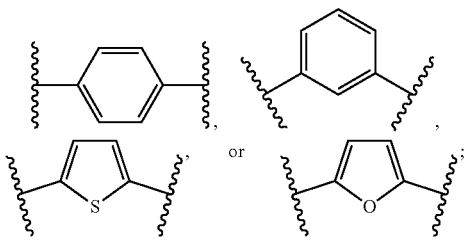

$R^1$ is a protected carboxylic acid;
$R^{12}$, at each occurrence, is independently H or $C_1$-$C_4$alkyl;
$R^4$ and $R^5$ are each independently H or $C_1$-$C_4$ alkyl; or $R^4$ and $R^5$ together with the carbon to which they are attached form a $C_3$-$C_5$ cycloalkyl;
$R^6$ is aryl, heteroaryl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the aryl and heteroaryl are optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy; and —$C_1$-$C_3$alkylene-$C_1$-$C_3$alkoxy;
$L^3$ is $C_1$-$C_6$alkylene, $C_2$-$C_6$alkenylene, or $C_2$-$C_6$alkynylene;
$R^7$ is $C_3$-$C_8$cycloalkyl, aryl, heteroaryl, or heterocyclyl; wherein $R^7$ is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and $R^{15}$ is $C_1$-$C_6$alkyl.

2. The method of claim 1 wherein:
$L^1$ is n-hexylene, —$(CH_2)_3$-$G^2$-, —$CH_2$—C≡C-$G^2$-, or —$CH_2$—C(H)=C(H)-$G^2$-;
$G^2$ is

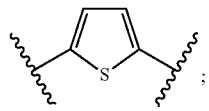 [SMILES: *c1ccc(*)s1]

$R^4$ and $R^5$ are each independently H or $C_1$-$C_4$ alkyl;
$R^6$ is phenyl, $C_3$-$C_{10}$alkyl, $C_3$-$C_{10}$alkenyl, $C_3$-$C_{10}$alkynyl, $C_3$-$C_{10}$haloalkyl, $C_3$-$C_{10}$haloalkenyl, $C_3$-$C_{10}$haloalkynyl, or $L^3$-$R^7$; wherein the phenyl is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy; and
$R^7$ is phenyl, which is optionally substituted with 1, 2, 3, or 4 substituents selected from the group consisting of $C_1$-$C_4$alkyl, $C_1$-$C_3$haloalkyl, cyano, halogen, $C_1$-$C_3$alkoxy, $C_1$-$C_3$haloalkoxy, and —$C_1$-$C_3$alkylene-$C_1$-$C_3$alkoxy.

3. The method of claim 2 wherein:
$L^1$ is —$(CH_2)_3$-$G^2$-;
$R^4$ and $R^5$ are each independently H or methyl;
$R^6$ is —$CH_2$—C≡C—$C_1$-$C_4$alkyl or $L^3$-$R^7$;
$L^3$ is $C_3$-$C_6$alkylene; and
$R^7$ is phenyl.

* * * * *